US011680275B2

(12) United States Patent
Esteves et al.

(10) Patent No.: US 11,680,275 B2
(45) Date of Patent: Jun. 20, 2023

(54) SELF-REGULATING AAV VECTORS FOR SAFE EXPRESSION OF MECP2 IN RETT SYNDROME

(71) Applicant: UNIVERSITY OF MASSACHUSETTS, Boston, MA (US)

(72) Inventors: Miguel Sena Esteves, Westford, MA (US); Guangping Gao, Westborough, MA (US); Michael R. Green, Boylston, MA (US); Dan Wang, Belchertown, MA (US); Tessa Mercedes Simone, Worcester, MA (US)

(73) Assignee: University of Massachusetts, Boston, MA (US)

( * ) Notice: Subject to any disclaimer, the term of this patent is extended or adjusted under 35 U.S.C. 154(b) by 795 days.

(21) Appl. No.: 16/619,733

(22) PCT Filed: Jun. 6, 2018

(86) PCT No.: PCT/US2018/036200
§ 371 (c)(1),
(2) Date: Dec. 5, 2019

(87) PCT Pub. No.: WO2018/226785
PCT Pub. Date: Dec. 13, 2018

(65) Prior Publication Data
US 2020/0181646 A1 Jun. 11, 2020

Related U.S. Application Data

(60) Provisional application No. 62/516,060, filed on Jun. 6, 2017.

(51) Int. Cl.
*C12N 15/86* (2006.01)
*C07K 14/47* (2006.01)

(52) U.S. Cl.
CPC .......... *C12N 15/86* (2013.01); *C07K 14/4702* (2013.01); *C07K 2319/41* (2013.01); *C12N 2310/141* (2013.01); *C12N 2330/10* (2013.01); *C12N 2750/14143* (2013.01)

(58) Field of Classification Search
None
See application file for complete search history.

(56) References Cited

U.S. PATENT DOCUMENTS

| | | |
|---|---|---|
| 9,585,971 B2 | 3/2017 | Deverman et al. |
| 2003/0138772 A1 | 7/2003 | Gao et al. |
| 2004/0106566 A1 | 6/2004 | Lin et al. |
| 2016/0000794 A1 | 1/2016 | Chiorini et al. |

FOREIGN PATENT DOCUMENTS

| | | |
|---|---|---|
| EP | 3121284 A1 | 1/2017 |
| JP | 2011-501760 A | 1/2011 |
| JP | 2011-510021 A | 3/2011 |
| JP | 2013-540789 A | 11/2013 |
| WO | WO 2009/053442 A1 | 4/2009 |
| WO | WO 2009/092049 A1 | 7/2009 |
| WO | WO 2010/105096 A2 | 9/2010 |
| WO | WO 2012/055826 A1 | 5/2012 |
| WO | WO 2015/127128 A2 | 8/2015 |
| WO | WO 2015/164786 A1 | 10/2015 |
| WO | WO 2016/054554 A1 | 4/2016 |
| WO | WO 2016/054557 A1 | 4/2016 |
| WO | WO 2016/065001 A1 | 4/2016 |
| WO | WO 2016/172008 A1 | 10/2016 |

OTHER PUBLICATIONS

Invitation to Pay Additional Fees for Application No. PCT/US2018/036200, dated Aug. 27, 2018.
International Search Report and Written Opinion for Application No. PCT/US2018/036200, dated Oct. 29, 2018.
International Preliminary Report on Patentability for Application No. PCT/US2018/036200, dated Dec. 19, 2019.
Suter et al., MECP2 Mutations in People without Rett Syndrome. J Autism Dev Disord. Mar. 2014; 44(3): 703-711. doi: 10.1007/s10803-013-1902-z. Author Manuscript.
Taganov et al., NF-?B-Dependent Induction of MicroRNA MiR-146, an Inhibitor Targeted to Signaling Proteins of Innate Immune Responses. Proc. Nat. Acad. Sci. USA. Aug. 15, 2006;103(33):12481-12486.
Wang et al., TransmiR: a transcription factor-microRNA regulation database. Nucleic Acids Res. 2010;38(Database issue):D119-D122. doi:10.1093/nar/gkp803.
EP 18812887.0, dated Feb. 26, 2021, Extended European Search Report.
Extended European Search Report for Application No. 18812887.0, dated Feb. 26, 2021.
GENBANK Submission; NCBI, Accession No. NM_001081979.1; Mus musculus methyl CpG binding protein 2 (Mecp2), transcript variant 1, mRNA. No Author Listed; May 18, 2014. Accessed: https://www.ncbi.nlm.nih.gov/nuccore/126517468?sat=18&satkey=13692580. Gadalla et al., Development of a Novel AAV Gene Therapy Cassette with Improved Safety Features and Efficacy in a Mouse Model of Rett Syndrome. Mol Ther Methods Clin Dev. Apr. 22, 2017;5:180-190. doi: 10.1016/j.omtm.2017.04.007. eCollection Jun. 16, 2017.
Geisler et al., MicroRNA-regulated viral vectors for gene therapy. World J Exp Med. May 20, 2016;6(2):37-54. doi: 10.5493/wjem.v6.i2.37.

(Continued)

*Primary Examiner* — Robert M Kelly
(74) *Attorney, Agent, or Firm* — Wolf, Greenfield & Sacks, P.C.

(57) ABSTRACT

In some aspects, the disclosure relates to compositions and methods of engineering a transgene. In some embodiments, the disclosure provides self-regulating recombinant nucleic acids, viral vectors and pharmaceutical compositions comprising a MeCP2 transgene. In some embodiments, compositions and methods described by the disclosure are useful for treating diseases and disorders associated with a loss of function mutation, for example Rett syndrome.

22 Claims, 8 Drawing Sheets

Specification includes a Sequence Listing.

(56) References Cited

OTHER PUBLICATIONS

Im et al., MicroRNAs in neuronal function and dysfunction. Trends Neurosci. May 2012;35(5):325-34. doi: 10.1016/j.tins.2012.01.004. Epub Mar. 19, 2012.
Klein et al., Homeostatic regulation of MeCP2 expression by a CREB-induced microRNA. Nat Neurosci. Dec. 2007;10(12):1513-4. doi: 10.1038/nn2010. Epub Nov. 11, 2007.
Liyanage et al., Decitabine alters the expression of Mecp2 isoforms via dynamic DNA methylation at the Mecp2 regulatory elements in neural stem cells. Mol Autism. Nov. 15, 2013;4(1):46. doi: 10.1186/2040-2392-4-46.
Sinnett et al., Improved MECP2 Gene Therapy Extends the Survival of MeCP2-Null Mice without Apparent Toxicity after Intracisternal Delivery. Mol Ther Methods Clin Dev. Apr. 19, 2017;5:106-115. doi: 10.1016/j.omtm.2017.04.006. eCollection Jun. 16, 2017.
Xie et al., MicroRNA-regulated, systemically delivered rAAV9: a step closer to CNS-restricted transgene expression. Mol Ther. Mar. 2011;19(3):526-35. doi: 10.1038/mt.2010.279. Epub Dec. 21, 2010.
Su et al., MeCP2 controls hippocampal brain-derived neurotrophic factor expression via homeostatic interactions with microRNA-132 in rats with depression. Mol Med Rep. Oct. 2015;12(4):5399-406. doi: 10.3892/mmr.2015.4104. Epub Jul. 20, 2015.

SELF-REGULATING AAV VECTORS FOR SAFE EXPRESSION OF MECP2 IN RETT SYNDROME

RELATED APPLICATIONS

This application is a national stage filing under 35 U.S.C. § 371 of international PCT application PCT/US2018/036200, filed Jun. 6, 2018, entitled "SELF-REGULATING AAV VECTORS FOR SAFE EXPRESSION OF MECP2 IN RETT SYNDROME", which claims the benefit under 35 U.S.C. § 119(e) of the filing date of U.S. Provisional Application Ser. No. 62/516,060, filed on Jun. 6, 2017, the entire contents of which are incorporated herein by reference.

BACKGROUND

Rett syndrome is a neurological disease caused by loss of function mutations in MeCP2. It has been observed that post-natal restoration of MeCP2 expression is effective in reversing some of the phenotypes present in MeCP2 mice, but safety concerns remain. Additionally, studies examining the therapeutic efficacy of certain MeCP2 vectors encoding the e1 isoform have observed only partial rescue of Rett phenotypes. These studies have typically focused on neonatal intravascular (IV) or intracerebroventricular (ICV) delivery, and in some instances have encountered lethal liver toxicity and hindlimb clasping.

SUMMARY

Aspects of the disclosure relate to the discovery that certain combinations of miRNA regulatory elements (MREs), for example miRNA binding sites associated with gene expression negative feedback loops and miRNA binding sites that de-target transgene expression from non-target tissues, enable tunable transgene expression within a narrow range compatible with normal protein function and avoidance of off-target transgene toxicity. In some embodiments, compositions and methods described by the disclosure are therefore useful for treating diseases and disorders associated with loss of function mutations, for example Rett syndrome which is associated with loss of function mutations in the MECP2 gene.

Accordingly, in some aspects, the disclosure provides a method of engineering a transgene, the method comprising: selecting a first gene encoding a first product in a cell; selecting a second gene encoding a second product in the cell; determining that expression of the second product is positively regulated by the first product in the cell; selecting an miRNA; determining that expression of the miRNA is positively regulated by the second product in the cell; and, engineering a transgene to express in the cell a transcript having a coding region encoding the first product and having one or more binding sites for the miRNA.

In some aspects, the disclosure provides a method of engineering a transgene, the method comprising: selecting a first gene encoding a first product in a cell; selecting an miRNA, the expression of which is positively regulated by the first product in the cell; and, engineering a transgene that expresses a transcript having a coding region encoding the first product and a 3'-non-coding region comprising one or more binding sites for the miRNA.

In some aspects, the disclosure provides a method of engineering a transgene, the method comprising: selecting a first gene encoding a first product in a cell; selecting a second gene encoding a second product in the cell; determining that expression of the second product is positively regulated by the first product in the cell; selecting an miRNA; determining that expression of the miRNA is positively regulated by the second product in the cell; and, engineering a transgene to express in the cell a transcript having a coding region encoding the first product and a 3'-non-coding region comprising one or more binding sites for the miRNA.

In some aspects, the disclosure provides a recombinant nucleic acid encoding a transcript having i) a coding region encoding a protein and ii) two or more miRNA binding sites, wherein the two or more miRNA binding sites comprise: at least one first miRNA binding site specific for a first miRNA that is positively regulated by expression of the protein in a cell of a target tissue; and at least one second miRNA binding site specific for a second miRNA that is expressed, independent of expression of the protein, in cells of a non-target tissue.

In some aspects, the disclosure provides a recombinant nucleic acid encoding a transcript having a coding region encoding human MeCP2 protein or a functional fragment thereof and a 3'-non-coding region comprising one or more miRNA binding sites, wherein the one or more miRNA binding sites comprise: at least one miRNA binding site specific for an miRNA that negatively regulates expression of the transcript; and at least one miRNA binding site specific for an miRNA that inhibits expression of the transcript in a non-target tissue.

In some aspects, the disclosure provides a recombinant nucleic acid encoding a transcript having: a coding region encoding human MeCP2 or a functional fragment thereof and, a 3'-non-coding region comprising one or more miRNA binding sites, wherein transcript is flanked by adeno-associated virus (AAV) inverted terminal repeats (ITRs). In some embodiments, an AAV ITR is an AAV2, AAV3, AAV4, AAV5, or AAV6 ITR. In some embodiments, AAV ITRs are AAV2 ITRs. In some embodiments, ITRs are artificial sequences that replace ITR function, for example as disclosed in WO/2016/172008.

In some aspects, the disclosure provides a viral vector comprising a recombinant nucleic acid as described by the disclosure. In some embodiments, a viral vector is an adeno-associated virus (AAV) vector, an adenovirus vector, a lentiviral vector, a herpesvirus vector, or a baculovirus vector.

In some aspects, the disclosure provides a recombinant adeno-associated virus (rAAV) comprising: a recombinant nucleic acid as described by the disclosure; at least one adeno-associated virus (AAV) inverted terminal repeat (ITR); and a capsid protein.

In some aspects, the disclosure provides a recombinant AAV (rAAV) vector for self-regulated expression of a protein, the rAAV vector comprising a nucleic acid engineered to express in a cell of a target tissue a transcript encoding the protein, wherein the transcript comprises at least one first miRNA binding site specific for a first miRNA, wherein expression of the first miRNA is positively regulated by expression of the protein in the cell.

In some aspects, the disclosure provides a composition comprising a recombinant nucleic acid as described by the disclosure, or an rAAV as described by the disclosure, and a pharmaceutically acceptable excipient. In some embodiments, a composition is formulated for injection, for example systemic injection (e.g., intravenous injection) or intrathecal injection.

In some embodiments, a first product is a protein. In some embodiments, the protein is MeCP2, for example MeCP2 isoform e1 or MeCP2 isoform e2. In some embodiments, a first product is an miRNA or a long non-coding RNA.

In some embodiments, a second product is a protein, or nucleic acid. In some embodiments, the second product is bone-derived neurotrophic factor (BDNF). In some embodiments, the nucleic acid is an miRNA (e.g., miR-132). In some embodiments, the first miRNA is miR-132.

In some embodiments, at least one miRNA binding site specific for an miRNA that negatively regulates expression of the transcript comprises a miR-132 binding site, for example two or three miR-132 binding sites.

In some embodiments, at least one miRNA binding site specific for an miRNA that inhibits expression of the transcript in a non-target tissue comprises a miR-1 binding site, mir-122 binding site, or miR-1 and miR-122 binding site. In some embodiments, the at least one miRNA binding site specific for an miRNA that inhibits expression of the transcript in a non-target tissue comprises three miR-1 binding sites (e.g., 3×-miR-1) and three miR-122 binding sites (e.g., 3×-miR-122).

In some embodiments, methods described by the disclosure further comprise the step of engineering the 3'-non-coding region of the transcript to comprise one or more binding sites for one or more de-targeting miRNAs. In some embodiments, one or more de-targeting miRNAs inhibit expression of the transgene from liver, heart, lung, muscle, pancreas, or immune (e.g., antigen presenting) cells. In some embodiments, one or more de-targeting miRNA is miR-122, miR-1, or miR-122 and miR-1. In some embodiments, one or more de-targeting miRNAs inhibit expression of the transgene in immune cells, such as antigen presenting cells (e.g., dendritic cells, macrophages, etc.). In some embodiments, one or more de-targeting miRNA is miR-15a, miR-16-1, miR-17, miR-18a, miR-19a, miR-20a, miR-19b-1, miR-21, miR-29a, miR-29b, miR-29c, miR-30b, miR-31, miR-34a, miR-92a-1, miR-106a, miR-125a, miR-125b, miR-126, miR-142-3p, miR-146a, miR-150, miR-155, miR-181a, miR-223 or miR-424.

In some embodiments, an miRNA binding site or miRNA binding sites is located between the last codon of the coding region and the poly-A tail of the transcript.

In some embodiments of methods described by the disclosure, the step of engineering the transgene comprises inserting the transgene into a vector. In some embodiments, a vector is a cloning vector, expression vector, plasmid, or viral vector.

In some embodiments, a recombinant nucleic acid further comprises a promoter, for example a mouse MeCP2 promoter. In some embodiments, a mouse MeCP2 promoter comprises the sequence set forth in SEQ ID NO: 3.

In some embodiments, a recombinant nucleic acid is located on a plasmid.

In some embodiments, a capsid protein is a capsid protein that facilitates crossing of the rAAV across the blood-brain barrier of a subject. In some embodiments, a capsid protein has a serotype selected from the group consisting of AAV-PHP.B, AAV1, AAV2, AAV2i8, AAV2.5, AAV5, AAV6, AAV8, AAVrh8, AAV9, AAVrh10, AAV-B1, AAV9.45A-String (e.g., AAV9.45-AS), AAV9.45Angiopep, AAV9.47-Angiopep, and AAV9.47-AS, AAV5, AAVrh39, AAVrh43, CAM130, and AAV9HR. In some embodiments, a capsid protein has a serotype as described in WO2015/127128, WO2016/054554, WO2016/054557, or WO2016/065001.

In some embodiments, a capsid protein comprises or consists of a sequence set forth in SEQ ID NO: 14 or 15 (e.g., AAV-PHP.B or AAV9).

In some aspects, the disclosure provides a method of treating Rett syndrome in a subject, the method comprising, administering to a subject having or suspected of having Rett syndrome an effective amount of: a recombinant nucleic acid as described by the disclosure; a rAAV as described by the disclosure; or, a composition as described by the disclosure.

In some embodiments, the subject is a human subject. In some embodiments, a subject is less than one year old. In some embodiments, a subject is characterized by a mutation in at least one copy of the MeCP2 gene, for example a loss of function mutation.

In some embodiments, a recombinant nucleic acid, rAAV or composition as described by the disclosure is administered by injection, for example systemic injection (e.g., intravenous injection) or intrathecal injection. In some embodiments, the administration results in the effective amount of the recombinant nucleic acid, rAAV or composition crossing the blood-brain barrier of a subject. In some embodiments, the administration results in a non-toxic level of MeCP2 expression in the brain of the subject.

BRIEF DESCRIPTION OF DRAWINGS

FIG. 1A shows a schematic depiction of a homeostatic mechanism of MeCP2 auto-regulation. FIG. 1B shows a schematic depiction of the structure of self-regulated AAV-MeCP2 vectors encoding human MeCP2-e1 with a myc tag under a mouse MeCP2 promoter (−223 to +56) and different microRNA recognition elements (e.g., miR-122/1T; miR-132T).

FIG. 2A shows MeCP2 expression measured by Western blot. FIG. 2B shows MeCP2 expression measured by a normalized protein expression assay (FIG. 2B). FIG. 2C shows a toxicity profile of 293T cells transduced with AAV2-MeCP2 for four days at a dose of 30,000 gc/cell.

FIG. 3A shows mouse primary cortical neurons were transduced at AAV vector doses ranging from 1E3-1E5 vg/cell including AAV-GFP as a control. FIG. 3B shows Western blot analysis of hMeCP2-myc expression in neurons 5 days after infection with 3E4 vector genomes (dose)/cell. FIG. 3C shows miR-132 expression in response to AAV2-MeCP2 re-delivery.

FIG. 4A shows wild-type post-natal day 1 mice injected via the facial vein with AAV encoding the e1 isoform of human MeCP2 containing 0, 1×, 2×, or 3× miR-132 target sequences. Wild-type animals were euthanized 3 months following injection and whole brain, heart and liver tissue was subjected to total RNA extraction, cDNA synthesis and qRT-PCR using primers specific to the e1 isoform of human MeCP2. Data were normalized to AAV-MeCP2 containing 3× miR-132 target sequences, which was set to 1. FIG. 4B shows gene expression analysis of human MeCP2 isoform e1 in brain of wild-type mice following intracranial injection of AAV-MeCP2. FIG. 4C shows gene expression analysis of human MeCP2 isoform e1 in brain of wild-type mice following intracranial injection of AAV-MeCP2.

DETAILED DESCRIPTION

Figure 1A:
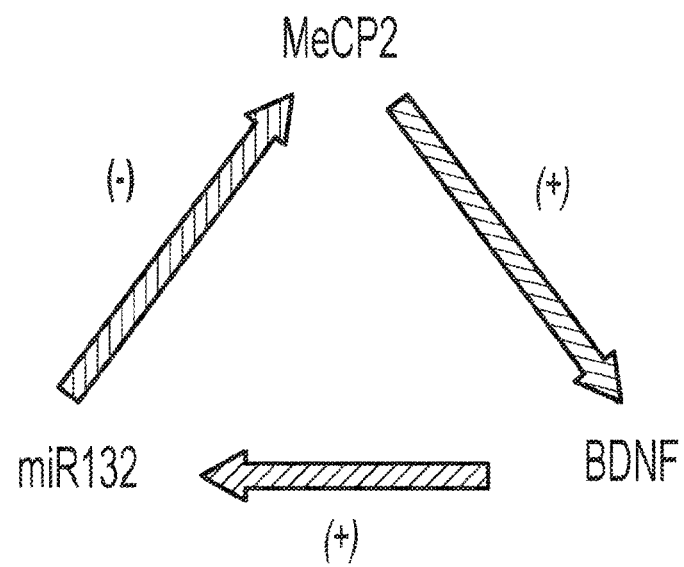
FIGS. 1A-1B show characterization of new AAV-MeCP2 vectors for safe and effective gene therapy in Rett syndrome.

Aspects of the disclosure relate, in part, to AAV vectors capable of self-regulating transgene (e.g., MeCP2) expression levels to prevent overexpression related toxicity. In some embodiments, the self-regulating mechanism is based on the presence of multiple copies of a miRNA regulatory element (e.g., one or more miR-132 binding sites) in the 3'UTR of the transgene cassette. As described further in the Examples section, AAV vectors capable of self-regulating transgene expression, in some embodiments, have an improved efficacy and safety profile compared to other AAV vectors, for example AAV vectors comprising native transgene promoters only. It should be recognized that the observations described in the Examples section in the context of miR-132/MeCP2 constructs is applicable to other transgene expression constructs comprising binding sites of other miRs that regulate protein expression (e.g., through a negative feedback loop).

In some embodiments, delivery routes that are most likely to mediate global gene delivery to the CNS (e.g., systemic injection and intrathecal injection) are likely to result in high level transduction of peripheral organs where transgene (e.g., MeCP2) expression may become toxic. The disclosure is based, in part, on the recognition that combining miRNA regulatory elements (MREs), such as miRNA binding sites (e.g., miR-122 binding sites and miR-1 binding sites), with MREs associated with negative feedback loops regulating protein expression (e.g., miR-132 binding sites for MeCP2), simultaneously regulate transgene expression levels and de-target transgene expression in peripheral organs.

Accordingly in some aspects, the disclosure provides a method of engineering a transgene, the method comprising: selecting a first gene encoding a first product in a cell; selecting an miRNA, the expression of which is positively regulated by the first product in the cell; and, engineering a transgene that expresses a transcript having a coding region encoding the first product and one or more binding sites for the miRNA. In some embodiments, the one or more binding sites for the miRNA are located in a 3'-non-coding region of the transcript.

In some aspects, the disclosure provides a method of engineering a transgene, the method comprising: selecting a first gene encoding a first product in a cell; selecting a second gene encoding a second product in the cell; determining that expression of the second product is positively regulated by the first product in the cell; selecting an miRNA; determining that expression of the miRNA is positively regulated by the second product in the cell; and, engineering a transgene to express in the cell a transcript having a coding region encoding the first product and one or more binding sites for the miRNA. In some embodiments, the one or more binding sites for the miRNA are located in a 3'-non-coding region of the transcript.

As used herein, "engineering a transgene" refers to production (e.g., synthesis) of a recombinant nucleic acid using gene cloning techniques, such as polymerase chain reaction (PCR), restriction enzyme digestion, and in vitro nucleic acid ligation, for example as described in Sambrook et al, Molecular Cloning: A Laboratory Manual, Cold Spring Harbor Press, Cold Spring Harbor, N.Y.

As used herein, a "product" or "gene product" refers to a nucleic acid (e.g., RNA transcript, dsRNA, miRNA, etc.), a peptide, protein, or polypeptide that is transcribed and/or translated from a nucleic acid (e.g., DNA or RNA) sequence. In some embodiments, a product is an RNA transcript comprising a protein coding region. In some embodiments, a protein coding region encodes a protein associated with a disease caused by a loss of function mutation (e.g., MeCP2). Additional examples of proteins associated with a disease caused by a loss of function mutation include but are not limited to tyrosinase (Tyrosinemia), lysosomal acid beta-galactosidase (GM1-gangliosidosis), beta-hexosaminidase A and B (Tay-Sach and Sandhoff disease), aspartoacylase (ASPA; Canavan disease), Aspartylglucosamininidase (Aspartylglucosaminuria), Palmitoyl protein thioesterase (Infantile Batten disease), tripeptidyl peptidase (Late infantile Batten disease), α-Galactosidase (Fabry disease), α-Fucosidase (Fucosidosis), Protective protein/cathepsin A (Galactosialidosis), β-Glucosidase (Gaucher disease), Galactosylceramidase (Globoid-cell leukodystrophy), α-Mannosidase (α-Mannosidosis), Arylsulfatase A (Metachromatic leukodystrophy), α-L-Iduronidase (Mucopolysaccharidosis I), α-N-acetylglucosaminidase (Mucopolysaccharidosis IIIB), Arylsulfatase B (Mucopolysaccharidosis VI), β-Glucuronidase (Mucopolysaccharidosis VII), Acid sphingomyelinase (Nieman-Pick disease), α-Glucosidase (Pompe disease) and Acid lipase (Wolman disease), FOXG1 (FOXG1 Syndrome), CDKL5, N-GlyI, Glut-1 (De Vivo disease), etc.

In some embodiments, a product is an interfering nucleic acid, for example a miRNA that regulates expression or activity of a gene product.

In some embodiments, one product regulates gene expression or protein expression of a second product. Regulation of gene product expression or translation can be positive or negative. "Positive regulation" refers to an increase of gene expression or activity (e.g., as a result of the expression or activity of another gene product). "Negative regulation" refers to a decrease or inhibition of gene expression or activity (e.g., as a result of the expression or activity of another gene product through a feedback loop).

In some embodiments, gene products such as growth factors, transcription factors (e.g., as described in Wang et al. Nucleic Acids Res. 2010 January; 38 (Database issue): D119-D122), etc. are capable of regulating transgene expression or activity in a cell or subject. Examples of growth factors include neurotrophins, such as brain-derived neurotrophic factor (BDNF), nerve growth factor (NGF), neurotrophin 3, neurotrophin 4, glial derived neurotrophic factor (GDNF), ciliary neurotrophic factor (CNTF), fibroblast growth factors (FGF1 to 23), neurturin, insulin-like growth factor 1 (IGF-1), insulin-like growth factor 2 (IGF-2), etc.

In some embodiments, transgenes as described by the disclosure are engineered to comprise at least one miRNA regulatory element (e.g., miRNA binding site) that is associated with a gene expression regulatory loop (e.g., negative feedback loops, positive feedback loops, etc.). Generally, gene expression regulatory loops may be endogenous to a cell, or artificial (e.g., one or more elements of the feedback loop are provided along with a transgene). In one example of a negative feedback loop, expression of MeCP2 in a cell causes an increase of brain-derived neurotrophic factor (BDNF) in the cell, which in turn increases expression of miR-132, which in turn regulates MeCP2 expression (FIG. 1). It should be appreciated that, in some embodiments, the disclosure relates to positive feedback loops, which may be used to amplify transgene expression.

In some embodiments, transgenes as described by the disclosure are engineered to comprise at least one miRNA regulatory element (e.g., miRNA binding site) that de-targets expression of the transgene from one or more non-target tissues. As used herein, "non-target tissue" refers to a tissue (e.g., cells of a tissue) in which expression of the transgene is undesirable. For example, in some embodiments, overexpression of MeCP2 in a cell results in hepatic cytotoxicity; in that context, liver tissue (e.g., liver cells) are a non-target tissue. In some embodiments, a non-target tissue is liver (e.g., liver cells), heart (e.g., heart cells), pancreas (e.g., pancreatic cells), muscle (e.g., muscle cells), immune cell (e.g., antigen presenting cells, etc.), or any combination thereof.

As used herein, "target tissue" refers to a tissue (e.g., cells of a tissue) in which expression of a transgene is preferred relative to other tissues, such as non-target tissues. In some embodiments, a target tissue is CNS tissue (e.g., CNS cells, such as neurons). Non-limiting examples of CNS tissue include brain tissue (e.g., neurons, glial cells, etc.) and spinal cord tissue.

Generally, the one or more miRNA binding sites of a transcript encoded by a transgene are located in the 3' untranslated region (3'UTR) of the transcript. In some embodiments, the one or more miRNA binding sites are located between the last codon of the coding region of the transcript and the poly-A tail of the transcript. However, it should be appreciated that, in some embodiments, one or more miRNA binding sites are located in a region other than the 3'UTR of the transcript, for example in an intron at the 5'-end of the transcript. The number of miRNA binding sites engineered into a transgene as described by the disclosure will vary depending upon the gene product encoded by the transgene, and may be determined empirically by a skilled artisan without an undue amount of experimentation. For example, in some embodiments a transgene as described by the disclosure comprises 1, 2, 3, 4, 5, 6, 7, 8, 9, or 10 miRNA binding sites. In some embodiments a transgene as described by the disclosure comprises more than 10 (e.g., any integer between 11 and 100) miRNA binding sites. In some embodiments, a transgene as described by the disclosure comprises 3, 4, or 5 miRNA binding sites. The one or more miRNA binding sites may each bind the same miRNA, or different miRNA. In some embodiments, a transgene as described by the disclosure comprises one or more (e.g. 3) miR-122 binding site(s), one or more (e.g., 3) miR-1 binding site(s), and three miR-132 binding sites.

Recombinant Nucleic Acids

In some embodiments, a transgene as described by the disclosure is encoded by a recombinant nucleic acid. A "nucleic acid" sequence refers to a DNA or RNA sequence. In some embodiments, proteins and nucleic acids of the disclosure are isolated. As used herein, the term "isolated" means artificially produced. As used herein with respect to nucleic acids, the term "isolated" means: (i) amplified in vitro by, for example, polymerase chain reaction (PCR); (ii) recombinantly produced by cloning; (iii) purified, as by cleavage and gel separation; or (iv) synthesized by, for example, chemical synthesis. An isolated nucleic acid is one which is readily manipulable by recombinant DNA techniques well known in the art. Thus, a nucleotide sequence contained in a vector in which 5' and 3' restriction sites are known or for which polymerase chain reaction (PCR) primer sequences have been disclosed is considered isolated but a nucleic acid sequence existing in its native state in its natural host is not. An isolated nucleic acid may be substantially purified, but need not be. For example, a nucleic acid that is isolated within a cloning or expression vector is not pure in that it may comprise only a tiny percentage of the material in the cell in which it resides. Such a nucleic acid is isolated, however, as the term is used herein because it is readily manipulable by standard techniques known to those of ordinary skill in the art. As used herein with respect to proteins or peptides, the term "isolated" refers to a protein or peptide that has been isolated from its natural environment or artificially produced (e.g., by chemical synthesis, by recombinant DNA technology, etc.).

The skilled artisan will also realize that conservative amino acid substitutions may be made to provide functionally equivalent variants, or homologs of the capsid proteins. In some aspects the disclosure embraces sequence alterations that result in conservative amino acid substitutions. As used herein, a conservative amino acid substitution refers to an amino acid substitution that does not alter the relative charge or size characteristics of the protein in which the amino acid substitution is made. Variants can be prepared according to methods for altering polypeptide sequence known to one of ordinary skill in the art such as are found in references that compile such methods, e.g., Molecular Cloning: A Laboratory Manual, J. Sambrook, et al., eds., Second Edition, Cold Spring Harbor Laboratory Press, Cold Spring Harbor, N.Y., 1989, or Current Protocols in Molecular Biology, F. M. Ausubel, et al., eds., John Wiley & Sons, Inc., New York. Conservative substitutions of amino acids include substitutions made among amino acids within the following groups: (a) M, I, L, V; (b) F, Y, W; (c) K, R, H; (d) A, G; (e) S, T; (f) Q, N; and (g) E, D. Therefore, one can make conservative amino acid substitutions to the amino acid sequence of the proteins and polypeptides disclosed herein.

In some embodiments, a nucleic acid as described by the disclosure is contained within a vector. As used herein, the term "vector" includes any genetic element, such as a plasmid, phage, transposon, cosmid, chromosome, artificial chromosome, virus, virion, etc., which is capable of replication when associated with the proper control elements and which can transfer gene sequences between cells. Thus, the term includes cloning and expression vehicles, as well as viral vectors. Examples of viral vectors include adenovirus vector, adeno-associated virus (AAV) vector, lentiviral vectors, herpesvirus vectors, baculovirus vectors, etc.

MeCP2

In some aspects, the disclosure relates to compositions and methods for expressing MeCP2 protein in a cell or subject. "MeCP2" refers to methyl CpG binding protein 2, which is encoded by the MeCP2 gene and plays important roles (e.g., functions as a transcriptional repressor, or transcriptional activator) in nerve cells, such as mature neurons. One example of a MeCP2 gene is represented by GenBank Accession Number NM_001110792 (MeCP2-e1). Another example of a MeCP2 gene is represented by GenBank Accession Number NM_001110792 (MeCP2-e2). The MeCP2 gene encodes two isoforms of MeCP2 protein, referred to as MeCP2 isoform e1 and MeCP2 isoform e2, which differ in the length of their N-terminus. In some embodiments, MeCP2 isoform e1 is represented by a sequence set forth in SEQ ID NO: 1. In some embodiments, MeCP2 isoform e2 is represented by a sequence set forth in SEQ ID NO: 2.

In some embodiments, a transgene (e.g., a recombinant nucleic acid) encodes a functional fragment of MeCP2 protein (e.g., a fragment of isoform e1 or isoform e2). A "functional fragment" of MeCP2 is a truncated MeCP2 protein that retains the natural function (e.g., transcriptional activator or transcriptional repressor) of wild-type (e.g., full-length) MeCP2 protein. In some embodiments, a functional fragment of MeCP2 comprises 1, 2, 3, 4, 5, 6, 7, 8, 9, 10, or more amino acid truncations relative to full-length MeCP2 protein. In some embodiments, a functional fragment of MeCP2 comprises between about 1 and 10, 5 and 50, 20 and 100 amino acid truncations relative to full-length MeCP2 protein.

In some embodiments, a transgene (e.g., a recombinant nucleic acid) encodes a variant of MeCP2 protein (e.g., a variant of isoform e1 or isoform e2). A variant of MeCP2 protein may have between about 50% and about 99.9% identity to a wild-type MeCP2 protein (e.g., SEQ ID NO: 1 or SEQ ID NO: 2). In some embodiments, a MeCP2 variant has about 50%, about 60%, about 70%, about 80%, about 90%, about 95%, or about 99% identity with a wild-type MeCP2 protein (e.g., SEQ ID NO: 1 or SEQ ID NO: 2).

miRNA and miRNA Binding Sites

The disclosure is based, in part, on the recognition that combining miRNA regulatory elements (MREs), such as miRNA binding sites (e.g., miR-122 binding sites and miR-1 binding sites), with MREs associated with negative feedback loops regulating protein expression (e.g., miR-132 binding sites for MeCP2), simultaneously regulate transgene expression levels and de-target transgene expression in peripheral organs.

miRNAs and other small interfering nucleic acids regulate gene expression via target RNA transcript cleavage/degradation or translational repression of the target messenger RNA (mRNA). miRNAs are natively expressed, typically as final 19-25 non-translated RNA products. miRNAs exhibit their activity through sequence-specific interactions with the 3' untranslated regions (UTR) of target mRNAs. These endogenously expressed miRNAs form hairpin precursors which are subsequently processed into a miRNA duplex, and further into a "mature" single stranded miRNA molecule. This mature miRNA guides a multiprotein complex, miRISC, which identifies target site, e.g., in the 3' UTR regions, of target mRNAs based upon their complementarity to the mature miRNA.

The following non-limiting list of miRNA genes, and their homologues, are useful in methods and compositions of the disclosure (e.g., for mediating self-regulated expression or de-targeting of a transgene): hsa-let-7a, hsa-let-7a*, hsa-let-7b, hsa-let-7b*, hsa-let-7c, hsa-let-7c*, hsa-let-7d, hsa-let-7d*, hsa-let-7e, hsa-let-7e*, hsa-let-7f, hsa-let-7f, hsa-let-7f-1*, hsa-let-7f-2*, hsa-let-7g, hsa-let-7g*, hsa-let-7i, hsa-let-7i*, hsa-miR-1, hsa-miR-100, hsa-miR-100*, hsa-miR-101, hsa-miR-101*, hsa-miR-103, hsa-miR-105, hsa-miR-105*, hsa-miR-106a, hsa-miR-106a*, hsa-miR-106b, hsa-miR-106b*, hsa-miR-107, hsa-miR-10a, hsa-miR-10a*, hsa-miR-10b, hsa-miR-10b*, hsa-miR-1178, hsa-miR-1179, hsa-miR-1180, hsa-miR-1181, hsa-miR-1182, hsa-miR-1183, hsa-miR-1184, hsa-miR-1185, hsa-miR-1197, hsa-miR-1200, hsa-miR-1201, hsa-miR-1202, hsa-miR-1203, hsa-miR-1204, hsa-miR-1205, hsa-miR-1206, hsa-miR-1207-3p, hsa-miR-1207-5p, hsa-miR-1208, hsa-miR-122, hsa-miR-122*, hsa-miR-1224-3p, hsa-miR-1224-5p, hsa-miR-1225-3p, hsa-miR-1225-5p, hsa-miR-1226, hsa-miR-1226*, hsa-miR-1227, hsa-miR-1228, hsa-miR-1228*, hsa-miR-1229, hsa-miR-1231, hsa-miR-1233, hsa-miR-1234, hsa-miR-1236, hsa-miR-1237, hsa-miR-1238, hsa-miR-124, hsa-miR-124*, hsa-miR-1243, hsa-miR-1244, hsa-miR-1245, hsa-miR-1246, hsa-miR-1247, hsa-miR-1248, hsa-miR-1249, hsa-miR-1250, hsa-miR-1251, hsa-miR-1252, hsa-miR-1253, hsa-miR-1254, hsa-miR-1255a, hsa-miR-1255b, hsa-miR-1256, hsa-miR-1257, hsa-miR-1258, hsa-miR-1259, hsa-miR-125a-3p, hsa-miR-125a-5p, hsa-miR-125b, hsa-miR-125b-1*, hsa-miR-125b-2*, hsa-miR-126, hsa-miR-126*, hsa-miR-1260, hsa-miR-1261, hsa-miR-1262, hsa-miR-1263, hsa-miR-1264, hsa-miR-1265, hsa-miR-1266, hsa-miR-1267, hsa-miR-1268, hsa-miR-1269, hsa-miR-1270, hsa-miR-1271, hsa-miR-1272, hsa-miR-1273, hsa-miR-127-3p, hsa-miR-1274a, hsa-miR-1274b, hsa-miR-1275, hsa-miR-127-5p, hsa-miR-1276, hsa-miR-1277, hsa-miR-1278, hsa-miR-1279, hsa-miR-128, hsa-miR-1280, hsa-miR-1281, hsa-miR-1282, hsa-miR-1283, hsa-miR-1284, hsa-miR-1285, hsa-miR-1286, hsa-miR-1287, hsa-miR-1288, hsa-miR-1289, hsa-miR-129*, hsa-miR-1290, hsa-miR-1291, hsa-miR-1292, hsa-miR-1293, hsa-miR-129-3p, hsa-miR-1294, hsa-miR-1295, hsa-miR-129-5p, hsa-miR-1296, hsa-miR-1297, hsa-miR-1298, hsa-miR-1299, hsa-miR-1300, hsa-miR-1301, hsa-miR-1302, hsa-miR-1303, hsa-miR-1304, hsa-miR-1305, hsa-miR-1306, hsa-miR-1307, hsa-miR-1308, hsa-miR-130a, hsa-miR-130a*, hsa-miR-130b, hsa-miR-130b*, hsa-miR-132, hsa-miR-132*, hsa-miR-1321, hsa-miR-1322, hsa-miR-1323, hsa-miR-1324, hsa-miR-133a, hsa-miR-133b, hsa-miR-134, hsa-miR-135a, hsa-miR-135a*, hsa-miR-135b, hsa-miR-135b*, hsa-miR-136, hsa-miR-136*, hsa-miR-137, hsa-miR-138, hsa-miR-138-1*, hsa-miR-138-2*, hsa-miR-139-3p, hsa-miR-139-5p, hsa-miR-140-3p, hsa-miR-140-5p, hsa-miR-141, hsa-miR-141*, hsa-miR-142-3p, hsa-miR-142-5p, hsa-miR-143, hsa-miR-143*, hsa-miR-144, hsa-miR-144*, hsa-miR-145, hsa-miR-145*, hsa-miR-146a, hsa-miR-146a*, hsa-miR-146b-3p, hsa-miR-146b-5p, hsa-miR-147, hsa-miR-147b, hsa-miR-148a, hsa-miR-148a*, hsa-miR-148b, hsa-miR-148b*, hsa-miR-149, hsa-miR-149*, hsa-miR-150, hsa-miR-150*, hsa-miR-151-3p, hsa-miR-151-5p, hsa-miR-152, hsa-miR-153, hsa-miR-154, hsa-miR-154*, hsa-miR-155, hsa-miR-155*, hsa-miR-15a, hsa-miR-15a*, hsa-miR-15b, hsa-miR-15b*, hsa-miR-16, hsa-miR-16-1*, hsa-miR-16-2*, hsa-miR-17, hsa-miR-17*, hsa-miR-181a, hsa-miR-181a*, hsa-miR-181a-2*, hsa-miR-181b, hsa-miR-181c, hsa-miR-181c*, hsa-miR-181d, hsa-miR-182, hsa-miR-182*, hsa-miR-1825, hsa-miR-1826, hsa-miR-1827, hsa-miR-183, hsa-miR-183*, hsa-miR-184, hsa-miR-185, hsa-miR-185*, hsa-miR-186, hsa-miR-186*, hsa-miR-187, hsa-miR-187*, hsa-miR-188-3p, hsa-miR-188-5p, hsa-miR-18a, hsa-miR-18a*, hsa-miR-18b, hsa-miR-18b*, hsa-miR-190, hsa-miR-190b, hsa-miR-191, hsa-miR-191*, hsa-miR-192, hsa-miR-192*, hsa-miR-193a-3p, hsa-miR-193a-5p, hsa-miR-193b, hsa-miR-193b*, hsa-miR-194, hsa-miR-194*, hsa-miR-195, hsa-miR-195*, hsa-miR-196a, hsa-miR-196a*, hsa-miR-196b, hsa-miR-197, hsa-miR-198, hsa-miR-199a-3p, hsa-miR-199a-5p, hsa-miR-199b-5p, hsa-miR-19a, hsa-miR-19a*, hsa-miR-19b, hsa-miR-19b-1*, hsa-miR-19b-2*, hsa-miR-200a, hsa-miR-200a*, hsa-miR-200b, hsa-miR-200b*, hsa-miR-200c, hsa-miR-200c*, hsa-miR-202, hsa-miR-202*, hsa-miR-203, hsa-miR-204, hsa-miR-205, hsa-miR-206, hsa-miR-208a, hsa-miR-208b, hsa-miR-20a, hsa-miR-20a*, hsa-miR-20b, hsa-miR-20b*, hsa-miR-21, hsa-miR-21*, hsa-miR-210, hsa-miR-211, hsa-miR-212, hsa-miR-214, hsa-miR-214*, hsa-miR-215, hsa-miR-216a, hsa-miR-216b, hsa-miR-217, hsa-miR-218, hsa-miR-218-1*, hsa-miR-218-2*, hsa-miR-219-1-3p, hsa-miR-219-2-3p, hsa-miR-219-5p, hsa-miR-22, hsa-miR-22*, hsa-miR-220a, hsa-miR-220b, hsa-miR-220c, hsa-miR-221, hsa-miR-221*, hsa-miR-222, hsa-miR-222*, hsa-miR-223, hsa-miR-223*, hsa-miR-224, hsa-miR-23a, hsa-miR-23a*, hsa-miR-23b, hsa-miR-23b*, hsa-miR-24, hsa-miR-24-1*, hsa-miR-24-2*, hsa-miR-25, hsa-miR-25*, hsa-miR-26a, hsa-miR-26a-1*, hsa-miR-26a-2*, hsa-miR-26b, hsa-miR-26b*, hsa-miR-27a, hsa-miR-27a*, hsa-miR-27b, hsa-miR-27b*, hsa-miR-28-3p, hsa-miR-28-5p, hsa-miR-296-3p, hsa-miR-296-5p, hsa-miR-297, hsa-miR-298, hsa-miR-299-3p, hsa-miR-299-5p, hsa-miR-29a, hsa-miR-29a*, hsa-miR-29b, hsa-miR-29b-1*, hsa-miR-29b-2*, hsa-miR-29c, hsa-miR-29c*, hsa-miR-300, hsa-miR-301a, hsa-miR-301b, hsa-miR-302a, hsa-miR-302a*, hsa-miR-302b, hsa-miR-302b*, hsa-miR-302c, hsa-miR-302c*, hsa-miR-302d, hsa-miR-302d*, hsa-miR-302e, hsa-miR-302f, hsa-miR-30a, hsa-miR-30a*, hsa-miR-30b, hsa-miR-30b*, hsa-miR-30c, hsa-miR-30c-1*, hsa-miR-30c-2*, hsa-miR-30d, hsa-miR-30d*, hsa-miR-30e, hsa-miR-30e*, hsa-miR-31, hsa-miR-31*, hsa-miR-32, hsa-miR-32*, hsa-miR-320a, hsa-miR-320b, hsa-miR-320c, hsa-miR-320d, hsa-miR-323-3p, hsa-miR-323-5p, hsa-miR-324-3p, hsa-miR-324-5p, hsa-miR-325, hsa-miR-326, hsa-miR-328, hsa-miR-329, hsa-miR-330-3p, hsa-miR-330-5p, hsa-miR-331-3p, hsa-miR-331-5p, hsa-miR-335, hsa-miR-335*, hsa-miR-337-3p, hsa-miR-337-5p, hsa-miR-338-3p, hsa-miR-338-5p, hsa-miR-339-3p, hsa-miR-339-5p, hsa-miR-33a, hsa-miR-33a*, hsa-miR-33b, hsa-miR-33b*, hsa-miR-340, hsa-miR-340*, hsa-miR-342-3p, hsa-miR-342-5p, hsa-miR-345, hsa-miR-346, hsa-miR-34a, hsa-miR-34a*, hsa-miR-34b, hsa-miR-34b*, hsa-miR-34c-3p, hsa-miR-34c-5p, hsa-miR-361-3p, hsa-miR-361-5p, hsa-miR-362-3p, hsa-miR-362-5p, hsa-miR-363, hsa-miR-363*, hsa-miR-365, hsa-miR-367, hsa-miR-367*, hsa-miR-369-3p, hsa-miR-369-5p, hsa-miR-370, hsa-miR-371-3p, hsa-miR-371-5p, hsa-miR-372, hsa-miR-373, hsa-miR-373*, hsa-miR-374a, hsa-miR-374a*, hsa-miR-374b, hsa-miR-374b*, hsa-miR-375, hsa-miR-376a, hsa-miR-376a*, hsa-miR-376b, hsa-miR-376c, hsa-miR-377, hsa-miR-377*, hsa-miR-378, hsa-miR-378*, hsa-miR-379, hsa-miR-379*, hsa-miR-380, hsa-miR-380*, hsa-miR-381, hsa-miR-382, hsa-miR-383, hsa-miR-384, hsa-miR-409-3p, hsa-miR-409-5p, hsa-miR-410, hsa-miR-411, hsa-miR-411*, hsa-miR-412, hsa-miR-421, hsa-miR-422a, hsa-miR-423-3p, hsa-miR-423-5p, hsa-miR-424, hsa-miR-424*, hsa-miR-425, hsa-miR-425*, hsa-miR-429, hsa-miR-431, hsa-miR-431*, hsa-miR-432, hsa-miR-432*, hsa-miR-433, hsa-miR-448, hsa-miR-449a, hsa-miR-449b, hsa-miR-450a, hsa-miR-450b-3p, hsa-miR-450b-5p, hsa-miR-451, hsa-miR-452, hsa-miR-452*, hsa-miR-453, hsa-miR-454, hsa-miR-454*, hsa-miR-455-3p, hsa-miR-455-5p, hsa-miR-483-3p, hsa-miR-483-5p, hsa-miR-484, hsa-miR-485-3p, hsa-miR-485-5p, hsa-miR-486-3p, hsa-miR-486-5p, hsa-miR-487a, hsa-miR-487b, hsa-miR-488, hsa-miR-488*, hsa-miR-489, hsa-miR-490-3p, hsa-miR-490-5p, hsa-miR-491-3p, hsa-miR-491-5p, hsa-miR-492, hsa-miR-493, hsa-miR-493*, hsa-miR-494, hsa-miR-495, hsa-miR-496, hsa-miR-497, hsa-miR-497*, hsa-miR-498, hsa-miR-499-3p, hsa-miR-499-5p, hsa-miR-500, hsa-miR-500*, hsa-miR-501-3p, hsa-miR-501-5p, hsa-miR-502-3p, hsa-miR-502-5p, hsa-miR-503, hsa-miR-504, hsa-miR-505, hsa-miR-505*, hsa-miR-506, hsa-miR-507, hsa-miR-508-3p, hsa-miR-508-5p, hsa-miR-509-3-5p, hsa-miR-509-3p, hsa-miR-509-5p, hsa-miR-510, hsa-miR-511, hsa-miR-512-3p, hsa-miR-512-5p, hsa-miR-513a-3p, hsa-miR-513a-5p, hsa-miR-513b, hsa-miR-513c, hsa-miR-514, hsa-miR-515-3p, hsa-miR-515-5p, hsa-miR-516a-3p, hsa-miR-516a-5p, hsa-miR-516b, hsa-miR-517*, hsa-miR-517a, hsa-miR-517b, hsa-miR-517c, hsa-miR-518a-3p, hsa-miR-518a-5p, hsa-miR-518b, hsa-miR-518c, hsa-miR-518c*, hsa-miR-518d-3p, hsa-miR-518d-5p, hsa-miR-518e, hsa-miR-518e*, hsa-miR-518f, hsa-miR-518f*, hsa-miR-519a, hsa-miR-519b-3p, hsa-miR-519c-3p, hsa-miR-519d, hsa-miR-519e, hsa-miR-519e*, hsa-miR-520a-3p, hsa-miR-520a-5p, hsa-miR-520b, hsa-miR-520c-3p, hsa-miR-520d-3p, hsa-miR-520d-5p, hsa-miR-520e, hsa-miR-520f, hsa-miR-520g, hsa-miR-520h, hsa-miR-521, hsa-miR-522, hsa-miR-523, hsa-miR-524-3p, hsa-miR-524-5p, hsa-miR-525-3p, hsa-miR-525-5p, hsa-miR-526b, hsa-miR-526b*, hsa-miR-532-3p, hsa-miR-532-5p, hsa-miR-539, hsa-miR-541, hsa-miR-541*, hsa-miR-542-3p, hsa-miR-542-5p, hsa-miR-543, hsa-miR-544, hsa-miR-545, hsa-miR-545*, hsa-miR-548a-3p, hsa-miR-548a-5p, hsa-miR-548b-3p, hsa-miR-548b-5p, hsa-miR-548c-3p, hsa-miR-548c-5p, hsa-miR-548d-3p, hsa-miR-548d-5p, hsa-miR-548e, hsa-miR-548f, hsa-miR-548g, hsa-miR-548h, hsa-miR-548i, hsa-miR-548j, hsa-miR-548k, hsa-miR-548l, hsa-miR-548m, hsa-miR-548n, hsa-miR-548o, hsa-miR-548p, hsa-miR-549, hsa-miR-550, hsa-miR-550*, hsa-miR-551a, hsa-miR-551b, hsa-miR-551b*, hsa-miR-552, hsa-miR-553, hsa-miR-554, hsa-miR-555, hsa-miR-556-3p, hsa-miR-556-5p, hsa-miR-557, hsa-miR-558, hsa-miR-559, hsa-miR-561, hsa-miR-562, hsa-miR-563, hsa-miR-564, hsa-miR-566, hsa-miR-567, hsa-miR-568, hsa-miR-569, hsa-miR-570, hsa-miR-571, hsa-miR-572, hsa-miR-573, hsa-miR-574-3p, hsa-miR-574-5p, hsa-miR-575, hsa-miR-576-3p, hsa-miR-576-5p, hsa-miR-577, hsa-miR-578, hsa-miR-579, hsa-miR-580, hsa-miR-581, hsa-miR-582-3p, hsa-miR-582-5p, hsa-miR-583, hsa-miR-584, hsa-miR-585, hsa-miR-586, hsa-miR-587, hsa-miR-588, hsa-miR-589, hsa-miR-589*, hsa-miR-590-3p, hsa-miR-590-5p, hsa-miR-591, hsa-miR-592, hsa-miR-593, hsa-miR-593*, hsa-miR-595, hsa-miR-596, hsa-miR-597, hsa-miR-598, hsa-miR-599, hsa-miR-600, hsa-miR-601, hsa-miR-602, hsa-miR-603, hsa-miR-604, hsa-miR-605, hsa-miR-606, hsa-miR-607, hsa-miR-608, hsa-miR-609, hsa-miR-610, hsa-miR-611, hsa-miR-612, hsa-miR-613, hsa-miR-614, hsa-miR-615-3p, hsa-miR-615-5p, hsa-miR-616, hsa-miR-616*, hsa-miR-617, hsa-miR-618, hsa-miR-619, hsa-miR-620, hsa-miR-621, hsa-miR-622, hsa-miR-623, hsa-miR-624, hsa-miR-624*, hsa-miR-625, hsa-miR-625*, hsa-miR-626, hsa-miR-627, hsa-miR-628-3p, hsa-miR-628-5p, hsa-miR-629, hsa-miR-629*, hsa-miR-630, hsa-miR-631, hsa-miR-632, hsa-miR-633, hsa-miR-634, hsa-miR-635, hsa-miR-636, hsa-miR-637, hsa-miR-638, hsa-miR-639, hsa-miR-640, hsa-miR-641, hsa-miR-642, hsa-miR-643, hsa-miR-644, hsa-miR-645, hsa-miR-646, hsa-miR-647, hsa-miR-648, hsa-miR-649, hsa-miR-650, hsa-miR-651, hsa-miR-652, hsa-miR-653, hsa-miR-654-3p, hsa-miR-654-5p, hsa-miR-655, hsa-miR-656, hsa-miR-657, hsa-miR-658, hsa-miR-659, hsa-miR-660, hsa-miR-661, hsa-miR-662, hsa-miR-663, hsa-miR-663b, hsa-miR-664, hsa-miR-664*, hsa-miR-665, hsa-miR-668, hsa-miR-671-3p, hsa-miR-671-5p, hsa-miR-675, hsa-miR-7, hsa-miR-708, hsa-miR-708*, hsa-miR-7-1*, hsa-miR-7-2*, hsa-miR-720, hsa-miR-744, hsa-miR-744*, hsa-miR-758, hsa-miR-760, hsa-miR-765, hsa-miR-766, hsa-miR-767-3p, hsa-miR-767-5p, hsa-miR-768-3p, hsa-miR-768-5p, hsa-miR-769-3p, hsa-miR-769-5p, hsa-miR-770-5p, hsa-miR-802, hsa-miR-873, hsa-miR-874, hsa-miR-875-3p, hsa-miR-875-5p, hsa-miR-876-3p, hsa-miR-876-5p, hsa-miR-877, hsa-miR-877*, hsa-miR-885-3p, hsa-miR-885-5p, hsa-miR-886-3p, hsa-miR-886-5p, hsa-miR-887, hsa-miR-888, hsa-miR-888*, hsa-miR-889, hsa-miR-890, hsa-miR-891a, hsa-miR-891b, hsa-miR-892a, hsa-miR-892b, hsa-miR-9, hsa-miR-9*, hsa-miR-920, hsa-miR-921, hsa-miR-922, hsa-miR-923, hsa-miR-924, hsa-miR-92a, hsa-miR-92a-1*, hsa-miR-92a-2*, hsa-miR-92b, hsa-miR-92b*, hsa-miR-93, hsa-miR-93*, hsa-miR-933, hsa-miR-934, hsa-miR-935, hsa-miR-936, hsa-miR-937, hsa-miR-938, hsa-miR-939, hsa-miR-940, hsa-miR-941, hsa-miR-942, hsa-miR-943, hsa-miR-944, hsa-miR-95, hsa-miR-96, hsa-miR-96*, hsa-miR-98, hsa-miR-99a, hsa-miR-99a*, hsa-miR-99b, and hsa-miR-99b*.

In some embodiments, one or more binding sites of a construct as described by the disclosure (e.g., recombinant nucleic acid, AAV vector, rAAV, etc.) de-targets transgene expression from a cell of the immune system (e.g., an antigen presenting cell (APC)). In some embodiments, an miRNA that de-targets transgene expression from an immune cell (e.g., an antigen presenting cell) is referred to as an immune-associated miRNA. In some embodiments, an immune-associated miRNA is an miRNA expressed in immune cells that exhibits at least a 2-fold, 3-fold, 4-fold, 5-fold, 6-fold, 7-fold, 8-fold, 9-fold, 10-fold higher level of expression in an immune cell compared with a non-immune cell (e.g., a control cell, such as a HeLa cell, HEK293 cell, mesenchymal cell, etc.). In some embodiments, the cell of the immune system (immune cell) in which the immune-associated miRNA is expressed is a B cell, T cell, Killer T cell, Helper T cell, γδ T cell, dendritic cell, macrophage, monocyte, vascular endothelial cell. or other immune cell. In some embodiments, the cell of the immune system is a B cell expressing one or more of the following markers: B220, BLAST-2 (EBVCS), Bu-1, CD19, CD20 (L26), CD22, CD24, CD27, CD57, CD72, CD79a, CD79b, CD86, chB6, D8/17, FMC7, L26, M17, MUM-1, Pax-5 (BSAP), and PC47H. In some embodiments, the cell of the immune system is a T cell expressing one or more of the following markers: ART2, CD1a, CD1d, CD11b (Mac-1), CD134 (OX40), CD150, CD2, CD25 (interleukin 2 receptor alpha), CD3, CD38, CD4, CD45RO, CD5, CD7, CD72, CD8, CRTAM, FOXP3, FT2, GPCA, HLA-DR, HML-1, HT23A, Leu-22, Ly-2, Ly-m22, MICG, MRC OX 8, MRC OX-22, OX40, PD-1 (Programmed death-1), RT6, TCR (T cell receptor), Thy-1 (CD90), and TSA-2 (Thymic shared Ag-2). In some embodiments, an immune-associated miRNA is selected from: miR-15a, miR-16-1, miR-17, miR-18a, miR-19a, miR-19b-1, miR-20a, miR-21, miR-29a/b/c, miR-30b, miR-31, miR-34a, miR-92a-1, miR-106a, miR-125a/b, miR-142-3p, miR-146a, miR-150, miR-155, miR-181a, miR-223 and miR-424, miR-221, miR-222, let-7i, miR-148, and miR-152.

Recombinant AAV Vectors (rAAV Vectors)

"Recombinant AAV (rAAV) vectors" of the disclosure are typically composed of, at a minimum, a transgene and its regulatory sequences, and 5' and 3' AAV inverted terminal repeats (ITRs). It is this recombinant AAV vector which is packaged into a capsid protein and delivered to a selected target cell. In some embodiments, the transgene is a nucleic acid sequence, heterologous to the vector sequences, which encodes a polypeptide, protein, functional RNA molecule (e.g., gRNA) or other gene product, of interest. The nucleic acid coding sequence is operatively linked to regulatory components in a manner which permits transgene transcription, translation, and/or expression in a cell of a target tissue.

In some embodiments, the instant disclosure relates to a recombinant AAV (rAAV) vector comprising a nucleic acid sequence including a promoter operably linked to a transgene, wherein the transgene encodes a MeCP2 protein (e.g., MeCP2 isoform e1). In some embodiments, a rAAV vector further comprises nucleic acid sequences encoding one or more AAV inverted terminal repeat sequences (ITRs), for example AAV2 ITRs. In some embodiments, a rAAV vector further comprises nucleic acid sequences encoding one or more AAV ITRs selected from the group consisting of AAV3, AAV4, AAV5, and AAV6. In some embodiments, ITRs are artificial sequences that replace ITR function, for example as disclosed in WO/2016/172008.

The AAV sequences of the vector typically comprise the cis-acting 5' and 3' inverted terminal repeat sequences (See, e.g., B. J. Carter, in "Handbook of Parvoviruses", ed., P. Tijsser, CRC Press, pp. 155 168 (1990)). The ITR sequences are about 145 bp in length. Preferably, substantially the entire sequences encoding the ITRs are used in the molecule, although some degree of minor modification of these sequences is permissible. The ability to modify these ITR sequences is within the skill of the art. (See, e.g., texts such as Sambrook et al, "Molecular Cloning. A Laboratory Manual", 2d ed., Cold Spring Harbor Laboratory, New York (1989); and K. Fisher et al., J Virol., 70:520 532 (1996)). An example of such a molecule employed in the present disclosure is a "cis-acting" plasmid containing the transgene, in which the selected transgene sequence and associated regulatory elements are flanked by the 5' and 3' AAV ITR sequences. The AAV ITR sequences may be obtained from any known AAV, including presently identified mammalian AAV types (e.g., AAV2, AAV3, AAV4, AAV5, or AAV6 ITR sequences).

In addition to the major elements identified above for the recombinant AAV vector, the vector also includes control elements necessary which are operably linked to the transgene in a manner which permits its transcription, translation and/or expression in a cell transfected with the plasmid vector or infected with the virus produced by the disclosure. As used herein, "operably linked" sequences include both expression control sequences that are contiguous with the gene of interest and expression control sequences that act in trans or at a distance to control the gene of interest.

Expression control sequences include appropriate transcription initiation, termination, promoter and enhancer sequences; efficient RNA processing signals such as splicing and polyadenylation (polyA) signals; sequences that stabilize cytoplasmic mRNA; sequences that enhance translation efficiency (i.e., Kozak consensus sequence); sequences that enhance protein stability; and when desired, sequences that enhance secretion of the encoded product. A great number of expression control sequences, including promoters which are native, constitutive, inducible and/or tissue-specific, are known in the art and may be utilized.

As used herein, a nucleic acid sequence (e.g., coding sequence) and regulatory sequences are said to be "operably" linked when they are covalently linked in such a way as to place the expression or transcription of the nucleic acid sequence under the influence or control of the regulatory sequences. If it is desired that the nucleic acid sequences be translated into a functional protein, two DNA sequences are said to be operably linked if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably linked to a nucleic acid sequence if the promoter region were capable of effecting transcription of that DNA sequence such that the resulting transcript might be translated into the desired protein or polypeptide. Similarly two or more coding regions are operably linked when they are linked in such a way that their transcription from a common promoter results in the expression of two or more proteins having been translated in frame. In some embodiments, operably linked coding sequences yield a fusion protein. In some embodiments, operably linked coding sequences yield a functional RNA (e.g., gRNA, miRNA).

For nucleic acids encoding proteins, a polyadenylation sequence generally is inserted following the transgene sequences and before the 3' AAV ITR sequence. A rAAV construct useful in the present disclosure may also contain an intron, desirably located between the promoter/enhancer sequence and the transgene. One possible intron sequence is derived from SV-40, and is referred to as the SV-40 T intron sequence. Another vector element that may be used is an internal ribosome entry site (IRES). An IRES sequence is used to produce more than one polypeptide from a single gene transcript. An IRES sequence would be used to produce a protein that contain more than one polypeptide chains. Selection of these and/or other vector elements may be performed, as appropriate, and many such sequences are available [see, e.g., Sambrook et al, and references cited therein at, for example, pages 3.18 3.26 and 16.17 16.27 and Ausubel et al., Current Protocols in Molecular Biology, John Wiley & Sons, New York, 1989]. In some embodiments, a Foot and Mouth Disease Virus 2A sequence is included in polyprotein; this is a small peptide (approximately 18 amino acids in length) that has been shown to mediate the cleavage of polyproteins (Ryan, M D et al., EMBO, 1994; 4: 928-933; Mattion, N M et al., J Virology, November 1996; p. 8124-8127; Furler, S et al., Gene Therapy, 2001; 8: 864-873; and Halpin, C et al., The Plant Journal, 1999; 4: 453-459). The cleavage activity of the 2A sequence has previously been demonstrated in artificial systems including plasmids and gene therapy vectors (AAV and retroviruses) (Ryan, M D et al., EMBO, 1994; 4: 928-933; Mattion, N M et al., J Virology, November 1996; p. 8124-8127; Furler, S et al., Gene Therapy, 2001; 8: 864-873; and Halpin, C et al., The Plant Journal, 1999; 4: 453-459; de Felipe, P et al., Gene Therapy, 1999; 6: 198-208; de Felipe, P et al., Human Gene Therapy, 2000; 11: 1921-1931.; and Klump, H et al., Gene Therapy, 2001; 8: 811-817).

The precise nature of the regulatory sequences needed for gene expression in host cells may vary between species, tissues or cell types, but shall in general include, as necessary, 5' non-transcribed and 5' non-translated sequences involved with the initiation of transcription and translation respectively, such as a TATA box, capping sequence, CAAT sequence, enhancer elements, and the like. Especially, such 5' non-transcribed regulatory sequences will include a promoter region that includes a promoter sequence for transcriptional control of the operably joined gene. Regulatory sequences may also include enhancer sequences or upstream activator sequences as desired. The vectors of the disclosure may optionally include 5' leader or signal sequences. The choice and design of an appropriate vector is within the ability and discretion of one of ordinary skill in the art.

Examples of constitutive promoters include, without limitation, the retroviral Rous sarcoma virus (RSV) LTR promoter (optionally with the RSV enhancer), the cytomegalovirus (CMV) promoter (optionally with the CMV enhancer) [see, e.g., Boshart et al, Cell, 41:521-530 (1985)], the SV40 promoter, the dihydrofolate reductase promoter, the β-actin promoter, the phosphoglycerol kinase (PGK) promoter, and the EF1α promoter [Invitrogen]. In some embodiments, a promoter is an enhanced chicken β-actin promoter.

Inducible promoters allow regulation of gene expression and can be regulated by exogenously supplied compounds, environmental factors such as temperature, or the presence of a specific physiological state, e.g., acute phase, a particular differentiation state of the cell, or in replicating cells only. Inducible promoters and inducible systems are available from a variety of commercial sources, including, without limitation, Invitrogen, Clontech and Ariad. Many other systems have been described and can be readily selected by one of skill in the art. Examples of inducible promoters regulated by exogenously supplied promoters include the zinc-inducible sheep metallothionine (MT) promoter, the dexamethasone (Dex)—inducible mouse mammary tumor virus (MMTV) promoter, the T7 polymerase promoter system (WO 98/10088); the ecdysone insect promoter (No et al, Proc. Natl. Acad. Sci. USA, 93:3346-3351 (1996)), the tetracycline-repressible system (Gossen et al, Proc. Natl. Acad. Sci. USA, 89:5547-5551 (1992)), the tetracycline-inducible system (Gossen et al, Science, 268:1766-1769 (1995), see also Harvey et al, Curr. Opin. Chem. Biol., 2:512-518 (1998)), the RU486-inducible system (Wang et al, Nat. Biotech., 15:239-243 (1997) and Wang et al, Gene Ther., 4:432-441 (1997)) and the rapamycin-inducible system (Magari et al, J. Clin. Invest., 100:2865-2872 (1997)). Still other types of inducible promoters which may be useful in this context are those which are regulated by a specific physiological state, e.g., temperature, acute phase, a particular differentiation state of the cell, or in replicating cells only.

In another embodiment, the native promoter for the transgene will be used. The native promoter may be preferred when it is desired that expression of the transgene should mimic the native expression. The native promoter may be used when expression of the transgene must be regulated temporally or developmentally, or in a tissue-specific manner, or in response to specific transcriptional stimuli. For example, in some embodiments, a native promoter is a MeCP2 promoter, such as a mouse MeCP2 promoter. In some embodiments, a mouse MeCP2 promoter is represented by a sequence set forth in SEQ ID NO: 3. In a further embodiment, other native expression control elements, such as enhancer elements, polyadenylation sites or Kozak consensus sequences may also be used to mimic the native expression.

In some embodiments, the regulatory sequences impart tissue-specific gene expression capabilities. In some cases, the tissue-specific regulatory sequences bind tissue-specific transcription factors that induce transcription in a tissue specific manner. Such tissue-specific regulatory sequences (e.g., promoters, enhancers, etc.) are well known in the art. Exemplary tissue-specific regulatory sequences include, but are not limited to the following tissue specific promoters: an eye-specific retinoschisin promoter or K12 promoter, a liver-specific thyroxin binding globulin (TBG) promoter, an insulin promoter, a glucagon promoter, a somatostatin promoter, a pancreatic polypeptide (PPY) promoter, a synapsin-1 (Syn) promoter, a creatine kinase (MCK) promoter, a mammalian desmin (DES) promoter, a α-myosin heavy chain (a-MHC) promoter, or a cardiac Troponin T (cTnT) promoter. Other exemplary promoters include Beta-actin promoter, hepatitis B virus core promoter, Sandig et al., Gene Ther., 3:1002-9 (1996); alpha-fetoprotein (AFP) promoter, Arbuthnot et al., Hum. Gene Ther., 7:1503-14 (1996)), bone osteocalcin promoter (Stein et al., Mol. Biol. Rep., 24:185-96 (1997)); bone sialoprotein promoter (Chen et al., J. Bone Miner. Res., 11:654-64 (1996)), CD2 promoter (Hansal et al., J. Immunol., 161:1063-8 (1998); immunoglobulin heavy chain promoter; T cell receptor α-chain promoter, neuronal such as neuron-specific enolase (NSE) promoter (Andersen et al., Cell. Mol. Neurobiol., 13:503-15 (1993)), neurofilament light-chain gene promoter (Piccioli et al., Proc. Natl. Acad. Sci. USA, 88:5611-5 (1991)), and the neuron-specific vgf gene promoter (Piccioli et al., Neuron, 15:373-84 (1995)), among others which will be apparent to the skilled artisan.

In some embodiments, one or more bindings sites for one or more of miRNAs are incorporated in a transgene of a rAAV vector, to inhibit the expression of the transgene in one or more tissues of a subject harboring the transgene. The skilled artisan will appreciate that binding sites may be selected to control the expression of a transgene in a tissue specific manner. For example, binding sites for the liver-specific miR-122 may be incorporated into a transgene to inhibit expression of that transgene in the liver. The target sites in the mRNA may be in the 5' UTR, the 3' UTR or in the coding region. Typically, the target site is in the 3' UTR of the mRNA. Furthermore, the transgene may be designed such that multiple miRNAs regulate the mRNA by recognizing the same or multiple sites. The presence of multiple miRNA binding sites may result in the cooperative action of multiple RISCs and provide highly efficient inhibition of expression. The target site sequence may comprise a total of 5-100, 10-60, or more nucleotides. The target site sequence may comprise at least 5 nucleotides of the sequence of a target gene binding site.

Recombinant Adeno-Associated Viruses (rAAVs)

In some aspects, the disclosure provides isolated AAVs. As used herein with respect to AAVs, the term "isolated" refers to an AAV that has been artificially produced or obtained. Isolated AAVs may be produced using recombinant methods. Such AAVs are referred to herein as "recombinant AAVs". Recombinant AAVs (rAAVs) preferably have tissue-specific targeting capabilities, such that a nuclease and/or transgene of the rAAV will be delivered specifically to one or more predetermined tissue(s). The AAV capsid is an important element in determining these tissue-specific targeting capabilities. Thus, an rAAV having a capsid appropriate for the tissue being targeted can be selected.

Methods for obtaining recombinant AAVs having a desired capsid protein are well known in the art. (See, for example, US 2003/0138772), the contents of which are incorporated herein by reference in their entirety). Typically the methods involve culturing a host cell which contains a nucleic acid sequence encoding an AAV capsid protein; a functional rep gene; a recombinant AAV vector composed of, AAV inverted terminal repeats (ITRs) and a transgene; and sufficient helper functions to permit packaging of the recombinant AAV vector into the AAV capsid proteins. In some embodiments, capsid proteins are structural proteins encoded by the cap gene of an AAV. AAVs comprise three capsid proteins, virion proteins 1 to 3 (named VP1, VP2 and VP3), all of which are transcribed from a single cap gene via alternative splicing. In some embodiments, the molecular weights of VP1, VP2 and VP3 are respectively about 87 kDa, about 72 kDa and about 62 kDa. In some embodiments, upon translation, capsid proteins form a spherical 60-mer protein shell around the viral genome. In some embodiments, the functions of the capsid proteins are to protect the viral genome, deliver the genome and interact with the host. In some aspects, capsid proteins deliver the viral genome to a host in a tissue specific manner.

In some embodiments, an rAAV described by the disclosure comprises one or more capsid proteins capable of crossing the blood-brain barrier. In some embodiments, the at least one capsid protein has a serotype selected from the group consisting of AAV1, AAV2, AAV2i8, AAV2.5, AAV6, AAV8, AAVrh8, AAV9, AAVrh10, AAV-B1, AAV9.45A-String (e.g., AAV9.45-AS), AAV9.45Angiopep, AAV9.47-Angiopep, and AAV9.47-AS. In some embodiments, the at least one capsid protein has a AAV-PHP.B serotype, for example as described in U.S. Pat. No. 9,585,971. In some embodiments, a capsid protein has a serotype as described in WO2015/127128, WO2016/054554, WO2016/054557, or WO2016/065001.

The components to be cultured in the host cell to package a rAAV vector in an AAV capsid may be provided to the host cell in trans. Alternatively, any one or more of the required components (e.g., recombinant AAV vector, rep sequences, cap sequences, and/or helper functions) may be provided by a stable host cell which has been engineered to contain one or more of the required components using methods known to those of skill in the art. Most suitably, such a stable host cell will contain the required component(s) under the control of an inducible promoter. However, the required component(s) may be under the control of a constitutive promoter. Examples of suitable inducible and constitutive promoters are provided herein, in the discussion of regulatory elements suitable for use with the transgene. In still another alternative, a selected stable host cell may contain selected component(s) under the control of a constitutive promoter and other selected component(s) under the control of one or more inducible promoters. For example, a stable host cell may be generated which is derived from 293 cells (which contain E1 helper functions under the control of a constitutive promoter), but which contain the rep and/or cap proteins under the control of inducible promoters. Still other stable host cells may be generated by one of skill in the art.

In some embodiments, the instant disclosure relates to a host cell containing a nucleic acid that comprises a coding sequence encoding a protein (e.g., MeCP2 protein, such as MeCP2 isoform e1). In some embodiments, the instant disclosure relates to a composition comprising the host cell described above. In some embodiments, the composition comprising the host cell above further comprises a cryopreservative.

The recombinant AAV vector, rep sequences, cap sequences, and helper functions required for producing the rAAV of the disclosure may be delivered to the packaging host cell using any appropriate genetic element (vector). The selected genetic element may be delivered by any suitable method, including those described herein. The methods used to construct any embodiment of this disclosure are known to those with skill in nucleic acid manipulation and include genetic engineering, recombinant engineering, and synthetic techniques. See, e.g., Sambrook et al., Molecular Cloning: A Laboratory Manual, Cold Spring Harbor Press, Cold Spring Harbor, N.Y. Similarly, methods of generating rAAV virions are well known and the selection of a suitable method is not a limitation on the present disclosure. See, e.g., K. Fisher et al., J. Virol., 70:520-532 (1993) and U.S. Pat. No. 5,478,745.

In some embodiments, recombinant AAVs may be produced using the triple transfection method (described in detail in U.S. Pat. No. 6,001,650). Typically, the recombinant AAVs are produced by transfecting a host cell with an recombinant AAV vector (comprising a transgene) to be packaged into AAV particles, an AAV helper function vector, and an accessory function vector. An AAV helper function vector encodes the "AAV helper function" sequences (i.e., rep and cap), which function in trans for productive AAV replication and encapsidation. Preferably, the AAV helper function vector supports efficient AAV vector production without generating any detectable wild-type AAV virions (i.e., AAV virions containing functional rep and cap genes). Non-limiting examples of vectors suitable for use with the present disclosure include pHLP19, described in U.S. Pat. No. 6,001,650 and pRep6cap6 vector, described in U.S. Pat. No. 6,156,303, the entirety of both incorporated by reference herein. The accessory function vector encodes nucleotide sequences for non-AAV derived viral and/or cellular functions upon which AAV is dependent for replication (i.e., "accessory functions"). The accessory functions include those functions required for AAV replication, including, without limitation, those moieties involved in activation of AAV gene transcription, stage specific AAV mRNA splicing, AAV DNA replication, synthesis of cap expression products, and AAV capsid assembly. Viral-based accessory functions can be derived from any of the known helper viruses such as adenovirus, herpesvirus (other than herpes simplex virus type-1), and vaccinia virus.

In some aspects, the disclosure provides transfected host cells. The term "transfection" is used to refer to the uptake of foreign DNA by a cell, and a cell has been "transfected" when exogenous DNA has been introduced inside the cell membrane. A number of transfection techniques are generally known in the art. See, e.g., Graham et al. (1973) Virology, 52:456, Sambrook et al. (1989) Molecular Cloning, a laboratory manual, Cold Spring Harbor Laboratories, New York, Davis et al. (1986) Basic Methods in Molecular Biology, Elsevier, and Chu et al. (1981) Gene 13:197. Such techniques can be used to introduce one or more exogenous nucleic acids, such as a nucleotide integration vector and other nucleic acid molecules, into suitable host cells.

A "host cell" refers to any cell that harbors, or is capable of harboring, a substance of interest. Often a host cell is a mammalian cell. A host cell may be used as a recipient of an AAV helper construct, an AAV minigene plasmid, an accessory function vector, or other transfer DNA associated with the production of recombinant AAVs. The term includes the progeny of the original cell which has been transfected. Thus, a "host cell" as used herein may refer to a cell which has been transfected with an exogenous DNA sequence. It is understood that the progeny of a single parental cell may not necessarily be completely identical in morphology or in genomic or total DNA complement as the original parent, due to natural, accidental, or deliberate mutation.

As used herein, the term "cell line" refers to a population of cells capable of continuous or prolonged growth and division in vitro. Often, cell lines are clonal populations derived from a single progenitor cell. It is further known in the art that spontaneous or induced changes can occur in karyotype during storage or transfer of such clonal populations. Therefore, cells derived from the cell line referred to may not be precisely identical to the ancestral cells or cultures, and the cell line referred to includes such variants.

As used herein, the terms "recombinant cell" refers to a cell into which an exogenous DNA segment, such as DNA segment that leads to the transcription of a biologically-active polypeptide or production of a biologically active nucleic acid such as an RNA, has been introduced.

As used herein, the term "vector" includes any genetic element, such as a plasmid, phage, transposon, cosmid, chromosome, artificial chromosome, virus, virion, etc., which is capable of replication when associated with the proper control elements and which can transfer gene sequences between cells. Thus, the term includes cloning and expression vehicles, as well as viral vectors. In some embodiments, useful vectors are contemplated to be those vectors in which the nucleic acid segment to be transcribed is positioned under the transcriptional control of a promoter. A "promoter" refers to a DNA sequence recognized by the synthetic machinery of the cell, or introduced synthetic machinery, required to initiate the specific transcription of a gene. The phrases "operatively positioned," "under control" or "under transcriptional control" means that the promoter is in the correct location and orientation in relation to the nucleic acid to control RNA polymerase initiation and expression of the gene. The term "expression vector or construct" means any type of genetic construct containing a nucleic acid in which part or all of the nucleic acid encoding sequence is capable of being transcribed. In some embodiments, expression includes transcription of the nucleic acid, for example, to generate a biologically-active polypeptide product or functional RNA (e.g., guide RNA) from a transcribed gene. The foregoing methods for packaging recombinant vectors in desired AAV capsids to produce the rAAVs of the disclosure are not meant to be limiting and other suitable methods will be apparent to the skilled artisan.

Administration Methods

Compositions described by the disclosure (e.g., recombinant nucleic acids, rAAVs, pharmaceutical compositions, etc.) may be delivered to a subject according to any appropriate methods known in the art. Compositions (e.g., recombinant nucleic acids, rAAVs, pharmaceutical compositions, etc.), preferably suspended in a physiologically compatible carrier (i.e., in a composition), may be administered to a subject, i.e. host animal, such as a human, mouse, rat, cat, dog, sheep, rabbit, horse, cow, goat, pig, guinea pig, hamster, chicken, turkey, or a non-human primate (e.g., Macaque). In some embodiments, a host animal does not include a human. In some embodiments, a subject is a human. In some embodiments, a subject is less than a year old, for example 1, 2, 3, 4, 5, 6, 7, 8, 9, 10, or 11 months old.

Delivery of the compositions to a mammalian subject may be by, for example, systemic injection (e.g., intravenous injection) or intrathecal injection. Additional methods of administering compositions to the CNS of a subject, for example intracranial injection, intrastriatal injection, etc. may also be used. Combinations of administration methods (e.g., topical administration and intrastromal injection) can also be used.

In some embodiments, the compositions of the disclosure may comprise an rAAV alone, or in combination with one or more other viruses (e.g., a second rAAV encoding having one or more different transgenes). In some embodiments, a composition comprises 1, 2, 3, 4, 5, 6, 7, 8, 9, 10, or more different rAAVs each having one or more different transgenes.

In some embodiments, a composition further comprises a pharmaceutically acceptable carrier. Suitable carriers may be readily selected by one of skill in the art in view of the indication for which the composition is directed. For example, one suitable carrier includes saline, which may be formulated with a variety of buffering solutions (e.g., phosphate buffered saline). Other exemplary carriers include sterile saline, lactose, sucrose, calcium phosphate, gelatin, dextran, agar, pectin, peanut oil, sesame oil, and water. The selection of the carrier is not a limitation of the present disclosure.

Optionally, the compositions of the disclosure may contain, in addition to the recombinant nucleic acid or rAAV and carrier(s), other pharmaceutical ingredients, such as preservatives, or chemical stabilizers. Suitable exemplary preservatives include chlorobutanol, potassium sorbate, sorbic acid, sulfur dioxide, propyl gallate, the parabens, ethyl vanillin, glycerin, phenol, and parachlorophenol. Suitable chemical stabilizers include gelatin and albumin.

The compositions are administered in sufficient amounts to transfect the cells of a desired tissue (e.g., CNS tissue) and to provide sufficient levels of gene transfer and expression without undue adverse effects. Examples of pharmaceutically acceptable routes of administration include, but are not limited to, direct delivery to the selected organ (e.g., intrastromal delivery to the eye), oral, inhalation (including intranasal and intratracheal delivery), intraocular, intravenous, intramuscular, subcutaneous, intradermal, intratumoral, and other parental routes of administration. Routes of administration may be combined, if desired.

The dose of rAAV virions required to achieve a particular "therapeutic effect," e.g., the units of dose in genome copies/per kilogram of body weight (GC/kg), will vary based on several factors including, but not limited to: the route of rAAV virion administration, the level of gene or RNA expression required to achieve a therapeutic effect, the specific disease or disorder being treated, and the stability of the gene or RNA product. One of skill in the art can readily determine a rAAV virion dose range to treat a patient having a particular disease or disorder based on the aforementioned factors, as well as other factors.

An effective amount of composition (e.g., recombinant nucleic acid, rAAV, pharmaceutical composition, etc.) is an amount sufficient to target infect an animal, target a desired tissue. In some embodiments, an effective amount of an rAAV is an amount sufficient to produce a stable somatic transgenic animal model. The effective amount will depend primarily on factors such as the species, age, weight, health of the subject, and the tissue to be targeted, and may thus vary among animal and tissue. For example, an effective amount of the rAAV is generally in the range of from about 1 ml to about 100 ml of solution containing from about $10^9$ to $10^{16}$ genome copies. In some cases, a dosage between about $10^{11}$ to $10^{13}$ rAAV genome copies is appropriate. In certain embodiments, $10^{10}$ or $10^{11}$ rAAV genome copies is effective to target CNS tissue (e.g., corneal tissue). In some cases, stable transgenic animals are produced by multiple doses of an rAAV.

In some embodiments, a dose of the composition is administered to a subject no more than once per calendar day (e.g., a 24-hour period). In some embodiments, a dose of the composition is administered to a subject no more than once per 2, 3, 4, 5, 6, or 7 calendar days. In some embodiments, a dose of the composition is administered to a subject no more than once per calendar week (e.g., 7 calendar days). In some embodiments, a dose of the composition is administered to a subject no more than bi-weekly (e.g., once in a two calendar week period). In some embodiments, a dose of the composition is administered to a subject no more than once per calendar month (e.g., once in 30 calendar days). In some embodiments, a dose of the composition is administered to a subject no more than once per six calendar months. In some embodiments, a dose of the composition is administered to a subject no more than once per calendar year (e.g., 365 days or 366 days in a leap year).

In some embodiments, compositions are formulated to reduce aggregation of AAV particles in the composition, particularly where high rAAV concentrations are present (e.g., ~$10^{13}$ GC/ml or more). Appropriate methods for reducing aggregation of may be used, including, for example, addition of surfactants, pH adjustment, salt concentration adjustment, etc. (See, e.g., Wright F R, et al., Molecular Therapy (2005) 12, 171-178, the contents of which are incorporated herein by reference.)

Formulation of pharmaceutically-acceptable excipients and carrier solutions is well-known to those of skill in the art, as is the development of suitable dosing and treatment regimens for using the particular compositions described herein in a variety of treatment regimens. Typically, these formulations may contain at least about 0.1% of the active compound or more, although the percentage of the active ingredient(s) may, of course, be varied and may conveniently be between about 1 or 2% and about 70% or 80% or more of the weight or volume of the total formulation. Naturally, the amount of active compound in each therapeutically-useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In some embodiments, compositions (e.g., recombinant nucleic acids, rAAVs, pharmaceutical compositions, etc.) in suitably formulated pharmaceutical compositions disclosed herein are delivered directly to target tissue, e.g., direct to CNS tissue (e.g., brain, spinal cord, etc.) However, in certain circumstances it may be desirable to separately or in addition deliver the compositions via another route, e.g., subcutaneously, intraopancreatically, intranasally, parenterally, intravenously, intramuscularly, intrathecally, or orally, intraperitoneally, or by inhalation. In some embodiments, the administration modalities as described in U.S. Pat. Nos. 5,543,158; 5,641,515 and 5,399,363 (each specifically incorporated herein by reference in its entirety) may be used to deliver rAAVs. In some embodiments, a preferred mode of administration is by intravenous injection.

The pharmaceutical forms suitable for injectable use include sterile aqueous solutions or dispersions and sterile powders for the extemporaneous preparation of sterile injectable solutions or dispersions. Dispersions may also be prepared in glycerol, liquid polyethylene glycols, and mixtures thereof and in oils. Under ordinary conditions of storage and use, these preparations contain a preservative to prevent the growth of microorganisms. In many cases the form is sterile and fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For administration of an injectable aqueous solution, for example, the solution may be suitably buffered, if necessary, and the liquid diluent first rendered isotonic with sufficient saline or glucose. These particular aqueous solutions are especially suitable for intravenous, intramuscular, subcutaneous and intraperitoneal administration. In this connection, a suitable sterile aqueous medium may be employed. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the host. The person responsible for administration will, in any event, determine the appropriate dose for the individual host.

Sterile injectable solutions are prepared by incorporating the compositions (e.g., recombinant nucleic acids, rAAVs, pharmaceutical compositions, etc.) in the required amount in the appropriate solvent with various of the other ingredients enumerated herein, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The compositions (e.g., recombinant nucleic acids, rAAVs, pharmaceutical compositions, etc.) disclosed herein may also be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug-release capsules, and the like.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Supplementary active ingredients can also be incorporated into the compositions. The phrase "pharmaceutically-acceptable" refers to molecular entities and compositions that do not produce an allergic or similar untoward reaction when administered to a host.

Delivery vehicles such as liposomes, nanocapsules, microparticles, microspheres, lipid particles, vesicles, and the like, may be used for the introduction of the compositions of the present disclosure into suitable host cells. In particular, the rAAV vector delivered transgenes may be formulated for delivery either encapsulated in a lipid particle, a liposome, a vesicle, a nanosphere, or a nanoparticle or the like.

Such formulations may be preferred for the introduction of pharmaceutically acceptable formulations of the nucleic acids or the rAAV constructs disclosed herein. The formation and use of liposomes is generally known to those of skill in the art. Recently, liposomes were developed with improved serum stability and circulation half-times (U.S. Pat. No. 5,741,516). Further, various methods of liposome and liposome like preparations as potential drug carriers have been described (U.S. Pat. Nos. 5,567,434; 5,552,157; 5,565,213; 5,738,868 and 5,795,587).

Liposomes have been used successfully with a number of cell types that are normally resistant to transfection by other procedures. In addition, liposomes are free of the DNA length constraints that are typical of viral-based delivery systems. Liposomes have been used effectively to introduce genes, drugs, radiotherapeutic agents, viruses, transcription factors and allosteric effectors into a variety of cultured cell lines and animals. In addition, several successful clinical trials examining the effectiveness of liposome-mediated drug delivery have been completed.

Liposomes are formed from phospholipids that are dispersed in an aqueous medium and spontaneously form multilamellar concentric bilayer vesicles (also termed multilamellar vesicles (MLVs). MLVs generally have diameters of from 25 nm to 4 μm. Sonication of MLVs results in the formation of small unilamellar vesicles (SUVs) with diameters in the range of 200 to 500 .ANG., containing an aqueous solution in the core.

Alternatively, nanocapsule formulations of the rAAV may be used. Nanocapsules can generally entrap substances in a stable and reproducible way. To avoid side effects due to intracellular polymeric overloading, such ultrafine particles (sized around 0.1 μm) should be designed using polymers able to be degraded in vivo. Biodegradable polyalkyl-cyanoacrylate nanoparticles that meet these requirements are contemplated for use.

Methods for Treating Rett Syndrome

In some aspects, the disclosure relates to compositions and methods for treating Rett Syndrome. Rett syndrome is a genetic neurological disorder caused by one or more loss of function mutations in the MeCP2 gene, for example as described in Suter et al. J Autism Dev Disord. 2014 March; 44(3): 703-711. In some embodiments, a subject having Rett syndrome has 1, 2, 3, 4, 5, 6, 7, 8, 9, 10, or more loss of function mutations in MeCP2 gene.

As used herein, the terms "treatment", "treating", and "therapy" refer to therapeutic treatment and prophylactic or preventative manipulations. The terms further include ameliorating existing symptoms, preventing additional symptoms, ameliorating or preventing the underlying causes of symptoms, preventing or reversing causes of symptoms, for example, symptoms associated with a disease caused by a loss of function mutation, for example Rett syndrome. Thus, the terms denote that a beneficial result has been conferred on a subject with a disorder (e.g., Rett syndrome), or with the potential to develop such a disorder. Furthermore, the term "treatment" is defined as the application or administration of an agent (e.g., therapeutic agent or a therapeutic composition) to a subject, or an isolated tissue or cell line from a subject, who may have a disease, a symptom of disease or a predisposition toward a disease, with the purpose to cure, heal, alleviate, relieve, alter, remedy, ameliorate, improve or affect the disease, the symptoms of disease or the predisposition toward disease.

Therapeutic agents or therapeutic compositions may include a compound in a pharmaceutically acceptable form that prevents and/or reduces the symptoms of a particular disease (e.g., Rett syndrome). For example a therapeutic composition may be a pharmaceutical composition that prevents and/or reduces the symptoms of Rett syndrome. It is contemplated that the therapeutic composition of the present invention will be provided in any suitable form. The form of the therapeutic composition will depend on a number of factors, including the mode of administration as described herein. The therapeutic composition may contain diluents, adjuvants and excipients, among other ingredients as described herein.

EXAMPLE

Example 1: Gene Expression Analysis of Human MeCP2 Isoform e1 In Vitro

Approximately 80% of Rett cases are caused by mutations in the X-linked gene encoding methyl CpG binding protein 2 (MeCP2), a widely expressed epigenetic regulator that is expressed at high levels in mature neurons. Most Rett patients carry a normal and mutant allele of MeCP2. Disease results from random X-chromosome inactivation where ~50% of neurons are MeCP2 deficient due to inactivation of the normal allele, whereas in the other ~50% of neurons the mutant allele is silenced and normal expression of wild type MeCP2 is retained. The heterogeneity of MeCP2 deficiency in the CNS has important implications for development of gene therapy approaches for Rett syndrome. In Rett mouse models, the reversibility of neurological phenotypes has been observed after restoration of normal MeCP2 expression in adults. In these transgenic experiments, restored MeCP2 expression was driven from its native genomic locus and activation was achieved in the majority of cells in the brain. However, somatic gene transfer has yet to replicate any of these successes.

Generally, MeCP2 has a very narrow window of safe expression levels, as patients with a duplication of the MeCP2 locus typically present delayed motor and cognitive development as well as severe intellectual impairment. Experiments in transgenic mouse models corroborate this notion, as ectopic expression of MeCP2 is toxic in wild-type animals, but safe and partially effective in ameliorating disease phenotypes of MeCP2-deficient mice when transgene expression starts during embryonic development. Notably, the MeCP2 gene is alternatively spliced to generate two proteins with different N termini, designated as MeCP2-e1 and MeCP2-e2. Patients with MeCP2 locus duplication overexpress both MeCP2 isoforms. Therefore, the symptoms in patients with MeCP2 locus duplication and results in transgenic mice may be explained by overexpression of the MeCP2-e2 isoform and timing of transgene expression during development.

Previous AAV9-MeCP2-e1 therapeutic experiments have been focused on neonatal intravascular (IV) or intracerebroventricular (ICV) delivery and in some instances have encountered lethal liver toxicity and hind limb clasping. Furthermore, the age of mice treated in such experiments does not necessarily correspond to that likely to be implemented in most Rett patients, which presumably would be treated after symptom onset (6-18 months). In humans, the primary phase of synaptogenesis occurs in the first 2 years and coincides with a rapid increase in non-CG DNA methylation in neurons, as well as the onset of symptoms in Rett patients. In mice, synaptogenesis occurs between 2 and 4 weeks of age. Therefore, it is critical to examine efficacy and potential toxicity of AAV-MeCP2 gene delivery at relevant developmental stages beyond post-natal day 0-1. Additionally, an important limitation to implementing systemic AAV gene delivery to treat CNS disorders is the transduction of organs other than the brain, such as liver, which is the organ with the highest AAV tropism in the body.

Figure 1B:
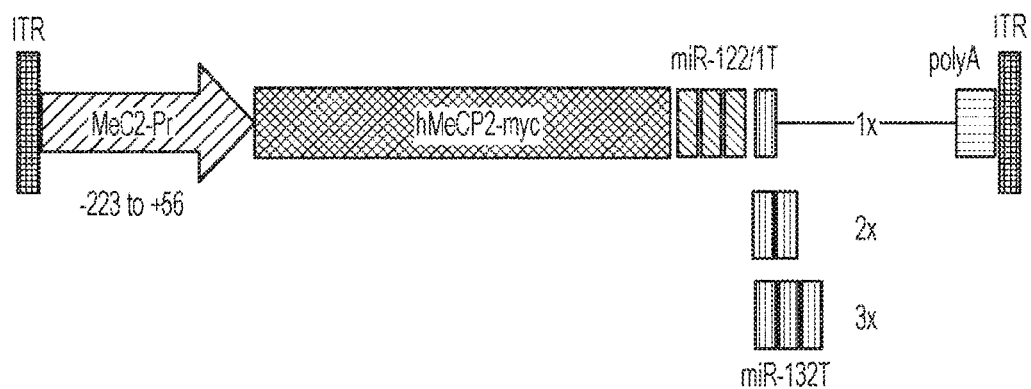

A series of new AAV-MeCP2 vectors that eliminate gene expression in peripheral organs and also self-regulate expression of MeCP2 were designed. Generally, MeCP2 mRNA carries either a short (1.8kb) or long (~10kb) 3'UTR, with the latter being the preferential isoform expression in brain. The MeCP2 mRNA constructs described in this example comprise an MeCP2 isoform-e1 protein coding sequence and several miRNA regulatory elements (MREs). It was observed that translation of MeCP2 in the CNS is regulated by miR-132 through a homeostatic mechanism involving changes in brain derived neurotrophic factor (BNDF) levels in response to MeCP2 expression (FIG. 1A). Based on this mechanism a series of AAV-MeCP2 vectors with increasing numbers of the miR-132 MREs (e.g., miR-132 binding sites) coupled to a fixed number of MREs for miR-1 and miR-122 (e.g., 3×-miR-1 and 3×-mir-122 binding sites) to de-target AAV gene expression from skeletal muscle and liver (FIG. 1B).

Figure 2A:
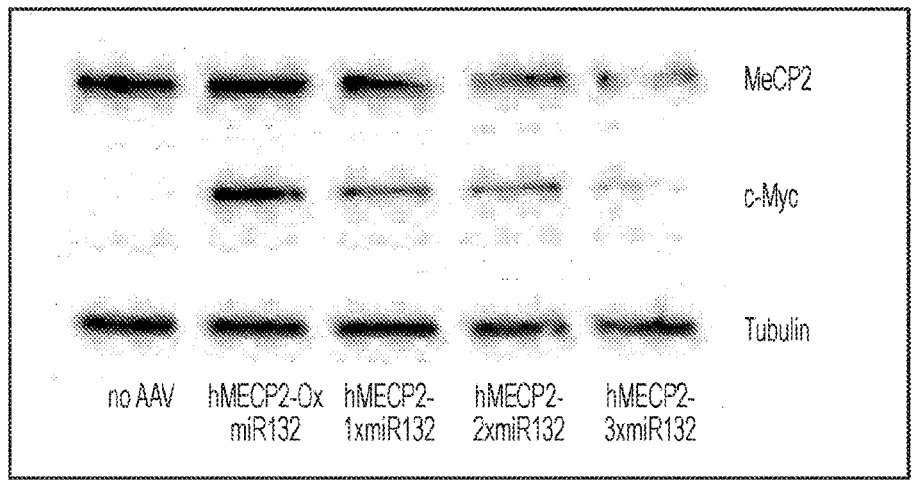
FIGS. 2A-2C show effective expression of AAV2-MeCP2 in HEK293T cells.
Figure 2B:
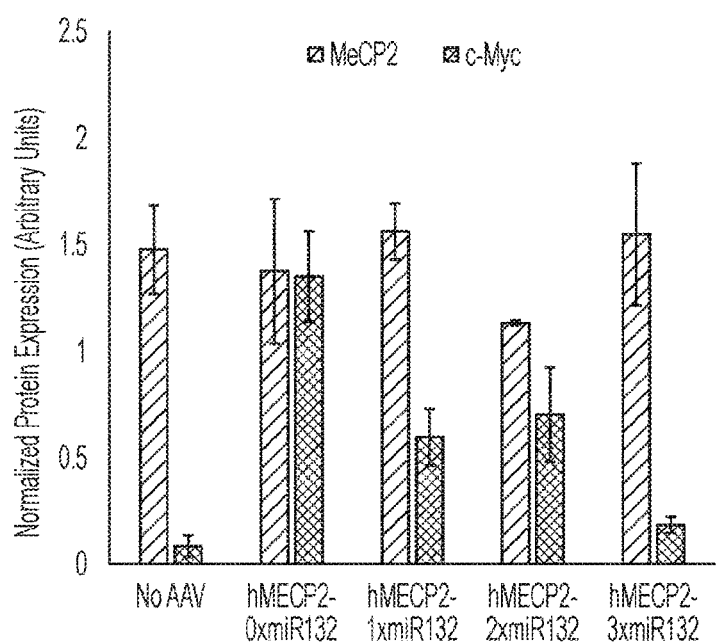
Figure 2C:
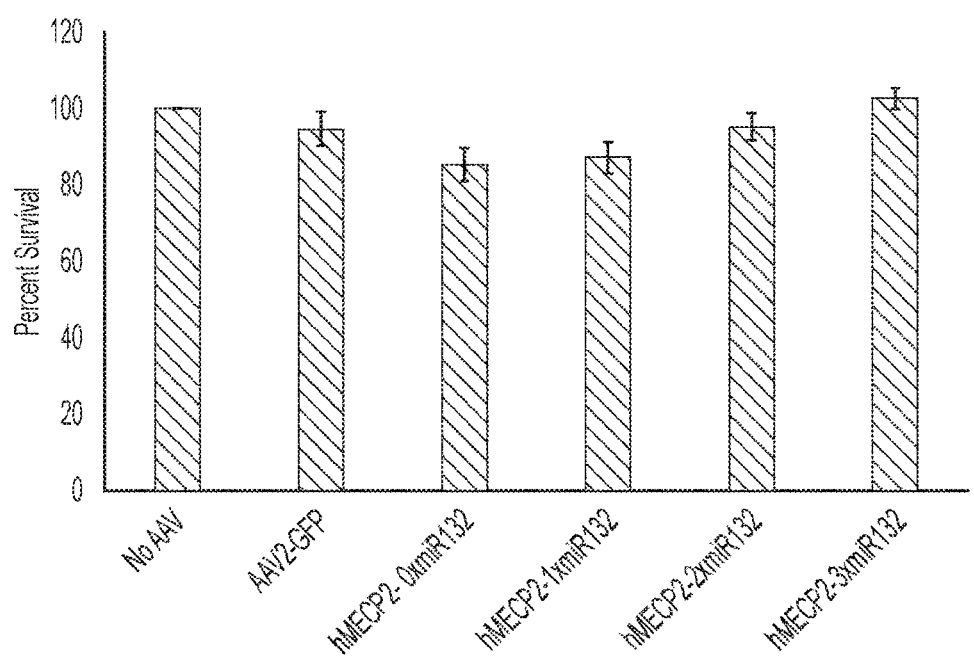

A series of in vitro experiments were carried out. Briefly, HEK293T cells were transfected with 30,000 gc/cell of AAV2-MeCP2 for four days. FIGS. 2A-2B show effective expression of AAV2-MeCP2 in HEK293T cells, as measured by Western blot (FIG. 2A) and normalized protein expression assay (FIG. 2B). FIG. 2C shows a toxicity profile of 293T cells transduced with AAV2-MeCP2 for four days at a dose of 30,000 gc/cell.

Figure 3A:
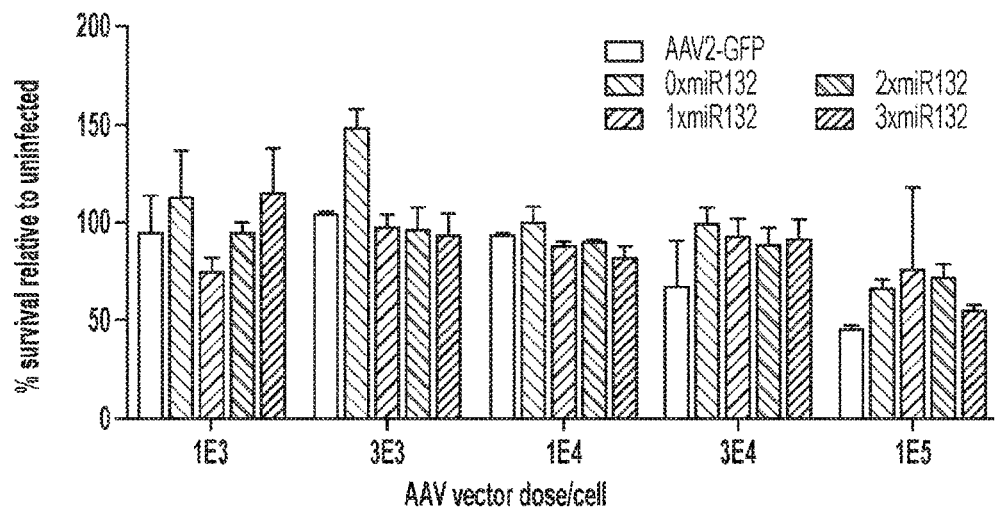
FIGS. 3A-3C show AAV2-MeCP2 expression in mouse cortical neurons.
Figure 3B:
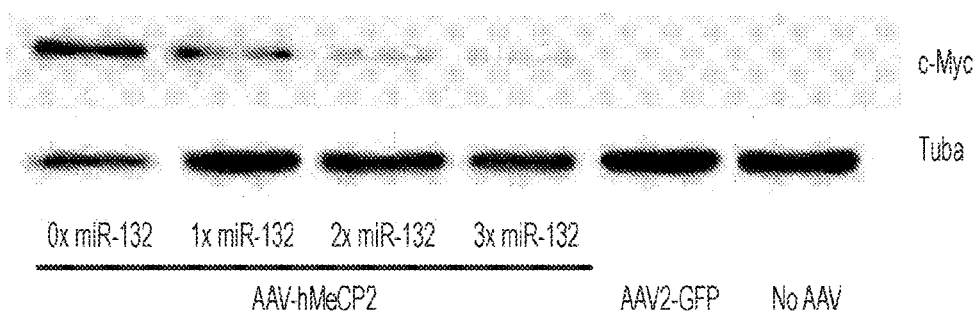
Figure 3C:
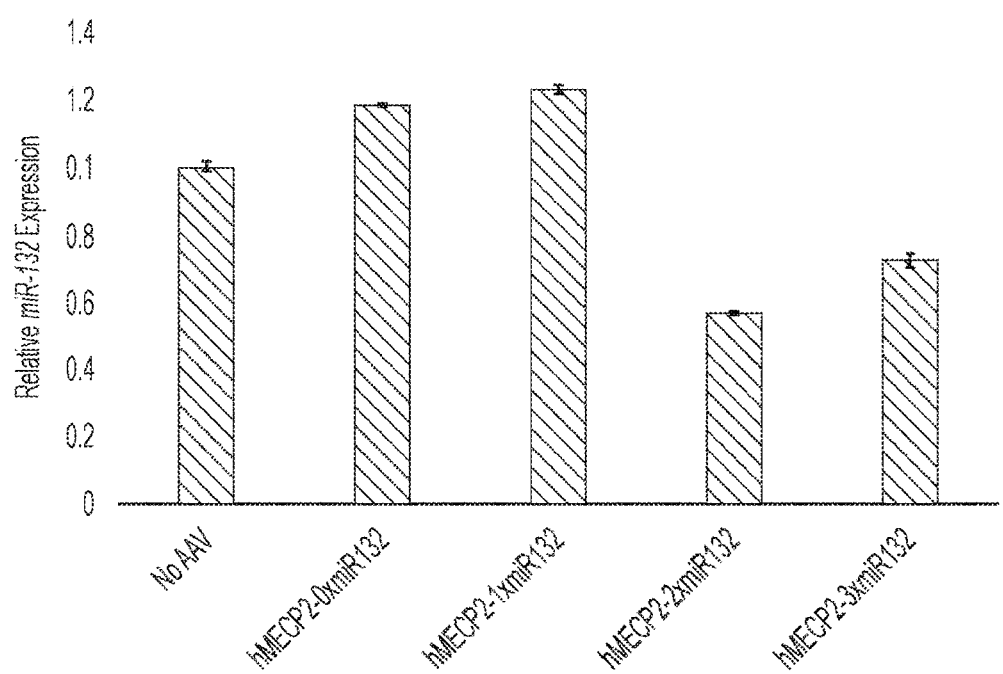

A dose response study in mouse primary cortical neurons showed comparable effects on cell survival for AAV-GFP and AAV-MeCP2 vectors (FIG. 3A), indicating that expression of myc-tagged human MeCP2 from a short mouse MeCP2 promoter (−223 to +56) is non-toxic to primary neurons in culture. In addition, it was observed that MeCP2-myc protein levels were inversely proportional to the number of miR-132 MREs (e.g., miR-132 binding sites) present in the MeCP2-myc transcript (FIG. 3B). FIG. 3C shows miR-132 expression in response to AAV2-MeCP2 five days after AAV infection.

Example 2: Gene Expression Analysis of Human MeCP2 Isoform e1 in Wild-Type Mice Following Systemic Delivery of AAV-MeCP2

Figure 4A:
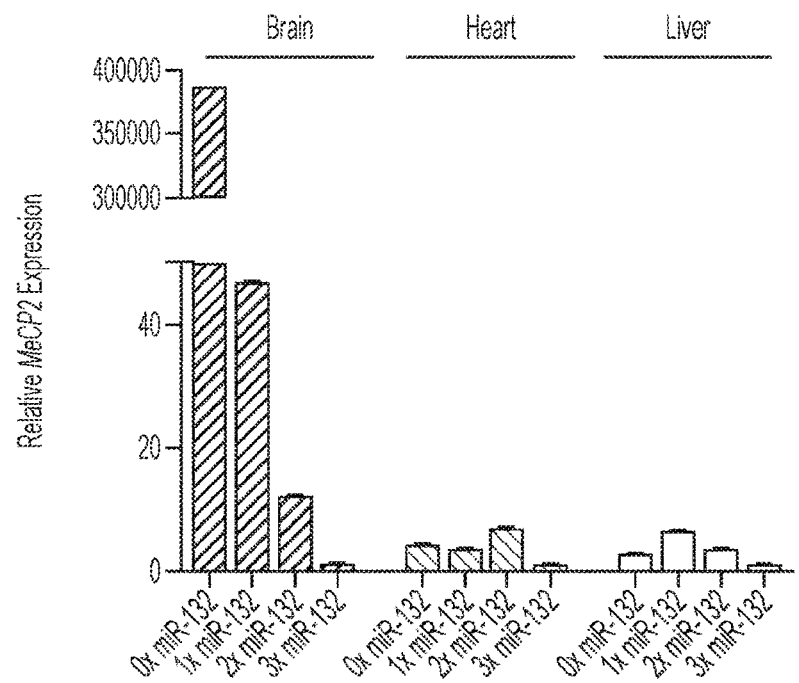
FIGS. 4A-4C show representative data obtained from in vivo mouse experiments.
Figure 4B:
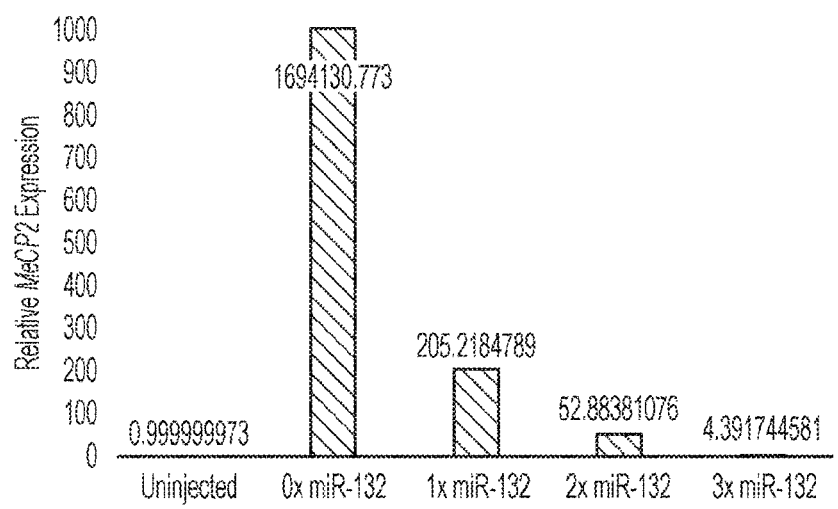
Figure 4C:
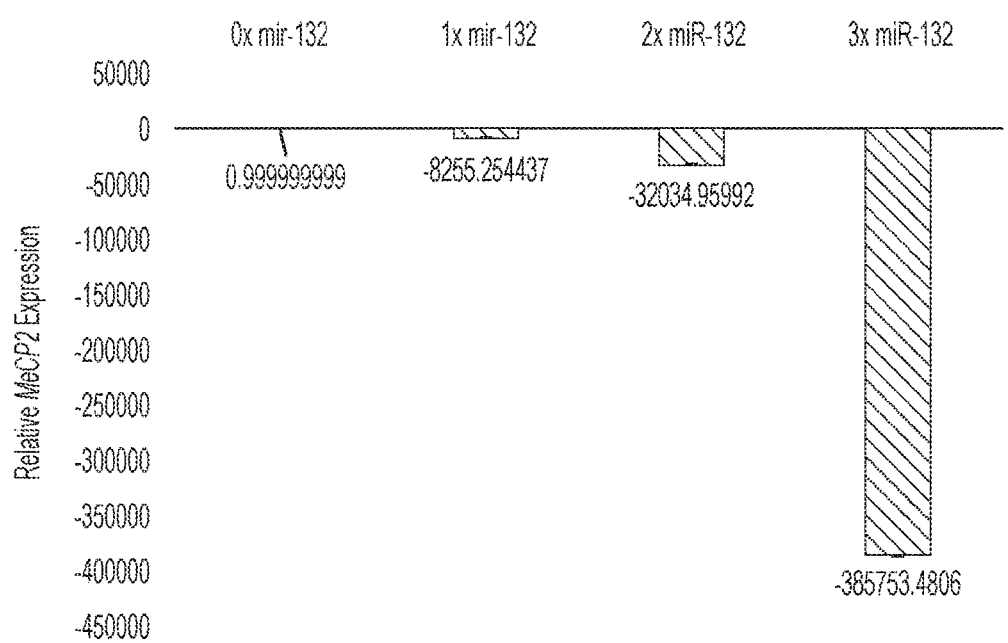

To extend the in vitro observations demonstrating the ability to titer MeCP2 levels by insertion of miR-132 target sequences described in Example 1, post-natal day 1 wild-type mice were injected via the facial vein (e.g., intracranial injection) with AAV encoding the e1 isoform of human MeCP2 containing 0, 1×, 2×, or 3× miR-132 target sequences. Gene expression analysis of brain tissue indicated that MeCP2 levels are inversely proportional to the number of miR132 target sequences (FIGS. 4A-4C).

Figure 5:
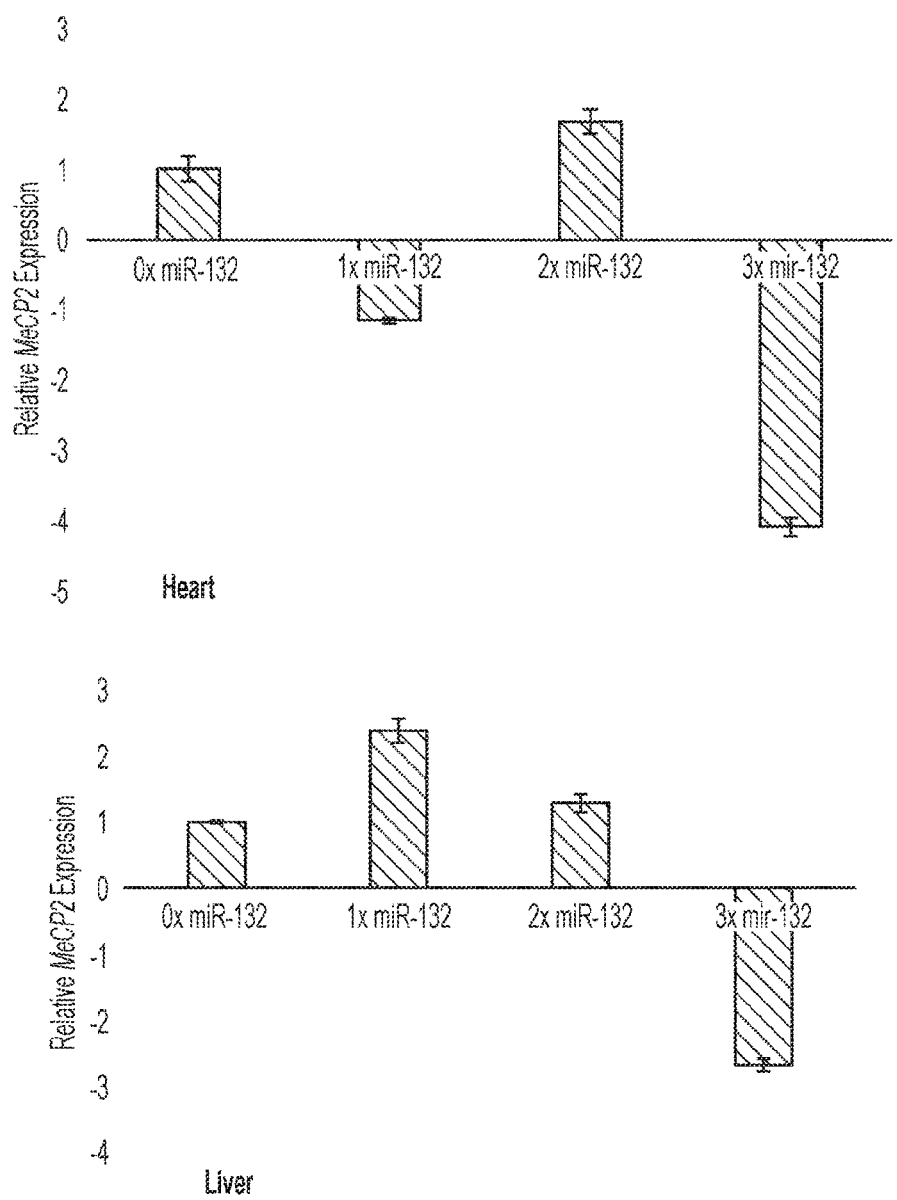
FIG. 5 shows MeCP2 expression driven by constructs described by the disclosure is effectively de-targeted from heart and liver.

In some embodiments, systemic administration of some AAV serotypes can transduce tissues outside of the central nervous system, and elevated expression of MeCP2 in liver, cardiac and skeletal tissues has been observed to be associated with detrimental physiological consequences. To minimize heart and liver transduction of MeCP2, AAV-MeCP2 vectors described by the disclosure contain at least one miR-1 (e.g., 3×-miR-1) and at least one miR-122 (e.g., 3×-miR-122) target sequence (e.g., binding sites) to de-target MeCP2 expression from the heart and liver, respectively. qRT-PCR analysis using primers against e2 human MeCP2 (which was undetectable), and e1 and e2 mouse MeCP2 (which did not change) were performed. Gene expression analysis of heart and liver tissue from wild-type animals indicated MeCP2 is effectively de-targeted from the heart and liver, as evidenced by substantially reduced expression compared to the brain (FIG. 4A and FIG. 5).

Example 3: Therapeutic Efficacy and Safety of Self-Regulating AAV-MeCP2 Vectors

Therapeutic efficacy and safety of AAV-MeCP2-e1 vectors is examined in mice. In some embodiments, AAV-PHP.B capsid protein is used, as this capsid has improved neuronal transduction efficiency. Mecp2-null mice (Mecp2$^{tm1.1Bird}$/J; Male$^{-/y}$ and female$^{+/-}$) at 4 weeks of age are treated by systemic administration of AAV-PHP.B-MeCP2-e1 vectors carrying different MRE cassettes (e.g., at vector doses of 1E11, 3E11, 1E12 vg/mouse) and body weight and phenotypic scores are monitored every two weeks. As controls, MeCP2/Mecp2$^{tm1.1Bird}$ mice injected with vehicle and wild type mice are used. A subset of mice in each cohort (n=8; 4 males and 4 females) are sacrificed at 8 weeks post-injection and MeCP2 expression quantified by western blot and compared across groups. Transduction efficiency in the brain is assessed by double immunofluorescence staining for MeCP2 and neurons (using the neuronal marker NeuN) and quantification of transduced neurons (MeCP2+, NeuN+) in cortex, striatum, thalamus, hippocampus and cerebellum is performed. The levels of PSD-95 are assessed by western blot and immunostaining of brain sections; PSD-95 is a key scaffold protein in synaptic maturation whose levels are decreased in brains from MeCP2-null mice.

To perform vector biodistribution analysis, genomic DNA is isolated from different regions of the CNS and peripheral organs and analyzed by digital PCR. Another subset of animals in each cohort (n=16; 8 males and 8 females) is used for survival and longitudinal analysis of behavioral (e.g., open field; social interaction) and motor performance (e.g., rotarod, grid walk) as well as whole body plethismography to assess breathing patterns and apnea characteristic of MeCP2-null mice. Endpoint studies are the same as at 8 weeks after treatment. Safety of the vectors is also assessed in wild type mice in a dose escalation study using doses identical to those indicated above with endpoints at 7, 30, 90 and 180 days to assess the CNS and peripheral tissues for evidence of toxicity. AAV vector biodistribution and MeCP2 expression are assessed as well.

Example 4: Characterization of Changes in the Genome/Transcriptome of Transduced Neurons after AAV-MeCP2 Gene Transfer at Different Stages of Nervous System Development A key aspect in the development of a safe and effective gene therapy approach for Rett is to characterize in detail the impact of de novo expression of MeCP2 on the epigenetic landscape and transcriptomic profile of transduced neurons. For this purpose, AAV-PHP.B-MeCP2-e1 vectors carrying an IRES-GFP cassette are produced, and allow isolation of transduced GFP+ cells from brain, cerebellum and spinal cord by either FACS or laser capture microdissection followed by whole genome bisulfite sequencing (MethylC-Seq), small RNA-seq (microRNAs), and RNA-Seq (mRNAs and non-coding RNAs). MeCP2$^{-/y}$ males, MeCP2$^{-/+}$ females and wild-type controls (males and females) receive a systemic injection of AAV-PHP.B-MeCP2-e1-IRES-GFP, control vector (without MeCP2 cDNA) and vehicle at day 1, 7, 14, and 28, as well as at 12 weeks of age at an optimal dose. Mice (n=8; 4 males and 4 females) are euthanized at 1 or 3 months after injection to assess the parameters indicated above. Information on microRNAs that are overexpressed in response to MeCP2 expression is used to established additional layers of gene expression regulation in addition to that based on miR-132.

Example 5: Contribution of MeCP2 Isoforms to Therapeutic Success or Onset of Neurological Symptoms as a Function of Intervention at Different Stages of Development MeCP2 expression of 1.6-to 6-fold above physiologically normal levels has been observed to cause neurological symptoms both in patients with MeCP2 locus duplication (~2-fold above normal) and transgenic mouse models. The other commonality between patients and transgenic mouse models is that both overexpress the MeCP2-e2 isoform, which unlike the e1 isoform appears to be toxic to primary neurons in culture. In some embodiments, this toxic effect is eliminated by co-expression of FoxG1, which is another gene where mutations are associated with Rett syndrome. In some embodiments, co-expression of FoxG1 with MeCP2 is an additional mechanism to control the side effects associated with MeCP2 overexpression. Therapeutic, safety and epigenomic/transcriptomic experiments with AAV-PHP.B vectors encoding MeCP-e1, MeCP2-e2, MeCP2-e2 and FoxG1, or FoxG1 alone in are conducted MeCP2$^{-/y}$ males, MeCP2$^{+/-}$ females and wild-type age matched controls.

---

SEQUENCES

>SEQ ID NO: 1 human MeCP2 isoform e1 amino acid sequence (NM_001110792)
MAAAAAAAPSGGGGGGEEERLEEKSEDQDLQGLKDKPLKFKKVKKDKKEEK

EGKHEPVQPSAHHSAEPAEAGKAETSEGSGSAPAVPEASASPKQRRSIIRD

RGPMYDDPTLPEGWTRKLKQRKSGRSAGKYDVYLINPQGKAFRSKVELIAY

FEKVGDTSLDPNDFDFTVTGRGSPSRREQKPPKKPKSPKAPGTGRGRGRPK

GSGTTRPKAATSEGVQVKRVLEKSPGKLLVKMPFQTSPGGKAEGGGATTST

QVMVIKRPGRKRKAEADPQAIPKKRGRKPGSVVAAAAAEAKKKAVKESSIR

SVQETVLPIKKRKTRETVSIEVKEVVKPLLVSTLGEKSGKGLKTCKSPGRK

SKESSPKGRSSSASSPPKKEHHHHHHHSESPKAPVPLLPPLPPPPEPESS

EDPTSPPEPQDLSSSVCKEEKMPRGGSLESDGCPKEPAKTQPAVATAATAA

EKYKHRGEGERKDIVSSSMPRPNREEPVDSRTPVTERVS;

>SEQ ID NO: 2; human MeCP2 isoform e2 amino acid sequence (NM_004992)
MVAGMLGLREEKSEDQDLQGLKDKPLKFKKVKKDKKEEKEGKHEPVQPSAH

HSAEPAEAGKAETSEGSGSAPAVPEASASPKQRRSIIRDRGPMYDDPTLPE

GWTRKLKQRKSGRSAGKYDVYLINPQGKAFRSKVELIAYFEKVGDTSLDPN

DFDFTVTGRGSPSRREQKPPKKPKSPKAPGTGRGRGRPKGSGTTRPKAATS

EGVQVKRVLEKSPGKLLVKMPFQTSPGGKAEGGGATTSTQVMVIKRPGRKR

KAEADPQAIPKKRGRKPGSVVAAAAAEAKKKAVKESSIRSVQETVLPIKKR

KTRETVSIEVKEVVKPLLVSTLGEKSGKGLKTCKSPGRKSKESSPKGRSSS

ASSPPKKEHHHHHHHSESPKAPVPLLPPLPPPPEPESSEDPTSPPEPQDL

SSSVCKEEKMPRGGSLESDGCPKEPAKTQPAVATAATAAEKYKHRGEGERK

DIVSSSMPRPNREEPVDSRTPVTERVS

>SEQ ID NO: 3; mouse MeCP2 promoter DNA sequence
AATTGAGGGCGTCACCGCTAAGGCTCCGCCCCAGCCTGGGCTCCACAACCA

ATGAAGGGTAATCTCGACAAAGAGCAAGGGGTGGGGCGCGGGCGCGCAGGT

GCAGCAGCACACAGGCTGGTCGGGAGGGCGGGGCGCGACGTCTGCCGTGCG

GGGTCCCGGCATCGGTT

>SEQ ID NO: 4; miR-122 binding site DNA sequence
ACAAACACCATTGTCACACTCCA

>SEQ ID NO: 5; miR-1 binding site DNA sequence
ATACATACTTCTTTACATTCCA

>SEQ ID NO: 6; miR-132 binding site DNA sequence
CGACCATGGCTGTAGACTGTTA

>SEQ ID NO: 7; MeCP2 in vitro construct nucleic

SEQUENCES acid sequence (scAAV-Mec229-hMeCP2-miR132(1x)miR122-1(3x) plasmid)
CTGCGCGCTCGCTCGCTCACTGAGGCCGCCCGGGCAAAGCCCGGGCGTCGG
GCGACCTTTGGTCGCCCGGCCTCAGTGAGCGAGCGAGCGCGCAGAGAGGGA
GTGTAGCCATGCTCTAGGAAGATCAATTCGGTACAATTCACGCGTCGACAA
TTGAGGGCGTCACCGCTAAGGCTCCGCCCCAGCCTGGGCTCCACAACCAAT
GAAGGGTAATCTCGACAAAGAGCAAGGGGTGGGGCGCGGGCGCGCAGGTGC
AGCAGCACACAGGCTGGTCGGGAGGGCGGGGCGCGACGTCTGCCGTGCGGG
GTCCCGGCATCGGTTGCGCGCGCGCTCCCTCCTCTCGGAGAGAGGGCTGTG
GTAAAACCCGTCCGGAAAATGGCTGCAGCCGCTGCCGCAGCGCCGAGCGGC
GGAGGTGGCGGTGGCGAGGAGGAGAGACTGGAAGAAAAGTCAGAAGACCAG
GACCTCCAGGGCCTCAAGGACAAACCCCTCAAGTTTAAAAAGGTGAAGAAA
GATAAGAAAGAAGAGAAAGAGGGCAAGCATGAGCCCGTGCAGCCATCAGCC
CACCACTCTGCTGAGCCCGCAGAGGCAGGCAAAGCAGAGACATCAGAAGGG
TCAGGCTCCGCCCCGGCTGTGCCGGAAGCTTCTGCCTCCCCCAAACAGCGG
CGCTCCATCATCCGTGACCGGGGACCCATGTATGATGACCCCACCCTGCCT
GAAGGCTGGACACGGAAGCTTAAGCAAAGGAAATCTGGACGCTCTGCTGGG
AAGTATGATGTGTATTTGATCAATCCCCAGGGAAAAGCCTTTCGCTCTAAA
GTGGAGTTGATTGCGTACTTCGAAAAGGTAGGCGACACATCCCTGGACCCT
AATGATTTTGACTTCACGGTAACTGGGAGAGGGAGCCCCTCCCGGCGAGAG
CAGAAACCACCTAAGAAGCCCAAATCTCCCAAAGCTCCAGGAACTGGCAGA
GGTCGGGGACGCCCCAAAGGGAGCGGCACCACGAGACCCAAGGCAGCTACG
TCAGAGGGTGTGCAGGTGAAAAGGGTCCTGGAGAAAAGTCCTGGGAAGCTC
CTTGTCAAGATGCCTTTTCAAACTTCGCCAGGGGGCAAGGCTGAGGGGGGT
GGGGCCACCACATCCACCCAGGTCATGGTGATCAAACGCCCCGGCAGGAAG
CGAAAAGCTGAGGCAGACCCTCAGGCCATTCCCAAGAAACGGGGTCGAAAG
CCGGGGAGTGTGGTGGCAGCCGCTGCCGCCGAGGCCAAAAAGAAAGCCGTG
AAGGAGTCTTCTATCCGATCTGTGCAGGAGACCGTACTCCCCATCAAGAAG
CGCAAGACCCGGGAGACGGTCAGCATCGAGGTCAAGGAAGTGGTGAAGCCC
CTGCTGGTGTCCACCCTCGGTGAGAAGAGCGGGAAAGGACTGAAGACCTGT
AAGAGCCCTGGGCGGAAAAGCAAGGAGAGCAGCCCCAAGGGGCGCAGCAGC
AGCGCCTCCTCACCCCCCAAGAAGGAGCACCACCACCATCACCACCACTCA
GAGTCCCCAAAGGCCCCGTGCCACTGCTCCCACCCCTGCCCCCACCTCCA
CCTGAGCCCGAGAGCTCCGAGGACCCCACCAGCCCCCTGAGCCCCAGGAC
TTGAGCAGCAGCGTCTGCAAAGAGGAGAAGATGCCCAGAGGAGGCTCACTG
GAGAGCGACGGCTGCCCCAAGGAGCCAGCTAAGACTCAGCCCGCGGTTGCC
ACCGCCGCCACGGCCGCAGAAAAGTACAAACACCGAGGGGAGGGAGAGCGC
AAAGACATTGTTTCATCCTCCATGCCAAGGCCAAACAGAGAGGAGCCTGTG
GACAGCCGGACGCCCGTGACCGAGAGAGTTAGCGAGCAGAAGCTGATCTCA
GAGGAGGACCTGTGACGACCATGGCTGTAGACTGTTACTCGAGATACATAC TTCTTTACATTCCAATACATACTTCTTTACATTCCAATACATACTTCTTTA
CATTCCACCATGGACTAGTACAAACACCATTGTCACACTCCAACAAACACC
ATTGTCACACTCCAACAAACACCATTGTCACACTCCAGCGGCCGCTTCGAT
CCGATCTTTTTCCCTCTGCCAAAAATTATGGGGACATCATGAAGCCCCTTG
AGCATCTGACTTCTGGCTAATAAAGGAAATTTATTTTCATTGCAATAGTGT
GTTGGAATTTTTTGTGTCTCTCACTCGGCCTAGGTAGATAAGTAGCATGGC
GGGTTAATCATTAACTACAAGGAACCCCTAGTGATGGAGTTGGCCACTCCC
TCTCTGCGCGCTCGCTCGCTCACTGAGGCCGGGCGACCAAAGGTCGCCCGA
CGCCCGGGCTTTGCCCGGGCGGCCTCAGTGAGCGAGCGAGCGCGCAGCCTT
AATTAACCTAATTCACTGGCCGTCGTTTTACAACGTCGTGACTGGGAAAAC
CCTGGCGTTACCCAACTTAATCGCCTTGCAGCACATCCCCCTTTCGCCAGC
TGGCGTAATAGCGAAGAGGCCCGCACCGATCGCCCTTCCCAACAGTTGCGC
AGCCTGAATGGCGAATGGGACGCGCCCTGTAGCGGCGCATTAAGCGCGGCG
GGTGTGGTGGTTACGCGCAGCGTGACCGCTACACTTGCCAGCGCCCTAGCG
CCCGCTCCTTTCGCTTTCTTCCCTTCCTTTCTCGCCACGTTCGCCGGCTTT
CCCCGTCAAGCTCTAAATCGGGGGCTCCCTTTAGGGTTCCGATTTAGTGCT
TTACGGCACCTCGACCCCAAAAAACTTGATTAGGGTGATGGTTCACGTAGT
GGGCCATCGCCCTGATAGACGGTTTTTCGCCCTTTGACGTTGGAGTCCACG
TTCTTTAATAGTGGACTCTTGTTCCAAACTGGAACAACACTCAACCCTATC
TCGGTCTATTCTTTTGATTTATAAGGGATTTTGCCGATTTCGGCCTATTGG
TTAAAAAATGAGCTGATTTAACAAAAATTTAACGCGAATTTTAACAAAATA
TTAACGCTTACAATTTAGGTGGCACTTTTCGGGGAAATGTGCGCGGAACCC
CTATTTGTTTATTTTTCTAAATACATTCAAATATGTATCCGCTCATGAGAC
AATAACCCTGATAAATGCTTCAATAATATTGAAAAAGGAAGAGTATGAGTA
TTCAACATTTCCGTGTCGCCCTTATTCCCTTTTTTGCGGCATTTTGCCTTC
CTGTTTTTGCTCACCCAGAAACGCTGGTGAAAGTAAAAGATGCTGAAGATC
AGTTGGGTGCACGAGTGGGTTACATCGAACTGGATCTCAACAGCGGTAAGA
TCCTTGAGAGTTTTCGCCCCGAAGAACGTTTTCCAATGATGAGCACTTTTA
AAGTTCTGCTATGTGGCGCGGTATTATCCCGTATTGACGCCGGGCAAGAGC
AACTCGGTCGCCGCATACACTATTCTCAGAATGACTTGGTTGAGTACTCAC
CAGTCACAGAAAAGCATCTTACGGATGGCATGACAGTAAGAGAATTATGCA
GTGCTGCCATAACCATGAGTGATAACACTGCGGCCAACTTACTTCTGACAA
CGATCGGAGGACCGAAGGAGCTAACCGCTTTTTTGCACAACATGGGGGATC
ATGTAACTCGCCTTGATCGTTGGGAACCGGAGCTGAATGAAGCCATACCAA
ACGACGAGCGTGACACCACGATGCCTGTAGCAATGGCAACAACGTTGCGCA
AACTATTAACTGGCGAACTACTTACTCTAGCTTCCCGGCAACAATTAATAG
ACTGGATGGAGGCGGATAAAGTTGCAGGACCACTTCTGCGCTCGGCCCTTC
CGGCTGGCTGGTTTATTGCTGATAAATCTGGAGCCGGTGAGCGTGGGTCTC

| SEQUENCES |
|---|
| GCGGTATCATTGCAGCACTGGGGCCAGATGGTAAGCCCTCCCGTATCGTAG |
| TTATCTACACGACGGGGAGTCAGGCAACTATGGATGAACGAAATAGACAGA |
| TCGCTGAGATAGGTGCCTCACTGATTAAGCATTGGTAACTGTCAGACCAAG |
| TTTACTCATATATACTTTAGATTGATTTAAAACTTCATTTTTAATTTAAAA |
| GGATCTAGGTGAAGATCCTTTTTGATAATCTCATGACCAAAATCCCTTAAC |
| GTGAGTTTTCGTTCCACTGAGCGTCAGACCCCGTAGAAAAGATCAAAGGAT |
| CTTCTTGAGATCCTTTTTTTCTGCGCGTAATCTGCTGCTTGCAAACAAAAA |
| AACCACCGCTACCAGCGGTGGTTTGTTTGCCGGATCAAGAGCTACCAACTC |
| TTTTTCCGAAGGTAACTGGCTTCAGCAGAGCGCAGATACCAAATACTGTTC |
| TTCTAGTGTAGCCGTAGTTAGGCCACCACTTCAAGAACTCTGTAGCACCGC |
| CTACATACCTCGCTCTGCTAATCCTGTTACCAGTGGCTGCTGCCAGTGGCG |
| ATAAGTCGTGTCTTACCGGGTTGGACTCAAGACGATAGTTACCGGATAAGG |
| CGCAGCGGTCGGGCTGAACGGGGGGTTCGTGCACACAGCCCAGCTTGGAGC |
| GAACGACCTACACCGAACTGAGATACCTACAGCGTGAGCTATGAGAAAGCG |
| CCACGCTTCCCGAAGGGAGAAAGGCGGACAGGTATCCGGTAAGCGGCAGGG |
| TCGGAACAGGAGAGCGCACGAGGGAGCTTCCAGGGGGAAACGCCTGGTATC |
| TTTATAGTCCTGTCGGGTTTCGCCACCTCTGACTTGAGCGTCGATTTTTGT |
| GATGCTCGTCAGGGGGCGGAGCCTATGGAAAAACGCCAGCAACGCGGCCT |
| TTTTACGGTTCCTGGCCTTTTGCTGGCCTTTTGCTCACATGTTCTTTCCTG |
| CGTTATCCCCTGATTCTGTGGATAACCGTATTACCGCCTTTGAGTGAGCTG |
| ATACCGCTCGCCGCAGCCGAACGACCGAGCGCAGCGAGTCAGTGAGCGAGG |
| AAGCGGAAGAGCGCCCAATACGCAAACCGCCTCTCCCCGCGCGTTGGCCGA |
| TTCATTAATGCAGCTGGCACGACAGGTTTCCCGACTGGAAAGCGGGCAGTG |
| AGCGCAACGCAATTAATGTGAGTTAGCTCACTCATTAGGCACCCCAGGCTT |
| TACACTTTATGCTTCCGGCTCGTATGTTGTGTGGAATTGTGAGCGGATAAC |
| AATTTCACACAGGAAACAGCTATGACCATGATTACGCCAGATTTAATTAAG |
| GCCTTAATTAGG |

>SEQ ID NO: 8; MeCP2 in vitro construct nucleic
acid sequence (scAAV-Mec229-hMeCP2-miR132(2x)
miR122-1(3x) plasmid)
CTGCGCGCTCGCTCGCTCACTGAGGCCGCCCGGGCAAAGCCCGGGCGTCGG

GCGACCTTTGGTCGCCCGGCCTCAGTGAGCGAGCGAGCGCGCAGAGAGGGA

GTGTAGCCATGCTCTAGGAAGATCAATTCGGTACAATTCACGCGTCGACAA

TTGAGGGCGTCACCGCTAAGGCTCCGCCCCAGCCTGGGCTCCACAACCAAT

GAAGGGTAATCTCGACAAAGAGCAAGGGGTGGGGCGCGGGCGCGCAGGTGC

AGCAGCACACAGGCTGGTCGGGAGGGCGGGGCGCGACGTCTGCCGTGCGGG

GTCCCGGCATCGGTTGCGCGCGCGCTCCCTCCTCTCGGAGAGAGGGCTGTG

GTAAAACCCGTCCGGAAAATGGCTGCAGCCGCTGCCGCAGCGCCGAGCGGC

GGAGGTGGCGGTGGCGAGGAGGAGAGACTGGAAGAAAAGTCAGAAGACCAG

GACCTCCAGGGCCTCAAGGACAAACCCCTCAAGTTTAAAAAGGTGAAGAAA

| SEQUENCES |
|---|
| GATAAGAAAGAAGAGAAAGAGGGCAAGCATGAGCCCGTGCAGCCATCAGCC |
| CACCACTCTGCTGAGCCCGCAGAGGCAGGCAAAGCAGAGACATCAGAAGGG |
| TCAGGCTCCGCCCCGGCTGTGCCGGAAGCTTCTGCCTCCCCCAAACAGCGG |
| CGCTCCATCATCCGTGACCGGGGACCCATGTATGATGACCCCACCCTGCCT |
| GAAGGCTGGACACGGAAGCTTAAGCAAAGGAAATCTGGACGCTCTGCTGGG |
| AAGTATGATGTGTATTTGATCAATCCCCAGGGAAAAGCCTTTCGCTCTAAA |
| GTGGAGTTGATTGCGTACTTCGAAAAGGTAGGCGACACATCCCTGGACCCT |
| AATGATTTTGACTTCACGGTAACTGGGAGAGGGAGCCCCTCCCGGCGAGAG |
| CAGAAACCACCTAAGAAGCCCAAATCTCCCAAAGCTCCAGGAACTGGCAGA |
| GGTCGGGACGCCCCAAAGGGAGCGGCACCACGAGACCCAAGGCAGCTACG |
| TCAGAGGGTGTGCAGGTGAAAAGGGTCCTGGAGAAAGTCCTGGGAAGCTC |
| CTTGTCAAGATGCCTTTTCAAACTTCGCCAGGGGGCAAGGCTGAGGGGGT |
| GGGGCCACCACATCCACCCAGGTCATGGTGATCAAACGCCCCGGCAGGAAG |
| CGAAAAGCTGAGGCAGACCCTCAGGCCATTCCCAAGAAACGGGGTCGAAAG |
| CCGGGGAGTGTGGTGGCAGCCGCTGCCGCCGAGGCCAAAAAGAAAGCCGTG |
| AAGGAGTCTTCTATCCGATCTGTGCAGGAGACCGTACTCCCCATCAAGAAG |
| CGCAAGACCCGGGAGACGGTCAGCATCGAGGTCAAGGAAGTGGTGAAGCCC |
| CTGCTGGTGTCCACCCTCGGTGAGAAGAGCGGGAAAGGACTGAAGACCTGT |
| AAGAGCCCTGGGCGGAAAAGCAAGGAGAGCAGCCCCAAGGGGCGCAGCAGC |
| AGCGCCTCCTCACCCCCAAGAAGGAGCACCACCACCATCACCACCACTCA |
| GAGTCCCCAAAGGCCCCCGTGCCACTGCTCCCACCCCTGCCCCCACCTCCA |
| CCTGAGCCCGAGAGCTCCGAGGACCCCACCAGCCCCCTGAGCCCCAGGAC |
| TTGAGCAGCAGCGTCTGCAAAGAGGAGAAGATGCCCAGAGGAGGCTCACTG |
| GAGAGCGACGGCTGCCCCAAGGAGCCAGCTAAGACTCAGCCCGCGGTTGCC |
| ACCGCCGCCACGGCCGCAGAAAAGTACAAACACCGAGGGGAGGGAGAGCGC |
| AAAGACATTGTTTCATCCTCCATGCCAAGGCCAAACAGAGAGGAGCCTGTG |
| GACAGCCGGACGCCCGTGACCGAGAGAGTTAGCGAGCAGAAGCTGATCTCA |
| GAGGAGGACCTGTGACGACCATGGCTGTAGACTGTTACGACCATGGCTGTA |
| GACTGTTACTCGAGATACATACTTCTTTACATTCCAATACATACTTCTTTA |
| CATTCCAATACATACTTCTTTACATTCCACCATGGACTAGTACAAACACCA |
| TTGTCACACTCCAACAAACACCATTGTCACACTCCAACAAACACCATTGTC |
| ACACTCCAGCGGCCGCTTCGATCCGATCTTTTTCCCTCTGCCAAAAATTAT |
| GGGGACATCATGAAGCCCCTTGAGCATCTGACTTCTGGCTAATAAAGGAAA |
| TTTATTTTCATTGCAATAGTGTGTTGGAATTTTTTGTGTCTCTCACTCGGC |
| CTAGGTAGATAAGTAGCATGGCGGGTTAATCATTAACTACAAGGAACCCCT |
| AGTGATGGAGTTGGCCACTCCCTCTCTGCGCGCTCGCTCGCTCACTGAGGC |
| CGGGCGACCAAAGGTCGCCCGACGCCCGGGCTTTGCCCGGGCGGCCTCAGT |
| GAGCGAGCGAGCGCGCAGCCTTAATTAACCTAATTCACTGGCCGTCGTTTT |
| ACAACGTCGTGACTGGGAAAACCCTGGCGTTACCCAACTTAATCGCCTTGC |

| SEQUENCES |
|---|
| AGCACATCCCCCTTTCGCCAGCTGGCGTAATAGCGAAGAGGCCCGCACCGA |
| TCGCCCTTCCCAACAGTTGCGCAGCCTGAATGGCGAATGGGACGCGCCCTG |
| TAGCGGCGCATTAAGCGCGGCGGGTGTGGTGGTTACGCGCAGCGTGACCGC |
| TACACTTGCCAGCGCCCTAGCGCCCGCTCCTTTCGCTTTCTTCCCTTCCTT |
| TCTCGCCACGTTCGCCGGCTTTCCCCGTCAAGCTCTAAATCGGGGGCTCCC |
| TTTAGGGTTCCGATTTAGTGCTTTACGGCACCTCGACCCCAAAAAACTTGA |
| TTAGGGTGATGGTTCACGTAGTGGGCCATCGCCCTGATAGACGGTTTTTCG |
| CCCTTTGACGTTGGAGTCCACGTTCTTTAATAGTGGACTCTTGTTCCAAAC |
| TGGAACAACACTCAACCCTATCTCGGTCTATTCTTTTGATTTATAAGGGAT |
| TTTGCCGATTTCGGCCTATTGGTTAAAAAATGAGCTGATTTAACAAAAATT |
| TAACGCGAATTTTAACAAAATATTAACGCTTACAATTTAGGTGGCACTTTT |
| CGGGGAAATGTGCGCGGAACCCCTATTTGTTTATTTTTCTAAATACATTCA |
| AATATGTATCCGCTCATGAGACAATAACCCTGATAAATGCTTCAATAATAT |
| TGAAAAAGGAAGAGTATGAGTATTCAACATTTCCGTGTCGCCCTTATTCCC |
| TTTTTTGCGGCATTTTGCCTTCCTGTTTTTGCTCACCCAGAAACGCTGGTG |
| AAAGTAAAAGATGCTGAAGATCAGTTGGGTGCACGAGTGGGTTACATCGAA |
| CTGGATCTCAACAGCGGTAAGATCCTTGAGAGTTTTCGCCCCGAAGAACGT |
| TTTCCAATGATGAGCACTTTTAAAGTTCTGCTATGTGGCGCGGTATTATCC |
| CGTATTGACGCCGGGCAAGAGCAACTCGGTCGCCGCATACACTATTCTCAG |
| AATGACTTGGTTGAGTACTCACCAGTCACAGAAAAGCATCTTACGGATGGC |
| ATGACAGTAAGAGAATTATGCAGTGCTGCCATAACCATGAGTGATAACACT |
| GCGGCCAACTTACTTCTGACAACGATCGGAGGACCGAAGGAGCTAACCGCT |
| TTTTTGCACAACATGGGGGATCATGTAACTCGCCTTGATCGTTGGGAACCG |
| GAGCTGAATGAAGCCATACCAAACGACGAGCGTGACACCACGATGCCTGTA |
| GCAATGGCAACAACGTTGCGCAAACTATTAACTGGCGAACTACTTACTCTA |
| GCTTCCCGGCAACAATTAATAGACTGGATGGAGGCGGATAAAGTTGCAGGA |
| CCACTTCTGCGCTCGGCCCTTCCGGCTGGCTGGTTTATTGCTGATAAATCT |
| GGAGCCGGTGAGCGTGGGTCTCGCGGTATCATTGCAGCACTGGGGCCAGAT |
| GGTAAGCCCTCCCGTATCGTAGTTATCTACACGACGGGGAGTCAGGCAACT |
| ATGGATGAACGAAATAGACAGATCGCTGAGATAGGTGCCTCACTGATTAAG |
| CATTGGTAACTGTCAGACCAAGTTTACTCATATATACTTTAGATTGATTTA |
| AAACTTCATTTTTAATTTAAAAGGATCTAGGTGAAGATCCTTTTTGATAAT |
| CTCATGACCAAAATCCCTTAACGTGAGTTTTCGTTCCACTGAGCGTCAGAC |
| CCCGTAGAAAAGATCAAAGGATCTTCTTGAGATCCTTTTTTTCTGCGCGTA |
| ATCTGCTGCTTGCAAACAAAAAAACCACCGCTACCAGCGGTGGTTTGTTTG |
| CCGGATCAAGAGCTACCAACTCTTTTTCCGAAGGTAACTGGCTTCAGCAGA |
| GCGCAGATACCAAATACTGTTCTTCTAGTGTAGCCGTAGTTAGGCCACCAC |
| TTCAAGAACTCTGTAGCACCGCCTACATACCTCGCTCTGCTAATCCTGTTA |
| CCAGTGGCTGCTGCCAGTGGCGATAAGTCGTGTCTTACCGGGTTGGACTCA |
| AGACGATAGTTACCGGATAAGGCGCAGCGGTCGGGCTGAACGGGGGGTTCG |
| TGCACACAGCCCAGCTTGGAGCGAACGACCTACACCGAACTGAGATACCTA |
| CAGCGTGAGCTATGAGAAAGCGCCACGCTTCCCGAAGGGAGAAAGGCGGAC |
| AGGTATCCGGTAAGCGGCAGGGTCGGAACAGGAGAGCGCACGAGGGAGCTT |
| CCAGGGGGAAACGCCTGGTATCTTTATAGTCCTGTCGGGTTTCGCCACCTC |
| TGACTTGAGCGTCGATTTTTGTGATGCTCGTCAGGGGGCGGAGCCTATGG |
| AAAAACGCCAGCAACGCGGCCTTTTTACGGTTCCTGGCCTTTTGCTGGCCT |
| TTTGCTCACATGTTCTTTCCTGCGTTATCCCCTGATTCTGTGGATAACCGT |
| ATTACCGCCTTTGAGTGAGCTGATACCGCTCGCCGCAGCCGAACGACCGAG |
| CGCAGCGAGTCAGTGAGCGAGGAAGCGGAAGAGCGCCCAATACGCAAACCG |
| CCTCTCCCCGCGCGTTGGCCGATTCATTAATGCAGCTGGCACGACAGGTTT |
| CCCGACTGGAAAGCGGGCAGTGAGCGCAACGCAATTAATGTGAGTTAGCTC |
| ACTCATTAGGCACCCCAGGCTTTACACTTTATGCTTCCGGCTCGTATGTTG |
| TGTGGAATTGTGAGCGGATAACAATTTCACACAGGAAACAGCTATGACCAT |
| GATTACGCCAGATTTAATTAAGGCCTTAATTAGG |

>SEQ ID NO: 9; MeCP2 in vitro construct nucleic
acid sequence (scAAV-Mec229-hMeCP2-
miR132(3x) miR122-1(3x) plasmid)
CTGCGCGCTCGCTCGCTCACTGAGGCCGCCCGGGCAAAGCCCGGGCGTCGG
GCGACCTTTGGTCGCCCGGCCTCAGTGAGCGAGCGAGCGCGCAGAGAGGGA
GTGTAGCCATGCTCTAGGAAGATCAATTCGGTACAATTCACGCGTCGACAA
TTGAGGGCGTCACCGCTAAGGCTCCGCCCCAGCCTGGGCTCCACAACCAAT
GAAGGGTAATCTCGACAAAGAGCAAGGGGTGGGGCGCGGGCGCGCAGGTGC
AGCAGCACACAGGCTGGTCGGGAGGGCGGGGCGCGACGTCTGCCGTGCGGG
GTCCCGGCATCGGTTGCGCGCGCGCTCCCTCCTCTCGGAGAGGGCTGTG
GTAAAACCCGTCCGGAAAATGGCTGCAGCCGCTGCCGCAGCGCCGAGCGGC
GGAGGTGGCGGTGGCGAGGAGGAGAGACTGGAAGAAAAGTCAGAAGACCAG
GACCTCCAGGGCCTCAAGGACAAACCCCTCAAGTTTAAAAAGGTGAAGAAA
GATAAGAAAGAAGAGAAAGAGGGCAAGCATGAGCCCGTGCAGCCATCAGCC
CACCACTCTGCTGAGCCCGCAGAGGCAGGCAAAGCAGAGACATCAGAAGGG
TCAGGCTCCGCCCCGGCTGTGCCGGAAGCTTCTGCCTCCCCAAACAGCGG
CGCTCCATCATCCGTGACCGGGACCCATGTATGATGACCCCACCCTGCCT
GAAGGCTGGACACGGAAGCTTAAGCAAAGGAAATCTGGACGCTCTGCTGGG
AAGTATGATGTGTATTTGATCAATCCCCAGGGAAAAGCCTTTCGCTCTAAA
GTGGAGTTGATTGCGTACTTCGAAAAGGTAGGCGACACATCCCTGGACCCT
AATGATTTGACTTCACGGTAACTGGGAGAGGGAGCCCCTCCCGGCGAGAG
CAGAAACCACCTAAGAAGCCCAAATCTCCCAAAGCTCCAGGAACTGGCAGA
GGTCGGGGACGCCCCAAAGGGAGCGGCACCACGAGACCCAAGGCAGCTACG
TCAGAGGGTGTGCAGGTGAAAAGGGTCCTGGAGAAAAGTCCTGGGAAGCTC

| SEQUENCES |
|---|
| CTTGTCAAGATGCCTTTTCAAACTTCGCCAGGGGGCAAGGCTGAGGGGGT |
| GGGGCCACCACATCCACCCAGGTCATGGTGATCAAACGCCCCGGCAGGAAG |
| CGAAAAGCTGAGGCAGACCCTCAGGCCATTCCCAAGAAACGGGGTCGAAAG |
| CCGGGGAGTGTGGTGGCAGCCGCTGCCGCCGAGGCCAAAAAGAAAGCCGTG |
| AAGGAGTCTTCTATCCGATCTGTGCAGGAGACCGTACTCCCCATCAAGAAG |
| CGCAAGACCCGGGAGACGGTCAGCATCGAGGTCAAGGAAGTGGTGAAGCCC |
| CTGCTGGTGTCCACCCTCGGTGAGAAGAGCGGGAAAGGACTGAAGACCTGT |
| AAGAGCCCTGGGCGGAAAAGCAAGGAGAGCAGCCCCAAGGGGCGCAGCAGC |
| AGCGCCTCCTCACCCCCAAGAAGGAGCACCACCACCATCACCACCACTCA |
| GAGTCCCCAAAGGCCCCCGTGCCACTGCTCCCACCCCTGCCCCCACCTCCA |
| CCTGAGCCCGAGAGCTCCGAGGACCCCACCAGCCCCCTGAGCCCCAGGAC |
| TTGAGCAGCAGCGTCTGCAAAGAGGAGAAGATGCCCAGAGGAGGCTCACTG |
| GAGAGCGACGGCTGCCCCAAGGAGCCAGCTAAGACTCAGCCCGCGGTTGCC |
| ACCGCCGCCACGGCCGCAGAAAAGTACAAACACCGAGGGGAGGGAGAGCGC |
| AAAGACATTGTTTCATCCTCCATGCCAAGGCCAAACAGAGAGGAGCCTGTG |
| GACAGCCGGACGCCCGTGACCGAGAGAGTTAGCGAGCAGAAGCTGATCTCA |
| GAGGAGGACCTGTGACGACCATGGCTGTAGACTGTTACGACCATGGCTGTA |
| GACTGTTACGACCATGGCTGTAGACTGTTACTCGAGATACATACTTCTTTA |
| CATTCCAATACATACTTCTTTACATTCCAATACATACTTCTTTACATTCCA |
| CCATGGACTAGTACAAACACCATTGTCACACTCCAACAAACACCATTGTCA |
| CACTCCAACAAACACCATTGTCACACTCCAGCGGCCGCTTCGATCCGATCT |
| TTTTCCCTCTGCCAAAAATTATGGGGACATCATGAAGCCCCTTGAGCATCT |
| GACTTCTGGCTAATAAAGGAAATTTATTTTCATTGCAATAGTGTGTTGGAA |
| TTTTTTGTGTCTCTCACTCGGCCTAGGTAGATAAGTAGCATGGCGGGTTAA |
| TCATTAACTACAAGGAACCCCTAGTGATGGAGTTGGCCACTCCCTCTCTGC |
| GCGCTCGCTCGCTCACTGAGGCCGGGCGACCAAAGGTCGCCCGACGCCCGG |
| GCTTTGCCCGGGCGGCCTCAGTGAGCGAGCGAGCGCGCAGCCTTAATTAAC |
| CTAATTCACTGGCCGTCGTTTTACAACGTCGTGACTGGGAAAACCCTGGCG |
| TTACCCAACTTAATCGCCTTGCAGCACATCCCCCTTTCGCCAGCTGGCGTA |
| ATAGCGAAGAGGCCCGCACCGATCGCCCTTCCCAACAGTTGCGCAGCCTGA |
| ATGGCGAATGGGACGCGCCCTGTAGCGGCGCATTAAGCGCGGCGGGTGTGG |
| TGGTTACGCGCAGCGTGACCGCTACACTTGCCAGCGCCCTAGCGCCCGCTC |
| CTTTCGCTTTCTTCCCTTCCTTTCTCGCCACGTTCGCCGGCTTTCCCCGTC |
| AAGCTCTAAATCGGGGCTCCCTTTAGGGTTCCGATTTAGTGCTTTACGGC |
| ACCTCGACCCCAAAAAACTTGATTAGGGTGATGGTTCACGTAGTGGGCCAT |
| CGCCCTGATAGACGGTTTTTCGCCCTTTGACGTTGGAGTCCACGTTCTTTA |
| ATAGTGGACTCTTGTTCCAAACTGGAACAACACTCAACCCTATCTCGGTCT |
| ATTCTTTTGATTTATAAGGGATTTTGCCGATTTCGGCCTATTGGTTAAAAA |
| ATGAGCTGATTTAACAAAAATTTAACGCGAATTTTAACAAAATATTAACGC |
| TTACAATTTAGGTGGCACTTTTCGGGGAAATGTGCGCGGAACCCCTATTTG |
| TTTATTTTTCTAAATACATTCAAATATGTATCCGCTCATGAGACAATAACC |
| CTGATAAATGCTTCAATAATATTGAAAAAGGAAGAGTATGAGTATTCAACA |
| TTTCCGTGTCGCCCTTATTCCCTTTTTTGCGGCATTTTGCCTTCCTGTTTT |
| TGCTCACCCAGAAACGCTGGTGAAAGTAAAAGATGCTGAAGATCAGTTGGG |
| TGCACGAGTGGGTTACATCGAACTGGATCTCAACAGCGGTAAGATCCTTGA |
| GAGTTTTCGCCCCGAAGAACGTTTTCCAATGATGAGCACTTTTAAAGTTCT |
| GCTATGTGGCGCGGTATTATCCCGTATTGACGCCGGGCAAGAGCAACTCGG |
| TCGCCGCATACACTATTCTCAGAATGACTTGGTTGAGTACTCACCAGTCAC |
| AGAAAAGCATCTTACGGATGGCATGACAGTAAGAGAATTATGCAGTGCTGC |
| CATAACCATGAGTGATAACACTGCGGCCAACTTACTTCTGACAACGATCGG |
| AGGACCGAAGGAGCTAACCGCTTTTTTGCACAACATGGGGGATCATGTAAC |
| TCGCCTTGATCGTTGGGAACCGGAGCTGAATGAAGCCATACCAAACGACGA |
| GCGTGACACCACGATGCCTGTAGCAATGGCAACAACGTTGCGCAAACTATT |
| AACTGGCGAACTACTTACTCTAGCTTCCCGGCAACAATTAATAGACTGGAT |
| GGAGGCGGATAAAGTTGCAGGACCACTTCTGCGCTCGGCCCTTCCGGCTGG |
| CTGGTTTATTGCTGATAAATCTGGAGCCGGTGAGCGTGGGTCTCGCGGTAT |
| CATTGCAGCACTGGGGCCAGATGGTAAGCCCTCCCGTATCGTAGTTATCTA |
| CACGACGGGGAGTCAGGCAACTATGGATGAACGAAATAGACAGATCGCTGA |
| GATAGGTGCCTCACTGATTAAGCATTGGTAACTGTCAGACCAAGTTTACTC |
| ATATATACTTTAGATTGATTTAAAACTTCATTTTTAATTTAAAAGGATCTA |
| GGTGAAGATCCTTTTTGATAATCTCATGACCAAAATCCCTTAACGTGAGTT |
| TTCGTTCCACTGAGCGTCAGACCCCGTAGAAAAGATCAAAGGATCTTCTTG |
| AGATCCTTTTTTTCTGCGCGTAATCTGCTGCTTGCAAACAAAAAAACCACC |
| GCTACCAGCGGTGGTTTGTTTGCCGGATCAAGAGCTACCAACTCTTTTTCC |
| GAAGGTAACTGGCTTCAGCAGAGCGCAGATACCAAATACTGTTCTTCTAGT |
| GTAGCCGTAGTTAGGCCACCACTTCAAGAACTCTGTAGCACCGCCTACATA |
| CCTCGCTCTGCTAATCCTGTTACCAGTGGCTGCTGCCAGTGGCGATAAGTC |
| GTGTCTTACCGGGTTGGACTCAAGACGATAGTTACCGGATAAGGCGCAGCG |
| GTCGGGCTGAACGGGGGGTTCGTGCACACAGCCCAGCTTGGAGCGAACGAC |
| CTACACCGAACTGAGATACCTACAGCGTGAGCTATGAGAAAGCGCCACGCT |
| TCCCGAAGGGAGAAAGGCGGACAGGTATCCGGTAAGCGGCAGGGTCGGAAC |
| AGGAGAGCGCACGAGGGAGCTTCCAGGGGGAAACGCCTGGTATCTTTATAG |
| TCCTGTCGGGTTTCGCCACCTCTGACTTGAGCGTCGATTTTTGTGATGCTC |
| GTCAGGGGGCGGAGCCTATGGAAAAACGCCAGCAACGCGGCCTTTTTACG |
| GTTCCTGGCCTTTTGCTGGCCTTTTGCTCACATGTTCTTTCCTGCGTTATC |
| CCCTGATTCTGTGGATAACCGTATTACCGCCTTTGAGTGAGCTGATACCGC |
| TCGCCGCAGCCGAACGACCGAGCGCAGCGAGTCAGTGAGCGAGGAAGCGGA |

| SEQUENCES |
|---|
| AGAGCGCCCAATACGCAAACCGCCTCTCCCCGCGCGTTGGCCGATTCATTA |
| ATGCAGCTGGCACGACAGGTTTCCCGACTGGAAAGCGGGCAGTGAGCGCAA |
| CGCAATTAATGTGAGTTAGCTCACTCATTAGGCACCCCAGGCTTTACACTT |
| TATGCTTCCGGCTCGTATGTTGTGTGGAATTGTGAGCGGATAACAATTTCA |
| CACAGGAAACAGCTATGACCATGATTACGCCAGATTTAATTAAGGCCTTAA |
| TTAGG |
| >SEQ ID NO: 10; MeCP2 in vivo construct nucleic acid sequence (scAAV-Mec229-hMeCP2-miR132(1x)miR122-1(3x) vector genome) |
| CTGCGCGCTCGCTCGCTCACTGAGGCCGCCCGGGCAAAGCCCGGGCGTCGG |
| GCGACCTTTGGTCGCCCGGCCTCAGTGAGCGAGCGAGCGCGCAGAGAGGGA |
| GTGTAGCCATGCTCTAGGAAGATCAATTCGGTACAATTCACGCGTCGACAA |
| TTGAGGGCGTCACCGCTAAGGCTCCGCCCCAGCCTGGGCTCCACAACCAAT |
| GAAGGGTAATCTCGACAAAGAGCAAGGGGTGGGGCGCGGGCGCGCAGGTGC |
| AGCAGCACACAGGCTGGTCGGGAGGGCGGGGCGCGACGTCTGCCGTGCGGG |
| GTCCCGGCATCGGTTGCGCGCGCGCTCCCTCCTCTCGGAGAGAGGGCTGTG |
| GTAAAACCCGTCCGGAAAATGGCTGCAGCCGCTGCCGCAGCGCCGAGCGGC |
| GGAGGTGGCGGTGGCGAGGAGGAGAGACTGGAAGAAAAGTCAGAAGACCAG |
| GACCTCCAGGGCCTCAAGGACAAACCCCTCAAGTTTAAAAAGGTGAAGAAA |
| GATAAGAAAGAAGAGAAAGAGGGCAAGCATGAGCCCGTGCAGCCATCAGCC |
| CACCACTCTGCTGAGCCCGCAGAGGCAGGCAAAGCAGAGACATCAGAAGGG |
| TCAGGCTCCGCCCCGGCTGTGCCGGAAGCTTCTGCCTCCCCCAAACAGCGG |
| CGCTCCATCATCCGTGACCGGGGACCCATGTATGATGACCCCACCCTGCCT |
| GAAGGCTGGACACGGAAGCTTAAGCAAAGGAAATCTGGACGCTCTGCTGGG |
| AAGTATGATGTGTATTTGATCAATCCCCAGGGAAAAGCCTTTCGCTCTAAA |
| GTGGAGTTGATTGCGTACTTCGAAAAGGTAGGCGACACATCCCTGGACCCT |
| AATGATTTTGACTTCACGGTAACTGGGAGAGGGAGCCCCTCCCGGCGAGAG |
| CAGAAACCACCTAAGAAGCCCAAATCTCCCAAAGCTCCAGGAACTGGCAGA |
| GGTCGGGGACGCCCCAAAGGGAGCGGCACCACGAGACCCAAGGCAGCTACG |
| TCAGAGGGTGTGCAGGTGAAAAGGGTCCTGGAGAAAAGTCCTGGGAAGCTC |
| CTTGTCAAGATGCCTTTTCAAACTTCGCCAGGGGGCAAGGCTGAGGGGGGT |
| GGGGCCACCACATCCACCCAGGTCATGGTGATCAAACGCCCCGGCAGGAAG |
| CGAAAAGCTGAGGCAGACCCTCAGGCCATTCCCAAGAAACGGGGTCGAAAG |
| CCGGGGAGTGTGGTGGCAGCCGCTGCCGCCGAGGCCAAAAAGAAAGCCGTG |
| AAGGAGTCTTCTATCCGATCTGTGCAGGAGACCGTACTCCCCATCAAGAAG |
| CGCAAGACCCGGGAGACGGTCAGCATCGAGGTCAAGGAAGTGGTGAAGCCC |
| CTGCTGGTGTCCACCCTCGGTGAGAAGAGCGGGAAAGGACTGAAGACCTGT |
| AAGAGCCCTGGGCGGAAAAGCAAGGAGAGCAGCCCCAAGGGGCGCAGCAGC |
| AGCGCCTCCTCACCCCCAAGAAGGAGCACCACCACCATCACCACCACTCA |
| GAGTCCCCAAAGGCCCCCGTGCCACTGCTCCCACCCCTGCCCCCACCTCCA |

| SEQUENCES |
|---|
| CCTGAGCCCGAGAGCTCCGAGGACCCCACCAGCCCCCCTGAGCCCCAGGAC |
| TTGAGCAGCAGCGTCTGCAAAGAGGAGAAGATGCCCAGAGGAGGCTCACTG |
| GAGAGCGACGGCTGCCCCAAGGAGCCAGCTAAGACTCAGCCCCGCGGTTGCC |
| ACCGCCGCCACGGCCGCAGAAAAGTACAAACACCGAGGGGAGGGAGAGCGC |
| AAAGACATTGTTTCATCCTCCATGCCAAGGCCAAACAGAGAGGAGCCTGTG |
| GACAGCCGGACGCCCGTGACCGAGAGAGTTAGCGAGCAGAAGCTGATCTCA |
| GAGGAGGACCTGTGACGACCATGGCTGTAGACTGTTACTCGAGATACATAC |
| TTCTTTACATTCCAATACATACTTCTTTACATTCCAATACATACTTCTTTA |
| CATTCCACCATGGACTAGTACAAACACCATTGTCACACTCCAACAAACACC |
| ATTGTCACACTCCAACAAACACCATTGTCACACTCCAGCGGCCGCTTCGAT |
| CCGATCTTTTTCCCTCTGCCAAAAATTATGGGGACATCATGAAGCCCCTTG |
| AGCATCTGACTTCTGGCTAATAAAGGAAATTTATTTTCATTGCAATAGTGT |
| GTTGGAATTTTTTGTGTCTCTCACTCGGCCTAGGTAGATAAGTAGCATGGC |
| GGGTTAATCATTAACTACAAGGAACCCCTAGTGATGGAGTTGGCCACTCCC |
| TCTCTGCGCGCTCGCTCGCTCACTGAGGCCGGGCGACCAAAGGTCGCCCGA |
| CGCCCGGGCTTTGCCCGGGCGGCCTCAGTGAGCGAGCGAGCGCGCAG |
| >SEQ ID NO: 11; MeCP2 in vivo construct nucleic acid sequence (scAAV-Mec229-hMeCP2-miR132(2x)miR122-1(3x) vector genome) |
| CTGCGCGCTCGCTCGCTCACTGAGGCCGCCCGGGCAAAGCCCGGGCGTCGG |
| GCGACCTTTGGTCGCCCGGCCTCAGTGAGCGAGCGAGCGCGCAGAGAGGGA |
| GTGTAGCCATGCTCTAGGAAGATCAATTCGGTACAATTCACGCGTCGACAA |
| TTGAGGGCGTCACCGCTAAGGCTCCGCCCCAGCCTGGGCTCCACAACCAAT |
| GAAGGGTAATCTCGACAAAGAGCAAGGGGTGGGGCGCGGGCGCGCAGGTGC |
| AGCAGCACACAGGCTGGTCGGGAGGGCGGGGCGCGACGTCTGCCGTGCGGG |
| GTCCCGGCATCGGTTGCGCGCGCGCTCCCTCCTCTCGGAGAGAGGGCTGTG |
| GTAAAACCCGTCCGGAAAATGGCTGCAGCCGCTGCCGCAGCGCCGAGCGGC |
| GGAGGTGGCGGTGGCGAGGAGGAGAGACTGGAAGAAAAGTCAGAAGACCAG |
| GACCTCCAGGGCCTCAAGGACAAACCCCTCAAGTTTAAAAAGGTGAAGAAA |
| GATAAGAAAGAAGAGAAAGAGGGCAAGCATGAGCCCGTGCAGCCATCAGCC |
| CACCACTCTGCTGAGCCCGCAGAGGCAGGCAAAGCAGAGACATCAGAAGGG |
| TCAGGCTCCGCCCCGGCTGTGCCGGAAGCTTCTGCCTCCCCCAAACAGCGG |
| CGCTCCATCATCCGTGACCGGGGACCCATGTATGATGACCCCACCCTGCCT |
| GAAGGCTGGACACGGAAGCTTAAGCAAAGGAAATCTGGACGCTCTGCTGGG |
| AAGTATGATGTGTATTTGATCAATCCCCAGGGAAAAGCCTTTCGCTCTAAA |
| GTGGAGTTGATTGCGTACTTCGAAAAGGTAGGCGACACATCCCTGGACCCT |
| AATGATTTTGACTTCACGGTAACTGGGAGAGGGAGCCCCTCCCGGCGAGAG |
| CAGAAACCACCTAAGAAGCCCAAATCTCCCAAAGCTCCAGGAACTGGCAGA |
| GGTCGGGGACGCCCCAAAGGGAGCGGCACCACGAGACCCAAGGCAGCTACG |
| TCAGAGGGTGTGCAGGTGAAAAGGGTCCTGGAGAAAAGTCCTGGGAAGCTC |

CTTGTCAAGATGCCTTTTCAAACTTCGCCAGGGGGCAAGGCTGAGGGGGT
GGGGCCACCACATCCACCCAGGTCATGGTGATCAAACGCCCCGGCAGGAAG
CGAAAAGCTGAGGCAGACCCTCAGGCCATTCCCAAGAAACGGGGTCGAAAG
CCGGGGAGTGTGGTGGCAGCCGCTGCCGCCGAGGCCAAAAAGAAAGCCGTG
AAGGAGTCTTCTATCCGATCTGTGCAGGAGACCGTACTCCCCATCAAGAAG
CGCAAGACCCGGGAGACGGTCAGCATCGAGGTCAAGGAAGTGGTGAAGCCC
CTGCTGGTGTCCACCCTCGGTGAGAAGAGCGGGAAAGGACTGAAGACCTGT
AAGAGCCCTGGGCGGAAAAGCAAGGAGAGCAGCCCCAAGGGGCGCAGCAGC
AGCGCCTCCTCACCCCCCAAGAAGGAGCACCACCACCATCACCACCACTCA
GAGTCCCCAAAGGCCCCCGTGCCACTGCTCCCACCCCTGCCCCCACCTCCA
CCTGAGCCCGAGAGCTCCGAGGACCCCACCAGCCCCCTGAGCCCCAGGAC
TTGAGCAGCAGCGTCTGCAAAGAGGAGAAGATGCCCAGAGGAGGCTCACTG
GAGAGCGACGGCTGCCCCAAGGAGCCAGCTAAGACTCAGCCCGCGGTTGCC
ACCGCCGCCACGGCCGCAGAAAAGTACAAACACCGAGGGGAGGGAGAGCGC
AAAGACATTGTTTCATCCTCCATGCCAAGGCCAAACAGAGAGGAGCCTGTG
GACAGCCGGACGCCCGTGACCGAGAGAGTTAGCGAGCAGAAGCTGATCTCA
GAGGAGGACCTGTGACGACCATGGCTGTAGACTGTTACGACCATGGCTGTA
GACTGTTACTCGAGATACATACTTCTTTACATTCCAATACATACTTCTTTA
CATTCCAATACATACTTCTTTACATTCCACCATGGACTAGTACAAACACCA
TTGTCACACTCCAACAAACACCATTGTCACACTCCAACAAACACCATTGTC
ACACTCCAGCGGCCGCTTCGATCCGATCTTTTTCCCTCTGCCAAAAATTAT
GGGGACATCATGAAGCCCCTTGAGCATCTGACTTCTGGCTAATAAAGGAAA
TTTATTTTCATTGCAATAGTGTGTTGGAATTTTTTGTGTCTCTCACTCGGC
CTAGGTAGATAAGTAGCATGGCGGGTTAATCATTAACTACAAGGAACCCCT
AGTGATGGAGTTGGCCACTCCCTCTCTGCGCGCTCGCTCGCTCACTGAGGC
CGGGCGACCAAAGGTCGCCCGACGCCCGGGCTTTGCCCGGGCGGCCTCAGT
GAGCGAGCGAGCGCGCAG

>SEQ ID NO: 12; MeCP2 in vivo construct nucleic
acid sequence (scAAV-Mec229-hMeCP2-
miR132(3x) miR122-1(3x) vector genome)
CTGCGCGCTCGCTCGCTCACTGAGGCCGCCCGGGCAAAGCCCGGGCGTCGG
GCGACCTTTGGTCGCCCGGCCTCAGTGAGCGAGCGAGCGCGCAGAGAGGGA
GTGTAGCCATGCTCTAGGAAGATCAATTCGGTACAATTCACGCGTCGACAA
TTGAGGGCGTCACCGCTAAGGCTCCGCCCCAGCCTGGGCTCCACAACCAAT
GAAGGGTAATCTCGACAAAGAGCAAGGGGTGGGGCGCGGGCGCGCAGGTGC
AGCAGCACACAGGCTGGTCGGAGGGCGGGGCGCGACGTCTGCCGTGCGGG
GTCCCGGCATCGGTTGCGCGCGCGCTCCCTCCTCTCGGAGAGAGGGCTGTG
GTAAAACCCGTCCGGAAAATGGCTGCAGCCGCTGCCGCAGCGCCGAGCGGC
GGAGGTGGCGGTGGCGAGGAGGAGAGACTGGAAGAAAAGTCAGAAGACCAG
GACCTCCAGGGCCTCAAGGACAAACCCCTCAAGTTTAAAAAGGTGAAGAAA GATAAGAAAGAAGAGAAAGAGGGCAAGCATGAGCCCGTGCAGCCATCAGCC
CACCACTCTGCTGAGCCCGCAGAGGCAGGCAAAGCAGAGACATCAGAAGGG
TCAGGCTCCGCCCCGGCTGTGCCGGAAGCTTCTGCCTCCCCCAAACAGCGG
CGCTCCATCATCCGTGACCGGGGACCCATGTATGATGACCCCACCCTGCCT
GAAGGCTGGACACGGAAGCTTAAGCAAAGGAAATCTGGACGCTCTGCTGGG
AAGTATGATGTGTATTTGATCAATCCCCAGGGAAAAGCCTTTCGCTCTAAA
GTGGAGTTGATTGCGTACTTCGAAAAGGTAGGCGACACATCCCTGGACCCT
AATGATTTTGACTTCACGGTAACTGGGAGAGGGAGCCCCTCCCGGCGAGAG
CAGAAACCACCTAAGAAGCCCAAATCTCCCAAAGCTCCAGGAACTGGCAGA
GGTCGGGACGCCCCAAAGGGAGCGGCACCACGAGACCCAAGGCAGCTACG
TCAGAGGGTGTGCAGGTGAAAAGGGTCCTGGAGAAAAGTCCTGGGAAGCTC
CTTGTCAAGATGCCTTTTCAAACTTCGCCAGGGGGCAAGGCTGAGGGGGT
GGGGCCACCACATCCACCCAGGTCATGGTGATCAAACGCCCCGGCAGGAAG
CGAAAAGCTGAGGCAGACCCTCAGGCCATTCCCAAGAAACGGGGTCGAAAG
CCGGGGAGTGTGGTGGCAGCCGCTGCCGCCGAGGCCAAAAAGAAAGCCGTG
AAGGAGTCTTCTATCCGATCTGTGCAGGAGACCGTACTCCCCATCAAGAAG
CGCAAGACCCGGGAGACGGTCAGCATCGAGGTCAAGGAAGTGGTGAAGCCC
CTGCTGGTGTCCACCCTCGGTGAGAAGAGCGGGAAAGGACTGAAGACCTGT
AAGAGCCCTGGGCGGAAAAGCAAGGAGAGCAGCCCCAAGGGGCGCAGCAGC
AGCGCCTCCTCACCCCCAAGAAGGAGCACCACCACCATCACCACCACTCA
GAGTCCCCAAAGGCCCCCGTGCCACTGCTCCCACCCCTGCCCCCACCTCCA
CCTGAGCCCGAGAGCTCCGAGGACCCCACCAGCCCCCTGAGCCCCAGGAC
TTGAGCAGCAGCGTCTGCAAAGAGGAGAAGATGCCCAGAGGAGGCTCACTG
GAGAGCGACGGCTGCCCCAAGGAGCCAGCTAAGACTCAGCCCGCGGTTGCC
ACCGCCGCCACGGCCGCAGAAAAGTACAAACACCGAGGGGAGGGAGAGCGC
AAAGACATTGTTTCATCCTCCATGCCAAGGCCAAACAGAGAGGAGCCTGTG
GACAGCCGGACGCCCGTGACCGAGAGAGTTAGCGAGCAGAAGCTGATCTCA
GAGGAGGACCTGTGACGACCATGGCTGTAGACTGTTACGACCATGGCTGTA
GACTGTTACGACCATGGCTGTAGACTGTTACTCGAGATACATACTTCTTTA
CATTCCAATACATACTTCTTTACATTCCAATACATACTTCTTTACATTCCA
CCATGGACTAGTACAAACACCATTGTCACACTCCAACAAACACCATTGTCA
CACTCCAACAAACACCATTGTCACACTCCAGCGGCCGCTTCGATCCGATCT
TTTTCCCTCTGCCAAAAATTATGGGGACATCATGAAGCCCCTTGAGCATCT
GACTTCTGGCTAATAAAGGAAATTTATTTTCATTGCAATAGTGTGTTGGAA
TTTTTTGTGTCTCTCACTCGGCCTAGGTAGATAAGTAGCATGGCGGGTTAA
TCATTAACTACAAGGAACCCCTAGTGATGGAGTTGGCCACTCCCTCTCTGC
GCGCTCGCTCGCTCACTGAGGCCGGGCGACCAAAGGTCGCCCGACGCCCGG
GCTTTGCCCGGGCGGCCTCAGTGAGCGAGCGAGCGCGCAG >SEQ ID NO: 13; AAV2 capsid amino acid sequence
MAADGYLPDWLEDTLSEGIRQWWKLKPGPPPPKPAERHKDDSRGLVLPGYK
YLGPFNGLDKGEPVNEADAAALEHDKAYDRQLDSGDNPYLKYNHADAEFQE
RLKEDTSFGGNLGRAVFQAKKRVLEPLGLVEEPVKTAPGKKRPVEHSPVEP
DSSSGTGKAGQQPARKRLNFGQTGDADSVPDPQPLGQPPAAPSGLGTNTMA
TGSGAPMADNNEGADGVGNSSGNWHCDSTWMGDRVITTSTRTWALPTYNNH
LYKQISSQSGASNDNHYFGYSTPWGYFDFNRFHCHFSPRDWQRLINNNWGF
RPKRLNFKLFNIQVKEVTQNDGTTTIANNLTSTVQVFTDSEYQLPYVLGSA
HQGCLPPFPADVFMVPQYGYLTLNNGSQAVGRSSFYCLEYFPSQMLRTGNN
FTFSYTFEDVPFHSSYAHSQSLDRLMNPLIDQYLYYLSRTNTPSGTTTQSR
LQFSQAGASDIRDQSRNWLPGPCYRQQRVSKTSADNNNSEYSWTGATKYHL
NGRDSLVNPGPAMASHKDDEEKFFPQSGVLIFGKQGSEKTNVDIEKVMITD
EEEIRTTNPVATEQYGSVSTNLQRGNRQAATADVNTQGVLPGMVWQDRDVY
LQGPIWAKIPHTDGHFHPSPLMGGFGLKHPPPQILIKNTPVPANPSTTFSA
AKFASFITQYSTGQVSVEIEWELQKENSKRWNPEIQYTSNYNKSVNVDFTV
DTNGVYSEPRPIGTRYLTRNL >SEQ ID NO: 14; AAV9 capsid amino acid sequence
MAADGYLPDWLEDNLSEGIREWWALKPGAPQPKANQQHQDNARGLVLPGYK
YLGPGNGLDKGEPVNAADAAALEHDKAYDQQLKAGDNPYLKYNHADAEFQE
RLKEDTSFGGNLGRAVFQAKKRLLEPLGLVEEAAKTAPGKKRPVEQSPQEP
DSSAGIGKSGAQPAKKRLNFGQTGDTESVPDPQPIGEPPAAPSGVGSLTMA
SGGGAPVADNNEGADGVGSSSGNWHCDSQWLGDRVITTSTRTWALPTYNNH
LYKQISNSTSGGSSNDNAYFGYSTPWGYFDFNRFHCHFSPRDWQRLINNNW
GFRPKRLNFKLFNIQVKEVTDNNGVKTIANNLTSTVQVFTDSDYQLPYVLG
SAHEGCLPPFPADVFMIPQYGYLTLNDGSQAVGRSSFYCLEYFPSQMLRTG
NNFQFSYEFENVPFHSSYAHSQSLDRLMNPLIDQYLYYLSKTINGSGQNQQ
TLKFSVAGPSNMAVQGRNYIPGPSYRQQRVSTTVTQNNNSEFAWPGASSWA
LNGRNSLMNPGPAMASHKEGEDRFFPLSGSLIFGKQGTGRDNVDADKVMIT
NEEEIKTTNPVATESYGQVATNHQSAQAQAQTGWVQNQGILPGMVWQDRDV
YLQGPIWAKIPHTDGNFHPSPLMGGFGMKHPPPQILIKNTPVPADPPTAFN
KDKLNSFITQYSTGQVSVEIEWELQKENSKRWNPEIQYTSNYYKSNNVEFA
VNTGVYSEPRPIGTRYLTRNL >SEQ ID NO: 15; AAV-PHP.B capsid amino acid sequence
MAADGYLPDWLEDNLSEGIREWWALKPGAPQPKANQQHQDNARGLVLPGYK
YLGPGNGLDKGEPVNAADAAALEHDKAYDQQLKAGDNPYLKYNHADAEFQE
RLKEDTSFGGNLGRAVFQAKKRLLEPLGLVEEAAKTAPGKKRPVEQSPQEP
DSSAGIGKSGAQPAKKRLNFGQTGDTESVPDPQPIGEPPAAPSGVGSLTMA
SGGGAPVADNNEGADGVGSSSGNWHCDSQWLGDRVITTSTRTWALPTYNNH
LYKQISNSTSGGSSNDNAYFGYSTPWGYFDFNRFHCHFSPRDWQRLINNNW
GFRPKRLNFKLFNIQVKEVTDNNGVKTIANNLTSTVQVFTDSDYQLPYVLG
SAHEGCLPPFPADVFMIPQYGYLTLNDGSQAVGRSSFYCLEYFPSQMLRTG
NNFQFSYEFENVPFHSSYAHSQSLDRLMNPLIDQYLYYLSRT1NGSGQNQQ
TLKFSVAGPSNMAVQGRNYIPGPSYRQQRVSTTVTQNNNSEFAWPGASSWA
LNGRNSLMNPGPAMASHKEGEDRFFPLSGSLIFGKQGTGRDNVDADKVMIT
NEEEIKTTNPVATESYGQVATNHQSAQTLAVPFKAQAQTGWVQNQGILPGM
VWQDRDVYLQGPIWAKIPHTDGNFHPSPLMGGFGMKHPPPQILIKNTPVPA
DPPTAFNKDKLNSFITQYSTGQVSVEIEWELQKENSKRWNPEIQYTSNYYK
SNNVEFAVNTEGVYSEPRPIGTRYLTRNL

What is claimed is:

1. A recombinant nucleic acid encoding a transcript having
   (a) a coding region encoding human MeCP2 or a functional fragment thereof; and,
   (b) a 3'-non-coding region comprising one or more miRNA binding sites, wherein transcript is flanked by adeno-associated virus (AAV) inverted terminal repeats (ITRs).

2. The recombinant nucleic acid of claim 1 further comprising:
   (c) a coding region encoding brain-derived neurotrophic factor (BDNF).

3. The recombinant nucleic acid of claim 1, wherein the one or more miRNA binding sites comprise a binding site for miR-132.

4. The recombinant nucleic acid of claim 3, wherein the miR-132 binding site comprises the sequence set forth in SEQ ID NO: 6.

5. The recombinant nucleic acid of claim 3, wherein further comprising one or more binding sites for miR-122 or miR-1.

6. The recombinant nucleic acid of claim 5, wherein the one or more binding sites comprises the nucleotide sequence set forth in SEQ ID NO: 4 or SEQ ID NO: 5.

7. The recombinant nucleic acid of claim 1, wherein the one or more miRNA binding sites comprise a binding site for miR-22.

8. The recombinant nucleic acid of claim 1, wherein the one or more miRNA binding sites comprise a binding site for miR-19.

9. The recombinant nucleic acid of claim 1, wherein the one or more miRNA binding sites comprise:
   (a) at least one miRNA binding site specific for a miRNA that negatively regulates expression of the transcript; and
   (b) at least one second miRNA binding site specific for a miRNA that inhibits expression of the transcript in a cell of a non-target tissue.

10. The recombinant nucleic acid of claim 1, wherein the one or more miRNA binding sites comprise:
    (a) at least one first miRNA binding site specific for a first miRNA that is positively regulated by expression of MeCP2 in a cell of a target tissue; and
    (b) at least one second miRNA binding site specific for a second miRNA that is expressed, independent of expression of MeCP2, in cells of a non-target tissue.

11. The recombinant nucleic acid of claim 1, wherein the coding region encodes MeCP2 isoform e1.

12. The recombinant nucleic acid of claim 1, wherein the human MeCP2 comprises the sequence set forth in SEQ ID NO:1.

13. The recombinant nucleic acid of claim 1, wherein the coding region encodes MeCP2 isoform e2.

14. The recombinant nucleic acid of claim 1, wherein the human MeCP2 comprises the sequence set forth in SEQ ID NO: 2.

15. A recombinant adeno-associated virus (rAAV) comprising at least one AAV capsid protein and the recombinant nucleic acid of claim 1.

16. The rAAV of claim 15, wherein the AAV ITRs are AAV2 ITRs.

17. The rAAV of claim 15, wherein the AAV capsid protein:
    (i) has a serotype selected from the group consisting of AAV-PHP.B, AAV1, AAV2, AAV2i8, AAV2.5, AAV5, AAV6, AAV8, AAVrh8, AAV9, AAVrh10, AAV-B1, AAV9.45A-String, AAV9.45Angiopep, AAV9.47-Angiopep, AAV9.47-AS, AAV-CAM130, and AAV9HR.

18. The rAAV of claim 17, wherein the AAV9 capsid protein comprises the sequence set forth in SEQ ID NO: 14.

19. A recombinant adeno-associated virus (rAAV) comprising:
    (i) a nucleic acid encoding a transcript comprising a coding region encoding human MeCP2 or a functional fragment thereof; and, a 3'-non-coding region comprising one or more miR-132 miRNA binding sites, wherein transcript is flanked by adeno-associated virus (AAV) inverted terminal repeats (ITRs); and
    (ii) an AAV9 capsid protein.

20. The rAAV of claim 19, further comprising one or more miR-19 miRNA binding sites in the 3' non-coding region.

21. The rAAV of claim 20, further comprising one or more miR-22 miRNA binding sites in the 3' non-coding region.

22. The rAAV of claim 19, wherein the AAV9 capsid protein comprises the sequence set forth in SEQ ID NO: 14.

* * * * *

```
                        SEQUENCE LISTING

<160> NUMBER OF SEQ ID NOS: 15

<210> SEQ ID NO 1
<211> LENGTH: 498
<212> TYPE: PRT
<213> ORGANISM: Human

<400> SEQUENCE: 1

Met Ala Ala Ala Ala Ala Ala Pro Ser Gly Gly Gly Gly Gly
1               5                   10                  15

Glu Glu Glu Arg Leu Glu Glu Lys Ser Glu Asp Gln Asp Leu Gln Gly
            20                  25                  30

Leu Lys Asp Lys Pro Leu Lys Phe Lys Lys Val Lys Lys Asp Lys Lys
        35                  40                  45

Glu Glu Lys Glu Gly Lys His Glu Pro Val Gln Pro Ser Ala His His
    50                  55                  60

Ser Ala Glu Pro Ala Glu Ala Gly Lys Ala Glu Thr Ser Glu Gly Ser
65                  70                  75                  80
```

```
Gly Ser Ala Pro Ala Val Pro Glu Ala Ser Ala Ser Pro Lys Gln Arg
                85                  90                  95

Arg Ser Ile Ile Arg Asp Arg Gly Pro Met Tyr Asp Asp Pro Thr Leu
            100                 105                 110

Pro Glu Gly Trp Thr Arg Lys Leu Lys Gln Arg Lys Ser Gly Arg Ser
        115                 120                 125

Ala Gly Lys Tyr Asp Val Tyr Leu Ile Asn Pro Gln Gly Lys Ala Phe
    130                 135                 140

Arg Ser Lys Val Glu Leu Ile Ala Tyr Phe Glu Lys Val Gly Asp Thr
145                 150                 155                 160

Ser Leu Asp Pro Asn Asp Phe Asp Phe Thr Val Thr Gly Arg Gly Ser
                165                 170                 175

Pro Ser Arg Arg Glu Gln Lys Pro Pro Lys Lys Pro Lys Ser Pro Lys
            180                 185                 190

Ala Pro Gly Thr Gly Arg Gly Arg Gly Arg Pro Lys Gly Ser Gly Thr
        195                 200                 205

Thr Arg Pro Lys Ala Ala Thr Ser Glu Gly Val Gln Val Lys Arg Val
    210                 215                 220

Leu Glu Lys Ser Pro Gly Lys Leu Leu Val Lys Met Pro Phe Gln Thr
225                 230                 235                 240

Ser Pro Gly Gly Lys Ala Glu Gly Gly Ala Thr Thr Ser Thr Gln
                245                 250                 255

Val Met Val Ile Lys Arg Pro Gly Arg Lys Arg Lys Ala Glu Ala Asp
            260                 265                 270

Pro Gln Ala Ile Pro Lys Lys Arg Gly Arg Lys Pro Gly Ser Val Val
        275                 280                 285

Ala Ala Ala Ala Ala Glu Ala Lys Lys Lys Ala Val Lys Glu Ser Ser
    290                 295                 300

Ile Arg Ser Val Gln Glu Thr Val Leu Pro Ile Lys Lys Arg Lys Thr
305                 310                 315                 320

Arg Glu Thr Val Ser Ile Glu Val Lys Glu Val Val Lys Pro Leu Leu
                325                 330                 335

Val Ser Thr Leu Gly Glu Lys Ser Gly Lys Gly Leu Lys Thr Cys Lys
            340                 345                 350

Ser Pro Gly Arg Lys Ser Lys Glu Ser Ser Pro Lys Gly Arg Ser Ser
        355                 360                 365

Ser Ala Ser Ser Pro Pro Lys Lys Glu His His His His His His
    370                 375                 380

Ser Glu Ser Pro Lys Ala Pro Val Pro Leu Leu Pro Pro Leu Pro Pro
385                 390                 395                 400

Pro Pro Pro Glu Pro Glu Ser Ser Glu Asp Pro Thr Ser Pro Pro Glu
                405                 410                 415

Pro Gln Asp Leu Ser Ser Ser Val Cys Lys Glu Glu Lys Met Pro Arg
            420                 425                 430

Gly Gly Ser Leu Glu Ser Asp Gly Cys Pro Lys Glu Pro Ala Lys Thr
        435                 440                 445

Gln Pro Ala Val Ala Thr Ala Ala Thr Ala Ala Glu Lys Tyr Lys His
    450                 455                 460

Arg Gly Glu Gly Glu Arg Lys Asp Ile Val Ser Ser Ser Met Pro Arg
465                 470                 475                 480

Pro Asn Arg Glu Glu Pro Val Asp Ser Arg Thr Pro Val Thr Glu Arg
                485                 490                 495
```

Val Ser

<210> SEQ ID NO 2
<211> LENGTH: 486
<212> TYPE: PRT
<213> ORGANISM: Human

<400> SEQUENCE: 2

```
Met Val Ala Gly Met Leu Gly Leu Arg Glu Glu Lys Ser Glu Asp Gln
1               5                   10                  15

Asp Leu Gln Gly Leu Lys Asp Lys Pro Leu Lys Phe Lys Lys Val Lys
                20                  25                  30

Lys Asp Lys Lys Glu Glu Lys Glu Gly Lys His Glu Pro Val Gln Pro
            35                  40                  45

Ser Ala His His Ser Ala Glu Pro Ala Glu Ala Gly Lys Ala Glu Thr
        50                  55                  60

Ser Glu Gly Ser Gly Ser Ala Pro Ala Val Pro Glu Ala Ser Ala Ser
65                  70                  75                  80

Pro Lys Gln Arg Arg Ser Ile Ile Arg Asp Arg Gly Pro Met Tyr Asp
                85                  90                  95

Asp Pro Thr Leu Pro Glu Gly Trp Thr Arg Lys Leu Lys Gln Arg Lys
                100                 105                 110

Ser Gly Arg Ser Ala Gly Lys Tyr Asp Val Tyr Leu Ile Asn Pro Gln
            115                 120                 125

Gly Lys Ala Phe Arg Ser Lys Val Glu Leu Ile Ala Tyr Phe Glu Lys
        130                 135                 140

Val Gly Asp Thr Ser Leu Asp Pro Asn Asp Phe Asp Phe Thr Val Thr
145                 150                 155                 160

Gly Arg Gly Ser Pro Ser Arg Arg Glu Gln Lys Pro Pro Lys Lys Pro
                165                 170                 175

Lys Ser Pro Lys Ala Pro Gly Thr Gly Arg Gly Arg Gly Arg Pro Lys
            180                 185                 190

Gly Ser Gly Thr Thr Arg Pro Lys Ala Ala Thr Ser Glu Gly Val Gln
        195                 200                 205

Val Lys Arg Val Leu Glu Lys Ser Pro Gly Lys Leu Leu Val Lys Met
210                 215                 220

Pro Phe Gln Thr Ser Pro Gly Gly Lys Ala Glu Gly Gly Gly Ala Thr
225                 230                 235                 240

Thr Ser Thr Gln Val Met Val Ile Lys Arg Pro Gly Arg Lys Arg Lys
                245                 250                 255

Ala Glu Ala Asp Pro Gln Ala Ile Pro Lys Lys Arg Gly Arg Lys Pro
            260                 265                 270

Gly Ser Val Val Ala Ala Ala Ala Glu Ala Lys Lys Lys Ala Val
        275                 280                 285

Lys Glu Ser Ser Ile Arg Ser Val Gln Glu Thr Val Leu Pro Ile Lys
290                 295                 300

Lys Arg Lys Thr Arg Glu Thr Val Ser Ile Glu Val Lys Glu Val Val
305                 310                 315                 320

Lys Pro Leu Leu Val Ser Thr Leu Gly Glu Lys Ser Gly Lys Gly Leu
                325                 330                 335

Lys Thr Cys Lys Ser Pro Gly Arg Lys Ser Lys Glu Ser Ser Pro Lys
            340                 345                 350

Gly Arg Ser Ser Ser Ala Ser Ser Pro Pro Lys Lys Glu His His His
        355                 360                 365
```

```
His His His Ser Glu Ser Pro Lys Ala Pro Val Pro Leu Leu Pro
    370             375                 380

Pro Leu Pro Pro Pro Pro Glu Pro Glu Ser Ser Glu Asp Pro Thr
385             390                 395                 400

Ser Pro Pro Glu Pro Gln Asp Leu Ser Ser Ser Val Cys Lys Glu Glu
                405                 410                 415

Lys Met Pro Arg Gly Gly Ser Leu Glu Ser Asp Gly Cys Pro Lys Glu
            420                 425                 430

Pro Ala Lys Thr Gln Pro Ala Val Ala Thr Ala Thr Ala Ala Glu
            435                 440                 445

Lys Tyr Lys His Arg Gly Glu Gly Glu Arg Lys Asp Ile Val Ser Ser
    450                 455                 460

Ser Met Pro Arg Pro Asn Arg Glu Glu Pro Val Asp Ser Arg Thr Pro
465                 470                 475                 480

Val Thr Glu Arg Val Ser
                485

<210> SEQ ID NO 3
<211> LENGTH: 170
<212> TYPE: DNA
<213> ORGANISM: Mouse

<400> SEQUENCE: 3
aattgagggc gtcaccgcta aggctccgcc ccagcctggg ctccacaacc aatgaagggt      60
aatctcgaca agagcaagg ggtggggcgc gggcgcgcag gtgcagcagc acacaggctg     120
gtcgggaggg cggggcgcga cgtctgccgt gcggggtccc ggcatcggtt               170

<210> SEQ ID NO 4
<211> LENGTH: 23
<212> TYPE: DNA
<213> ORGANISM: Human

<400> SEQUENCE: 4
acaaacacca ttgtcacact cca                                             23

<210> SEQ ID NO 5
<211> LENGTH: 22
<212> TYPE: DNA
<213> ORGANISM: Human

<400> SEQUENCE: 5
atacatactt ctttacattc ca                                              22

<210> SEQ ID NO 6
<211> LENGTH: 22
<212> TYPE: DNA
<213> ORGANISM: Human

<400> SEQUENCE: 6
cgaccatggc tgtagactgt ta                                              22

<210> SEQ ID NO 7
<211> LENGTH: 5214
<212> TYPE: DNA
<213> ORGANISM: human

<400> SEQUENCE: 7
ctgcgcgctc gctcgctcac tgaggccgcc cgggcaaagc ccgggcgtcg ggcgaccttt      60
ggtcgcccgg cctcagtgag cgagcgagcg cgcagagagg gagtgtagcc atgctctagg    120
```

```
aagatcaatt cggtacaatt cacgcgtcga caattgaggg cgtcaccgct aaggctccgc    180
cccagcctgg gctccacaac caatgaaggg taatctcgac aaagagcaag ggtggggcg     240 cgggcgcgca ggtgcagcag cacacaggct ggtcggagg gcggggcgcg acgtctgccg     300
tgcggggtcc cggcatcggt tgcgcgcgcg ctccctcctc tcggagagag ggctgtggta    360
aaacccgtcc ggaaaatggc tgcagccgct gccgcagcgc cgagcggcgg aggtggcggt    420
ggcgaggagg agagactgga agaaaagtca gaagaccagg acctccaggg cctcaaggac    480
aaacccctca agtttaaaaa ggtgaagaaa gataagaaag aagagaaaga gggcaagcat    540
gagcccgtgc agccatcagc ccaccactct gctgagcccg cagaggcagg caaagcagag    600
acatcagaag ggtcaggctc cgccccggct gtgccggaag cttctgcctc ccccaaacag    660
cggcgctcca tcatccgtga ccggggaccc atgtatgatg accccaccct gcctgaaggc    720
tggacacgga agcttaagca aaggaaatct ggacgctctg ctgggaagta tgatgtgtat    780
ttgatcaatc cccagggaaa agcctttcgc tctaaagtgg agttgattgc gtacttcgaa    840
aaggtaggcg acacatccct ggaccctaat gattttgact tcacggtaac tgggagaggg    900
agcccctccc ggcgagagca gaaaccacct aagaagccca aatctcccaa agctccagga    960
actggcagag gtcggggacg ccccaaaggg agcggcacca cgagacccaa ggcagctacg    1020
tcagagggtg tgcaggtgaa aagggtcctg gagaaaagtc ctgggaagct ccttgtcaag    1080 atgcctttc aaacttcgcc aggggcaag gctgaggggg gtggggccac cacatccacc      1140
caggtcatgg tgatcaaacg ccccggcagg aagcgaaaag ctgaggcaga ccctcaggcc    1200
attcccaaga acggggtcg aaagccgggg agtgtggtgg cagccgctgc cgccgaggcc     1260
aaaaagaaag ccgtgaagga gtcttctatc cgatctgtgc aggagaccgt actccccatc    1320
aagaagcgca agacccggga gacggtcagc atcgaggtca aggaagtggt gaagccctg      1380 ctggtgtcca ccctcggtga aagagcggg aaaggactga agacctgtaa gagccctggg      1440
cggaaaagca aggagagcag ccccaaggg cgcagcagca gcgcctcctc acccccaag       1500 aaggagcacc accaccatca ccaccactca gagtccccaa aggcccccgt gccactgctc    1560
ccacccctgc ccccacctcc acctgagccc gagagctccg aggaccccac cagccccct     1620 gagccccagg acttgagcag cagcgtctgc aaagaggaga agatgcccag aggaggctca    1680
ctggagagcg acggctgccc caaggagcca gctaagactc agcccgcggt tgccaccgcc    1740
gccacggccg cagaaaagta caaacaccga ggggagggag agcgcaaaga cattgtttca    1800
tcctccatgc caaggccaaa cagagaggag cctgtggaca gccggacgcc cgtgaccgag    1860
agagttagcg agcagaagct gatctcagag gaggacctgt gacgaccatg gctgtagact    1920
gttactcgag atacatactt ctttacattc aatacatac ttctttacat tccaatacat     1980
acttctttac attccaccat ggactagtac aaacaccatt gtcacactcc aacaaacacc    2040
attgtcacac tccaacaaac accattgtca cactccagcg gccgcttcga tccgatcttt    2100
ttccctctgc caaaaattat ggggacatca tgaagcccct tgagcatctg acttctggct    2160
aataaaggaa atttatttt attgcaatag tgtgttggaa ttttttgtgt ctctcactcg     2220
gcctaggtag ataagtagca tggcgggtta atcattaact acaaggaacc cctagtgatg    2280
gagttggcca ctccctctct gcgcgctcgc tcgctcactg aggccgggcg accaaaggtc    2340
gcccgacgcc cgggctttgc ccgggcggcc tcagtgagcg agcgagcgcg cagccttaat    2400
taacctaatt cactggccgt cgttttacaa cgtcgtgact gggaaaaccc tggcgttacc    2460
```

```
caacttaatc gccttgcagc acatccccct ttcgccagct ggcgtaatag cgaagaggcc    2520
cgcaccgatc gcccttccca acagttgcgc agcctgaatg gcgaatggga cgcgccctgt    2580
agcggcgcat taagcgcggc gggtgtggtg gttacgcgca gcgtgaccgc tacacttgcc    2640
agcgccctag cgcccgctcc tttcgctttc ttcccttcct ttctcgccac gttcgccggc    2700
tttccccgtc aagctctaaa tcgggggctc cctttagggt tccgatttag tgctttacgg    2760
cacctcgacc ccaaaaaact tgattagggt gatggttcac gtagtgggcc atcgccctga    2820
tagacggttt ttcgcccttt gacgttggag tccacgttct ttaatagtgg actcttgttc    2880
caaactggaa caacactcaa ccctatctcg gtctattctt ttgatttata agggattttg    2940
ccgatttcgg cctattggtt aaaaaatgag ctgatttaac aaaaatttaa cgcgaatttt    3000
aacaaaatat taacgcttac aatttaggtg gcacttttcg gggaaatgtg cgcggaaccc    3060
ctatttgttt attttctaa atacattcaa atatgtatcc gctcatgaga caataaccct    3120
gataaatgct tcaataatat tgaaaaagga agagtatgag tattcaacat ttccgtgtcg    3180
cccttattcc cttttttgcg gcattttgcc ttcctgtttt tgctcaccca gaaacgctgg    3240
tgaaagtaaa agatgctgaa gatcagttgg gtgcacgagt gggttacatc gaactggatc    3300
tcaacagcgg taagatcctt gagagttttc gccccgaaga acgttttcca atgatgagca    3360
cttttaaagt tctgctatgt ggcgcggtat tatcccgtat tgacgccggg caagagcaac    3420
tcggtcgccg catacactat tctcagaatg acttggttga gtactcacca gtcacagaaa    3480
agcatcttac ggatggcatg acagtaagag aattatgcag tgctgccata accatgagtg    3540
ataacactgc ggccaactta cttctgacaa cgatcggagg accgaaggag ctaaccgctt    3600
ttttgcacaa catgggggat catgtaactc gccttgatcg ttgggaaccg gagctgaatg    3660
aagccatacc aaacgacgag cgtgacacca cgatgcctgt agcaatggca acaacgttgc    3720
gcaaactatt aactggcgaa ctacttactc tagcttcccg gcaacaatta atagactgga    3780
tggaggcgga taaagttgca ggaccacttc tgcgctcggc ccttccggct ggctggttta    3840
ttgctgataa atctggagcc ggtgagcgtg gtctcgcgg tatcattgca gcactggggc    3900
cagatggtaa gccctcccgt atcgtagtta tctacacgac ggggagtcag gcaactatgg    3960
atgaacgaaa tagacagatc gctgagatag gtgcctcact gattaagcat tggtaactgt    4020
cagaccaagt ttactcatat atactttaga ttgatttaaa acttcatttt taatttaaaa    4080
ggatctaggt gaagatcctt tttgataatc tcatgaccaa aatcccttaa cgtgagtttt    4140
cgttccactg agcgtcagac cccgtagaaa agatcaaagg atcttcttga gatccttttt    4200
ttctgcgcgt aatctgctgc ttgcaaacaa aaaaaccacc gctaccagcg gtggtttgtt    4260
tgccggatca agagctacca actctttttc cgaaggtaac tggcttcagc agagcgcaga    4320
taccaaatac tgttcttcta gtgtagccgt agttaggcca ccacttcaag aactctgtag    4380
caccgcctac atacctcgct ctgctaatcc tgttaccagt ggctgctgcc agtggcgata    4440
agtcgtgtct taccgggttg gactcaagac gatagttacc ggataaggcg cagcggtcgg    4500
gctgaacggg gggttcgtgc acacagccca gcttggagcg aacgacctac accgaactga    4560
gatacctaca gcgtgagcta tgagaaagcg ccacgcttcc cgaagggaga aaggcggaca    4620
ggtatccggt aagcggcagg gtcggaacag gagagcgcac gagggagctt ccagggggaa    4680
acgcctggta tctttatagt cctgtcgggt ttcgccacct ctgacttgag cgtcgatttt    4740
tgtgatgctc gtcaggggg cggagcctat ggaaaaacgc cagcaacgcg ccttttttac    4800
ggttcctggc cttttgctgg ccttttgctc acatgttctt tcctgcgtta tccctgatt    4860
```

| | |
|---|---|
| ctgtggataa ccgtattacc gcctttgagt gagctgatac cgctcgccgc agccgaacga | 4920 |
| ccgagcgcag cgagtcagtg agcgaggaag cggaagagcg cccaatacgc aaaccgcctc | 4980 |
| tccccgcgcg ttggccgatt cattaatgca gctggcacga caggtttccc gactggaaag | 5040 |
| cgggcagtga gcgcaacgca attaatgtga gttagctcac tcattaggca ccccaggctt | 5100 |
| tacactttat gcttccggct cgtatgttgt gtggaattgt gagcggataa caatttcaca | 5160 |
| caggaaacag ctatgaccat gattacgcca gatttaatta aggccttaat tagg | 5214 |

<210> SEQ ID NO 8
<211> LENGTH: 5236
<212> TYPE: DNA
<213> ORGANISM: human

<400> SEQUENCE: 8

| | |
|---|---|
| ctgcgcgctc gctcgctcac tgaggccgcc cgggcaaagc ccgggcgtcg ggcgaccttt | 60 |
| ggtcgcccgg cctcagtgag cgagcgagcg cgcagagagg gagtgtagcc atgctctagg | 120 |
| aagatcaatt cggtacaatt cacgcgtcga caattgaggg cgtcaccgct aaggctccgc | 180 |
| cccagcctgg gctccacaac caatgaaggg taatctcgac aaagagcaag gggtggggcg | 240 |
| cgggcgcgca ggtgcagcag cacacaggct ggtcgggagg gcggggcgcg acgtctgccg | 300 |
| tgcgggtcc cggcatcggt tgcgcgcgcg ctccctcctc tcggagagag ggctgtggta | 360 |
| aaacccgtcc ggaaaatggc tgcagccgct gccgcagcgc cgagcggcgg aggtggcggt | 420 |
| ggcgaggagg agagactgga agaaaagtca gaagaccagg acctccaggg cctcaaggac | 480 |
| aaacccctca gtttaaaaa ggtgaagaaa gataagaaag aagagaaaga gggcaagcat | 540 |
| gagcccgtgc agccatcagc ccaccactct gctgagcccg cagaggcagg caaagcagag | 600 |
| acatcagaag ggtcaggctc cgccccggct gtgccggaag cttctgcctc ccccaaacag | 660 |
| cggcgctcca tcatccgtga ccggggaccc atgtatgatg accccaccct gcctgaaggc | 720 |
| tggacacgga agcttaagca aaggaaatct ggacgctctg ctgggaagta tgatgtgtat | 780 |
| ttgatcaatc cccagggaaa agcctttcgc tctaaagtgg agttgattgc gtacttcgaa | 840 |
| aaggtaggcg acacatccct ggaccctaat gattttgact tcacggtaac tgggagaggg | 900 |
| agcccctccc ggcgagagca gaaaccacct aagaagccca atctcccaa agctccagga | 960 |
| actggcagag gtcgggggacg cccccaaggg agcggcacca cgagacccaa ggcagctacg | 1020 |
| tcagagggtg tgcaggtgaa aagggtcctg gagaaaagtc ctgggaagct ccttgtcaag | 1080 |
| atgccttttc aaacttcgcc aggggcaag gctgaggggg gtggggccac cacatccacc | 1140 |
| caggtcatgg tgatcaaacg ccccggcagg aagcgaaaag ctgaggcaga ccctcaggcc | 1200 |
| attcccaaga acggggtcg aaagccgggg agtgtggtgg cagccgctgc cgccgaggcc | 1260 |
| aaaaagaaag ccgtgaagga gtcttctatc cgatctgtgc aggagaccgt actccccatc | 1320 |
| aagaagcgca agacccggga gacgtcagc atcgaggtca aggaagtggt gaagcccctg | 1380 |
| ctggtgtcca ccctcggtga agagcgggg aaaggactga gacctgtaa gagccctggg | 1440 |
| cggaaaagca aggagagcag ccccaagggg cgcagcagca gcgcctcctc acccccaag | 1500 |
| aaggagcacc accaccatca ccaccactca gagtccccaa aggcccccgt gccactgctc | 1560 |
| ccacccctgc ccccacctcc acctgagccc gagagctccg aggacccac cagcccccct | 1620 |
| gagcccagg acttgagcag cagcgtctgc aaagaggaga gatgccag aggaggctca | 1680 |
| ctggagagcg acggctgccc caaggagcca gctaagactc agcccgcggt tgccaccgcc | 1740 |

```
gccacggccg cagaaaagta caaacaccga ggggagggag agcgcaaaga cattgtttca    1800
tcctccatgc caaggccaaa cagagaggag cctgtggaca gccggacgcc cgtgaccgag    1860
agagttagcg agcagaagct gatctcagag gaggacctgt gacgaccatg gctgtagact    1920
gttacgacca tggctgtaga ctgttactcg agatacatac ttctttacat tccaatacat    1980
acttctttac attccaatac atacttcttt acattccacc atggactagt acaaacacca    2040
ttgtcacact ccaacaaaca ccattgtcac actccaacaa acaccattgt cacactccag    2100
cggccgcttc gatccgatct ttttccctct gccaaaaatt atggggacat catgaagccc    2160
cttgagcatc tgacttctgg ctaataaagg aaatttattt tcattgcaat agtgtgttgg    2220 aatttttgt gtctctcact cggcctaggt agataagtag catggcgggt taatcattaa    2280
ctacaaggaa ccctagtga tggagttggc actccctct ctgcgcgctc gctcgctcac    2340
tgaggccggg cgaccaaagg tcgcccgacg cccgggcttt gccgggcgg cctcagtgag    2400 cgagcgagcg cgcagcctta attaacctaa ttcactggcc gtcgttttac aacgtcgtga    2460
ctgggaaaac cctggcgtta cccaacttaa tcgccttgca gcacatcccc ctttcgccag    2520
ctggcgtaat agcgaagagg cccgcaccga tcgcccttcc caacagttgc gcagcctgaa    2580
tggcgaatgg gacgcgccct gtagcggcgc attaagcgcg gcgggtgtgg tggttacgcg    2640
cagcgtgacc gctacacttg ccagcgccct agcgcccgct cctttcgctt tcttcccttc    2700
ctttctcgcc acgttcgccg gctttccccg tcaagctcta aatcggggc tccctttagg    2760 gttccgattt agtgctttac ggcacctcga ccccaaaaaa cttgattagg gtgatggttc    2820
acgtagtggg ccatcgccct gatagacggt ttttcgccct tgacgttgg agtccacgtt    2880 ctttaatagt ggactcttgt tccaaactgg aacaacactc aaccctatct cggtctattc    2940
ttttgattta tagggatttt tgccgatttc ggcctattgg ttaaaaaatg agctgattta    3000
acaaaaattt aacgcgaatt ttaacaaaat attaacgctt acaatttagg tggcacttt    3060 cggggaaatg tgcgcggaac ccctatttgt ttatttttct aaatacattc aaatatgtat    3120
ccgctcatga cacaataacc ctgataaatg cttcaataat attgaaaaag gaagagtatg    3180
agtattcaac atttccgtgt cgcccttatt ccctttttg cggcattttg ccttcctgtt    3240
tttgctcacc cagaaacgct ggtgaaagta aaagatgctg aagatcagtt gggtgcacga    3300
gtgggttaca tcgaactgga tctcaacagc ggtaagatcc ttgagagttt cgccccgaa    3360 gaacgttttc caatgatgag cacttttaaa gttctgctat gtggcgcggt attatcccgt    3420
attgacgccg ggcaagagca actcggtcgc cgcatacact attctcagaa tgacttggtt    3480
gagtactcac cagtcacaga aaagcatctt acggatggca tgacagtaag agaattatgc    3540
agtgctgcca taaccatgag tgataacact gcggccaact tacttctgac aacgatcgga    3600
ggaccgaagg agctaaccgc ttttttgcac aacatggggg atcatgtaac tcgccttgat    3660
cgttgggaac cggagctgaa tgaagccata ccaaacgacg agcgtgacac cacgatgcct    3720
gtagcaatgg caacaacgtt gcgcaaacta ttaactggcg aactacttac tctagcttcc    3780
cggcaacaat taatagactg gatggaggcg gataaagttg caggaccact tctgcgctcg    3840
gcccttccgg ctggctggtt tattgctgat aaatctggag ccggtgagcg tgggtctcgc    3900
ggtatcattg cagcactggg gccagatggt aagccctccc gtatcgtagt tatctacacg    3960
acggggagtc aggcaactat ggatgaacga aatagacaga tcgctgagat aggtgcctca    4020
ctgattaagc attggtaact gtcagaccaa gtttactcat atatacttta gattgattta    4080
aaacttcatt tttaatttaa aaggatctag gtgaagatcc ttttttgataa tctcatgacc    4140
```

```
aaaatccctt aacgtgagtt ttcgttccac tgagcgtcag accccgtaga aagatcaaa       4200 ggatcttctt gagatccttt ttttctgcgc gtaatctgct gcttgcaaac aaaaaaacca      4260
ccgctaccag cggtggtttg tttgccggat caagagctac caactctttt tccgaaggta      4320
actggcttca gcagagcgca gataccaaat actgttcttc tagtgtagcc gtagttaggc      4380
caccacttca agaactctgt agcaccgcct acatacctcg ctctgctaat cctgttacca      4440
gtggctgctg ccagtggcga taagtcgtgt cttaccgggt tggactcaag acgatagtta      4500
ccggataagg cgcagcggtc gggctgaacg gggggttcgt gcacacagcc cagcttggag      4560
cgaacgacct acaccgaact gagataccta cagcgtgagc tatgagaaag cgccacgctt      4620
cccgaaggga gaaaggcgga caggtatccg gtaagcggca gggtcggaac aggagagcgc      4680
acgagggagc ttccaggggg aaacgcctgg tatctttata gtcctgtcgg gtttcgccac      4740
ctctgacttg agcgtcgatt tttgtgatgc tcgtcagggg ggcggagcct atggaaaaac      4800
gccagcaacg cggccttttt acggttcctg gccttttgct ggccttttgc tcacatgttc      4860
tttcctgcgt tatcccctga ttctgtggat aaccgtatta ccgcctttga gtgagctgat      4920
accgctcgcc gcagccgaac gaccgagcgc agcgagtcag tgagcgagga agcggaagag      4980
cgcccaatac gcaaaccgcc tctccccgcg cgttggccga ttcattaatg cagctggcac      5040
gacaggtttc ccgactggaa agcgggcagt gagcgcaacg caattaatgt gagttagctc      5100
actcattagg caccccaggc tttacacttt atgcttccgg ctcgtatgtt gtgtggaatt      5160
gtgagcggat aacaatttca cacaggaaac agctatgacc atgattacgc cagatttaat      5220
taaggcctta attagg                                                      5236

<210> SEQ ID NO 9
<211> LENGTH: 5258
<212> TYPE: DNA
<213> ORGANISM: Human

<400> SEQUENCE: 9
ctgcgcgctc gctcgctcac tgaggccgcc cgggcaaagc ccgggcgtcg ggcgaccttt       60
ggtcgcccgg cctcagtgag cgagcgagcg cgcagagagg gagtgtagcc atgctctagg      120
aagatcaatt cggtacaatt cacgcgtcga caattgaggg cgtcaccgct aaggctccgc      180
cccagcctgg gctccacaac caatgaaggg taatctcgac aaagagcaag gggtggggcg      240
cgggcgcgca ggtgcagcag cacacaggct ggtcgggagg gcgggcgcg acgtctgccg       300 tgcgggtcc cggcatcggt tgcgcgcgcg ctccctcctc tcggagagag ggctgtggta       360
aaacccgtcc ggaaaatggc tgcagccgct gccgcagcgc cgagcggcgg aggtggcggt      420
ggcgaggagg agagactgga agaaaagtca gaagaccagg acctccaggg cctcaaggac      480
aaacccctca gtttaaaaa ggtgaagaaa gataagaaag aagagaaaga gggcaagcat       540
gagcccgtgc agccatcagc ccaccactct gctgagcccg cagaggcagg caaagcagag      600
acatcagaag ggtcaggctc cgccccggct gtgccggaag cttctgcctc ccccaaacag      660
cggcgctcca tcatccgtga ccggggaccc atgtatgatg acccaccct gcctgaaggc       720 tggacacgga agcttaagca aaggaaatct ggacgctctg ctgggaagta tgatgtgtat      780
ttgatcaatc cccagggaaa agcctttcgc tctaaagtgg agttgattgc gtacttcgaa      840
aaggtaggcg acacatccct ggaccctaat gattttgact tcacggtaac tgggagaggg      900
agccctctcc ggcgagagca gaaaccacct aagaagccca atctcccaa agctccagga       960
```

-continued

| | |
|---|---|
| actggcagag gtcggggacg ccccaagggg agcggcacca cgagacccaa ggcagctacg | 1020 |
| tcagagggtg tgcaggtgaa aagggtcctg gagaaaagtc ctgggaagct ccttgtcaag | 1080 |
| atgccttttc aaacttcgcc aggggggcaag gctgaggggg gtggggccac cacatccacc | 1140 |
| caggtcatgg tgatcaaacg ccccggcagg aagcgaaaag ctgaggcaga ccctcaggcc | 1200 |
| attcccaaga acgggggtcg aaagccgggg agtgtggtgg cagccgctgc cgccgaggcc | 1260 |
| aaaaagaaag ccgtgaagga gtcttctatc cgatctgtgc aggagaccgt actccccatc | 1320 |
| aagaagcgca gacccggga gacggtcagc atcgaggtca aggaagtggt gaagcccctg | 1380 |
| ctggtgtcca ccctcggtga aagagcggg aaaggactga agacctgtaa gagccctggg | 1440 |
| cggaaaagca aggagagcag ccccaagggg cgcagcagca gcgcctcctc acccccaag | 1500 |
| aaggagcacc accaccatca ccaccactca gagtccccaa aggcccccgt gccactgctc | 1560 |
| ccacccctgc ccccacctcc acctgagccc gagagctccg gaacccccac cagcccccct | 1620 |
| gagcccagg acttgagcag cagcgtctgc aaagaggaga gatgccag aggaggctca | 1680 |
| ctggagagcg acggctgccc caaggagcca gctaagactc agcccgcggt tgccaccgcc | 1740 |
| gccacggccg cagaaaagta caaacaccga ggggaggag agcgcaaaga cattgtttca | 1800 |
| tcctccatgc caaggccaaa cagagaggag cctgtgacaa gccggacgcc cgtgaccgag | 1860 |
| agagttagcg agcagaagct gatctcagag gaggacctgt gacgaccatg gctgtagact | 1920 |
| gttacgacca tggctgtaga ctgttacgac catggctgta gactgttact cgagatacat | 1980 |
| acttctttac attccaatac atacttcttt acattccaat acatacttct ttacattcca | 2040 |
| ccatggacta gtacaaacac cattgtcaca ctccaacaaa caccattgtc acactccaac | 2100 |
| aaacaccatt gtcacactcc agcggccgct tcgatccgat ctttttccct ctgccaaaaa | 2160 |
| ttatggggac atcatgaagc cccttgagca tctgacttct ggctaataaa ggaaattat | 2220 |
| tttcattgca atagtgtgtt ggaatttttt gtgtctctca ctcggcctag gtagataagt | 2280 |
| agcatggcgg gttaatcatt aactacaagg aaccccctagt gatggagttg ccactccct | 2340 |
| ctctgcgcgc tcgctcgctc actgaggccg gcgaccaaa ggtcgcccga cgcccgggct | 2400 |
| ttgcccgggc ggcctcagtg agcgagcgag cgcgcagcct taattaacct aattcactgg | 2460 |
| ccgtcgtttt acaacgtcgt gactgggaaa accctggcgt tacccaactt aatcgccttg | 2520 |
| cagcacatcc ccctttcgcc agctggcgta atagcgaaga ggcccgcacc gatcgccctt | 2580 |
| cccaacagtt gcgcagcctg aatggcgaat gggacgcgcc ctgtagcggc gcattaagcg | 2640 |
| cggcgggtgt ggtggttacg cgcagcgtga ccgctacact tgccagcgcc ctagcgcccg | 2700 |
| ctcctttcgc tttcttccct cctttctcg ccacgttcgc cggctttccc cgtcaagctc | 2760 |
| taaatcgggg gctcccttta gggttccgat ttagtgcttt acggcacctc gaccccaaaa | 2820 |
| aacttgatta gggtgatggt tcacgtagtg gccatcgcc ctgatagacg ttttttcgcc | 2880 |
| ctttgacgtt ggagtccacg ttctttaata gtggactctt gttccaaact ggaacaacac | 2940 |
| tcaaccctat ctcggtctat tcttttgatt tataagggat tttgccgatt tcggcctatt | 3000 |
| ggttaaaaaa tgagctgatt taacaaaaat ttaacgcgaa ttttaacaaa atattaacgc | 3060 |
| ttacaattta ggtggcactt ttcggggaaa tgtgcgcgga acccctattt gtttattttt | 3120 |
| ctaaatacat tcaaatatgt atccgctcat gagacaataa ccctgataaa tgcttcaata | 3180 |
| atattgaaaa aggaagagta tgagtattca acatttccgt gtcgccctta ttcccttttt | 3240 |
| tgcggcattt tgccttcctg ttttgctca cccagaaacg ctggtgaaag taaaagatgc | 3300 |
| tgaagatcag ttgggtgcac gagtgggtta catcgaactg gatctcaaca gcggtaagat | 3360 |

```
ccttgagagt tttcgccccg aagaacgttt tccaatgatg agcactttta aagttctgct    3420
atgtggcgcg gtattatccc gtattgacgc cgggcaagag caactcggtc gccgcataca    3480
ctattctcag aatgacttgg ttgagtactc accagtcaca gaaaagcatc ttacggatgg    3540
catgacagta agagaattat gcagtgctgc cataaccatg agtgataaca ctgcggccaa    3600
cttacttctg acaacgatcg gaggaccgaa ggagctaacc gcttttttgc acaacatggg    3660
ggatcatgta actcgccttg atcgttggga accggagctg aatgaagcca taccaaacga    3720
cgagcgtgac accacgatgc ctgtagcaat ggcaacaacg ttgcgcaaac tattaactgg    3780
cgaactactt actctagctt cccggcaaca attaatagac tggatggagg cggataaagt    3840
tgcaggacca cttctgcgct cggcccttcc ggctggctgg tttattgctg ataaatctgg    3900
agccggtgag cgtgggtctc gcggtatcat tgcagcactg gggccagatg gtaagccctc    3960
ccgtatcgta gttatctaca cgacggggag tcaggcaact atggatgaac gaaatagaca    4020
gatcgctgag ataggtgcct cactgattaa gcattggtaa ctgtcagacc aagtttactc    4080
atatatactt tagattgatt taaaacttca ttttttaattt aaaaggatct aggtgaagat    4140
cctttttgat aatctcatga ccaaaatccc ttaacgtgag ttttcgttcc actgagcgtc    4200
agaccccgta gaaaagatca aaggatcttc ttgagatcct ttttttctgc gcgtaatctg    4260
ctgcttgcaa acaaaaaaac caccgctacc agcggtggtt tgtttgccgg atcaagagct    4320
accaactctt tttccgaagg taactggctt cagcagagcg cagataccaa atactgttct    4380
tctagtgtag ccgtagttag gccaccactt caagaactct gtagcaccgc ctacatacct    4440
cgctctgcta atcctgttac cagtggctgc tgccagtggc gataagtcgt gtcttaccgg    4500
gttggactca agacgatagt taccggataa ggcgcagcgg tcgggctgaa cggggggttc    4560
gtgcacacag cccagcttgg agcgaacgac ctacaccgaa ctgagatacc tacagcgtga    4620
gctatgagaa agcgccacgc ttcccgaagg agaaaggcg gacaggtatc cggtaagcgg    4680
cagggtcgga acaggagagc gcacgaggga gcttccaggg ggaaacgcct ggtatcttta    4740
tagtcctgtc gggtttcgcc acctctgact tgagcgtcga ttttttgtgat gctcgtcagg    4800 ggggcggagc ctatgaaaa acgccagcaa cgcggccttt ttacggttcc tggccttttg    4860
ctggcctttt gctcacatgt tctttcctgc gttatcccct gattctgtgg ataaccgtat    4920
taccgccttt gagtgagctg ataccgctcg ccgcagccga acgaccgagc gcagcgagtc    4980
agtgagcgag gaagcggaag agcgcccaat acgcaaaccg cctctccccg cgcgttggcc    5040
gattcattaa tgcagctggc acgacaggtt cccgactgg aaagcgggca gtgagcgcaa    5100
cgcaattaat gtgagttagc tcactcatta ggcaccccag gctttacact ttatgcttcc    5160
ggctcgtatg ttgtgtggaa ttgtgagcgg ataacaattt cacacaggaa acagctatga    5220
ccatgattac gccagattta attaaggcct taattagg                             5258

<210> SEQ ID NO 10
<211> LENGTH: 2393
<212> TYPE: DNA
<213> ORGANISM: Human

<400> SEQUENCE: 10
ctgcgcgctc gctcgctcac tgaggccgcc cgggcaaagc ccgggcgtcg ggcgaccttt      60
ggtcgcccgg cctcagtgag cgagcgagcg cgcagagagg gagtgtagcc atgctctagg    120
aagatcaatt cggtacaatt cacgcgtcga caattgaggg cgtcaccgct aaggctccgc    180
```

```
cccagcctgg gctccacaac caatgaaggg taatctcgac aaagagcaag gggtggggcg    240
cgggcgcgca ggtgcagcag cacacaggct ggtcggagg gcggggcgcg acgtctgccg     300
tgcggggtcc cggcatcggt tgcgcgcgcg ctccctcctc tcggagagag ggctgtggta    360
aaacccgtcc ggaaaatggc tgcagccgct gccgcagcgc cgagcggcgg aggtggcggt    420
ggcgaggagg agagactgga agaaaagtca gaagaccagg acctccaggg cctcaaggac    480 aaaccccctca gtttaaaaa ggtgaagaaa gataagaaag aagagaaaga gggcaagcat    540
gagcccgtgc agccatcagc ccaccactct gctgagcccg cagaggcagg caaagcagag    600
acatcagaag ggtcaggctc cgccccggct gtgccggaag cttctgcctc ccccaaacag    660
cggcgctcca tcatccgtga ccggggaccc atgtatgatg accccaccct gcctgaaggc    720
tggacacgga agcttaagca aaggaaatct ggacgctctg ctgggaagta tgatgtgtat    780
ttgatcaatc cccagggaaa agcctttcgc tctaaagtgg agttgattgc gtacttcgaa    840
aaggtaggcg acacatccct ggaccctaat gattttgact tcacggtaac tgggagaggg    900
agcccctccc ggcgagagca gaaaccacct aagaagccca atctcccaa agctccagga    960 actggcagag gtcggggacg ccccaaaggg agcggcacca cgagacccaa ggcagctacg   1020
tcagagggtg tgcaggtgaa aagggtcctg agaaaagtc ctgggaagct ccttgtcaag   1080 atgcctttc aaacttcgcc aggggcaag gctgaggggg gtggggccac cacatccacc   1140
caggtcatgg tgatcaaacg ccccggcagg aagcgaaaag ctgaggcaga ccctcaggcc   1200
attcccaaga acggggtcg aaagccgggg agtgtggtgg cagccgctgc cgccgaggcc   1260
aaaaagaaag ccgtgaagga gtcttctatc cgatctgtgc aggagaccgt actccccatc   1320
aagaagcgca agaccccggga gacggtcagc atcgaggtca aggaagtggt gaagcccctg   1380
ctggtgtcca ccctcggtga aagagcggg aaaggactga agacctgtaa gagccctggg   1440
cggaaaagca aggagagcag ccccaagggg cgcagcagca gcgcctcctc acccccaag   1500 aaggagcacc accaccatca ccaccactca gagtccccaa aggcccccgt gccactgctc   1560 ccaccccctgc ccccaccctcc acctgagccc gagagctccg aggacccac cagccccct   1620 gagccccagg acttgagcag cagcgtctgc aaagaggaga gatgcccag aggaggctca   1680 ctggagagcg acggctgccc caaggagcca gctaagactc agcccgcggt tgccaccgcc   1740
gccacggccg cagaaaagta caaacaccga ggggagggag agcgcaaaga cattgttttca   1800 tcctccatgc caaggccaaa cagagaggag cctgtggaca gccggacgcc cgtgaccgag   1860
agagttagcg agcagaagct gatctcgag gaggacctgt gacgaccatg gctgtagact   1920
gttactcgag atacatactt ctttacattc aatacatac ttctttacat tccaatacat   1980 acttcttttac attccaccat ggactagtac aaacaccatt gtcacactcc aacaaacacc   2040
attgtcacac tccaacaaac accattgtca cactccagcg gccgcttcga tccgatcttt   2100
ttccctctgc caaaaattat ggggacatca tgaagcccct tgagcatctg acttctggct   2160
aataaaggaa atttatttc attgcaatag tgtgttggaa tttttttgtgt ctctcactcg   2220 gcctaggtag ataagtagca tggcgggtta atcattaact acaaggaacc cctagtgatg   2280
gagttggcca ctccctctct gcgcgctcgc tcgctcactg aggccgggcg accaaaggtc   2340
gcccgacgcc cgggctttgc ccgggcggcc tcagtgagcg agcgagcgcg cag          2393
```

<210> SEQ ID NO 11
<211> LENGTH: 2415
<212> TYPE: DNA
<213> ORGANISM: Human

<400> SEQUENCE: 11

```
ctgcgcgctc gctcgctcac tgaggccgcc cgggcaaagc ccgggcgtcg ggcgaccttt        60
ggtcgcccgg cctcagtgag cgagcgagcg cgcagagagg gagtgtagcc atgctctagg       120
aagatcaatt cggtacaatt cacgcgtcga caattgaggg cgtcaccgct aaggctccgc       180
cccagcctgg gctccacaac caatgaaggg taatctcgac aaagagcaag gggtggggcg       240
cgggcgcgca ggtgcagcag cacacaggct ggtcggagg gcggggcgcg acgtctgccg       300
tgcggggtcc cggcatcggt tgcgcgcgcg ctccctcctc tcggagagag ggctgtggta       360
aaacccgtcc ggaaaatggc tgcagccgct gccgcagcgc cgagcggcgg aggtggcggt       420
ggcgaggagg agagactgga agaaaagtca gaagaccagg acctccaggg cctcaaggac       480
aaaccctca agtttaaaaa ggtgaagaaa gataagaaag aagagaaaga gggcaagcat       540
gagcccgtgc agccatcagc ccaccactct gctgagcccg cagaggcagg caaagcagag       600
acatcagaag ggtcaggctc cgccccggct gtgccggaag cttctgcctc ccccaaacag       660
cggcgctcca tcatccgtga ccggggaccc atgtatgatg accccaccct gcctgaaggc       720
tggacacgga agcttaagca aaggaaatct ggacgctctg ctgggaagta tgatgtgtat       780
ttgatcaatc cccagggaaa agcctttcgc tctaaagtgg agttgattgc gtacttcgaa       840
aaggtaggcg acacatccct ggaccctaat gattttgact tcacggtaac tgggagaggg       900
agcccctccc ggcgagagca gaaaccacct aagaagccca atctcccaa agctccagga       960
actggcagag gtcggggacg ccccaaaggg agcggcacca cgagacccaa ggcagctacg      1020
tcagagggtg tgcaggtgaa aagggtcctg gagaaaagtc ctgggaagct ccttgtcaag      1080
atgccttttc aaacttcgcc aggggcaag gctgagggg gtggggccac cacatccacc       1140
caggtcatgg tgatcaaacg ccccggcagg aagcgaaaag ctgaggcaga ccctcaggcc      1200
attcccaaga acggggtcg aaagccgggg agtgtggtgg cagccgctgc cgccgaggcc      1260
aaaaagaaag ccgtgaagga gtcttctatc cgatctgtgc aggagaccgt actccccatc      1320
aagaagcgca agacccggga gacggtcagc atcgaggtca aggaagtggt gaagcccctg      1380
ctggtgtcca ccctcggtga aagagcggg aaaggactga agacctgtaa gagccctggg      1440
cggaaaagca aggagagcag ccccaagggg cgcagcagca gcgcctcctc acccccaag      1500
aaggagcacc accaccatca ccaccactca gagtccccaa aggcccccgt gccactgctc      1560
ccacccctgc ccccacctcc acctgagccc gagagctccg aggacccac cagccccct      1620
gagcccagg acttgagcag cagcgtctgc aaagaggaga gatgccag aggaggctca       1680
ctggagagcg acggctgccc caaggagcca gctaagactc agcccgcggt tgccaccgcc      1740
gccacggccg cagaaaagta caaacaccga ggggagggag agcgcaaaga cattgtttca      1800
tcctccatgc aaggccaaa cagagaggag cctgtggaca gccggacgcc cgtgaccgag      1860
agagttagcg agcagaagct gatctcagag gaggacctgt gacgaccatg gctgtagact      1920
gttacgacca tggctgtaga ctgttactcg agatacatac ttctttacat tccaatacat      1980
acttctttac attccaatac atacttcttt acattccacc atggactagt acaaacacca      2040
ttgtcacact ccaacaaaca ccattgtcac actccaacaa acaccattgt cacactccag      2100
cggccgcttc gatccgatct ttttcccctct gccaaaaatt atgggacat catgaagccc       2160
cttgagcatc tgacttctgg ctaataaagg aaatttattt tcattgcaat agtgtgttgg      2220
aattttttgt gtctctcact cggcctaggt agataagtag catggcgggt taatcattaa      2280
```

```
ctacaaggaa cccctagtga tggagttggc cactccctct ctgcgcgctc gctcgctcac    2340
tgaggccggg cgaccaaagg tcgcccgacg cccgggcttt gcccgggcgg cctcagtgag    2400
cgagcgagcg cgcag                                                    2415

<210> SEQ ID NO 12
<211> LENGTH: 2437
<212> TYPE: DNA
<213> ORGANISM: Human

<400> SEQUENCE: 12
ctgcgcgctc gctcgctcac tgaggccgcc cgggcaaagc ccgggcgtcg ggcgaccttt      60
ggtcgcccgg cctcagtgag cgagcgagcg cgcagagagg gagtgtagcc atgctctagg    120
aagatcaatt cggtacaatt cacgcgtcga caattgaggg cgtcaccgct aaggctccgc    180
cccagcctgg gctccacaac caatgaaggg taatctcgac aaagagcaag gggtggggcg    240
cgggcgcgca ggtgcagcag cacacaggct ggtcggagg gcggggcgcg acgtctgccg    300
tgcggggtcc cggcatcggt tgcgcgcgcg ctccctcctc tcggagagag ggctgtggta    360
aaacccgtcc ggaaaatggc tgcagccgct gccgcagcgc cgagcggcgg aggtggcggt    420
ggcgaggagg agagactgga agaaaagtca gaagaccagg acctccaggg cctcaaggac    480 aaaccctca gtttaaaaa ggtgaagaaa gataagaaag aagagaaaga gggcaagcat    540
gagcccgtgc agccatcagc ccaccactct gctgagcccg cagaggcagg caaagcagag    600
acatcagaag ggtcaggctc cgccccggct gtgccggaag cttctgcctc ccccaaacag    660
cggcgctcca tcatccgtga ccggggaccc atgtatgatg accccaccct gcctgaaggc    720
tggacacgga agcttaagca aaggaaatct ggacgctctg ctgggaagta tgatgtgtat    780
ttgatcaatc cccagggaaa agcctttcgc tctaaagtgg agttgattgc gtacttcgaa    840
aaggtaggcg acacatccct ggaccctaat gattttgact tcacggtaac tgggagaggg    900 agccctccc ggcgagagca gaaaccacct aagaagccca atctcccaa agctccagga    960 actggcagag gtcggggacg ccccaaaggg agcggcacca cgagacccaa ggcagctacg   1020
tcagagggtg tgcaggtgaa aagggtcctg gagaaaagtc ctgggaagct ccttgtcaag   1080
atgccttttc aaacttcgcc aggggggcaag gctgaggggg gtggggccac cacatccacc   1140
caggtcatgg tgatcaaacg ccccggcagg aagcgaaaag ctgaggcaga ccctcaggcc   1200
attcccaaga acggggtcg aaagccgggg agtgtggtgg cagccgctgc cgccgaggcc   1260
aaaaagaaag ccgtgaagga gtcttctatc cgatctgtgc aggagaccgt actccccatc   1320
aagaagcgca agacccggga cggtcagc atcgaggtca aggaagtggt gaagcccctg   1380
ctggtgtcca ccctcggtga aagagcggg aaaggactga agacctgtaa gagccctggg   1440
cggaaaagca aggagagcag ccccaagggg cgcagcagca gcgcctcctc accccccaag   1500
aaggagcacc accaccatca ccaccactca gagtccccaa aggcccccgt gccactgctc   1560
ccacccctgc cccaccctcc acctgagccc gagagctccg ggaccccac cagcccccct   1620 gagccccagg acttgagcag cagcgtctgc aaagaggaga gatgcccag aggaggctca   1680 ctggagagca acggctgccc caaggagcca gctaagactc agcccgcggt tgccaccgcc   1740
gccacggccg cagaaaagta caaacaccga ggggagggag agcgcaaaga cattgtttca   1800
tcctccatgc caaggccaaa cagagaggag cctgtggaca gccggacgcc cgtgaccgag   1860
agagttagcg agcagaagct gatctcgaga gaggacctgt gacgaccatg gctgtagact   1920
gttacgacca tggctgtaga ctgttacgac catggctgta gactgttact cgagatacat   1980
```

```
acttctttac attccaatac atacttcttt acattccaat acatacttct ttacattcca   2040
ccatggacta gtacaaacac cattgtcaca ctccaacaaa caccattgtc acactccaac   2100
aaacaccatt gtcacactcc agcggccgct tcgatccgat cttttcccct ctgccaaaaa   2160
ttatggggac atcatgaagc cccttgagca tctgacttct ggctaataaa ggaaatttat   2220
tttcattgca atagtgtgtt ggaatttttt gtgtctctca ctcggcctag tagataagt    2280 agcatggcgg gttaatcatt aactacaagg aaccccctagt gatggagttg ccactcccct  2340
ctctgcgcgc tcgctcgctc actgaggccg ggcgaccaaa ggtcgcccga cgcccgggct   2400
ttgcccgggc ggcctcagtg agcgagcgag cgcgcag                            2437
```

<210> SEQ ID NO 13
<211> LENGTH: 735
<212> TYPE: PRT
<213> ORGANISM: Human

<400> SEQUENCE: 13

```
Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Pro Val Lys Thr Ala Pro Gly Lys Lys Arg
    130                 135                 140

Pro Val Glu His Ser Pro Val Glu Pro Asp Ser Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
            180                 185                 190

Ala Ala Pro Ser Gly Leu Gly Thr Asn Thr Met Ala Thr Gly Ser Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285
```

```
Cys His Phe Ser Pro Arg Asp Trp Gln Arg Leu Ile Asn Asn Asn Trp
    290             295                 300
Gly Phe Arg Pro Lys Arg Leu Asn Phe Lys Leu Phe Asn Ile Gln Val
305             310                 315                 320
Lys Glu Val Thr Gln Asn Asp Gly Thr Thr Thr Ile Ala Asn Asn Leu
                325                 330                 335
Thr Ser Thr Val Gln Val Phe Thr Asp Ser Glu Tyr Gln Leu Pro Tyr
                340                 345                 350
Val Leu Gly Ser Ala His Gln Gly Cys Leu Pro Pro Phe Pro Ala Asp
            355                 360                 365
Val Phe Met Val Pro Gln Tyr Gly Tyr Leu Thr Leu Asn Asn Gly Ser
370                 375                 380
Gln Ala Val Gly Arg Ser Ser Phe Tyr Cys Leu Glu Tyr Phe Pro Ser
385                 390                 395                 400
Gln Met Leu Arg Thr Gly Asn Asn Phe Thr Phe Ser Tyr Thr Phe Glu
                405                 410                 415
Asp Val Pro Phe His Ser Ser Tyr Ala His Ser Gln Ser Leu Asp Arg
                420                 425                 430
Leu Met Asn Pro Leu Ile Asp Gln Tyr Leu Tyr Tyr Leu Ser Arg Thr
            435                 440                 445
Asn Thr Pro Ser Gly Thr Thr Thr Gln Ser Arg Leu Gln Phe Ser Gln
450                 455                 460
Ala Gly Ala Ser Asp Ile Arg Asp Gln Ser Arg Asn Trp Leu Pro Gly
465                 470                 475                 480
Pro Cys Tyr Arg Gln Gln Arg Val Ser Lys Thr Ser Ala Asp Asn Asn
                485                 490                 495
Asn Ser Glu Tyr Ser Trp Thr Gly Ala Thr Lys Tyr His Leu Asn Gly
            500                 505                 510
Arg Asp Ser Leu Val Asn Pro Gly Pro Ala Met Ala Ser His Lys Asp
            515                 520                 525
Asp Glu Glu Lys Phe Phe Pro Gln Ser Gly Val Leu Ile Phe Gly Lys
            530                 535                 540
Gln Gly Ser Glu Lys Thr Asn Val Asp Ile Glu Lys Val Met Ile Thr
545                 550                 555                 560
Asp Glu Glu Glu Ile Arg Thr Thr Asn Pro Val Ala Thr Glu Gln Tyr
                565                 570                 575
Gly Ser Val Ser Thr Asn Leu Gln Arg Gly Asn Arg Gln Ala Ala Thr
            580                 585                 590
Ala Asp Val Asn Thr Gln Gly Val Leu Pro Gly Met Val Trp Gln Asp
            595                 600                 605
Arg Asp Val Tyr Leu Gln Gly Pro Ile Trp Ala Lys Ile Pro His Thr
610                 615                 620
Asp Gly His Phe His Pro Ser Pro Leu Met Gly Gly Phe Gly Leu Lys
625                 630                 635                 640
His Pro Pro Pro Gln Ile Leu Ile Lys Asn Thr Pro Val Pro Ala Asn
                645                 650                 655
Pro Ser Thr Thr Phe Ser Ala Ala Lys Phe Ala Ser Phe Ile Thr Gln
                660                 665                 670
Tyr Ser Thr Gly Gln Val Ser Val Glu Ile Glu Trp Glu Leu Gln Lys
            675                 680                 685
Glu Asn Ser Lys Arg Trp Asn Pro Glu Ile Gln Tyr Thr Ser Asn Tyr
            690                 695                 700
Asn Lys Ser Val Asn Val Asp Phe Thr Val Asp Thr Asn Gly Val Tyr
```

```
                705                 710                 715                 720
Ser Glu Pro Arg Pro Ile Gly Thr Arg Tyr Leu Thr Arg Asn Leu
                        725                 730                 735

<210> SEQ ID NO 14
<211> LENGTH: 736
<212> TYPE: PRT
<213> ORGANISM: Human

<400> SEQUENCE: 14

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Lys Thr Ala Pro Gly Lys Lys Arg
130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350
```

Pro Tyr Val Leu Gly Ser Ala His Glu Gly Cys Leu Pro Phe Pro
            355                 360                 365

Ala Asp Val Phe Met Ile Pro Gln Tyr Gly Tyr Leu Thr Leu Asn Asp
370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
                420                 425                 430

Asp Arg Leu Met Asn Pro Leu Ile Asp Gln Tyr Leu Tyr Tyr Leu Ser
            435                 440                 445

Lys Thr Ile Asn Gly Ser Gly Gln Asn Gln Gln Thr Leu Lys Phe Ser
    450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
                500                 505                 510

Gly Arg Asn Ser Leu Met Asn Pro Gly Pro Ala Met Ala Ser His Lys
            515                 520                 525

Glu Gly Glu Asp Arg Phe Phe Pro Leu Ser Gly Ser Leu Ile Phe Gly
    530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
                580                 585                 590

Thr Gly Trp Val Gln Asn Gln Gly Ile Leu Pro Gly Met Val Trp Gln
            595                 600                 605

Asp Arg Asp Val Tyr Leu Gln Gly Pro Ile Trp Ala Lys Ile Pro His
610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
    675                 680                 685

Lys Glu Asn Ser Lys Arg Trp Asn Pro Glu Ile Gln Tyr Thr Ser Asn
690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735

<210> SEQ ID NO 15
<211> LENGTH: 743
<212> TYPE: PRT
<213> ORGANISM: Human

<400> SEQUENCE: 15

-continued

```
Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
                20                  25                  30

Lys Ala Asn Gln Gln His Gln Asp Asn Ala Arg Gly Leu Val Leu Pro
            35                  40                  45

Gly Tyr Lys Tyr Leu Gly Pro Gly Asn Gly Leu Asp Lys Gly Glu Pro
        50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415
```

-continued

```
Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
            435                 440                 445

Arg Thr Ile Asn Gly Ser Gly Gln Asn Gln Gln Thr Leu Lys Phe Ser
            450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
            515                 520                 525

Glu Gly Glu Asp Arg Phe Phe Pro Leu Ser Gly Ser Leu Ile Phe Gly
            530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Thr Leu Ala Val
                580                 585                 590

Pro Phe Lys Ala Gln Ala Gln Thr Gly Trp Val Gln Asn Gln Gly Ile
            595                 600                 605

Leu Pro Gly Met Val Trp Gln Asp Arg Asp Val Tyr Leu Gln Gly Pro
            610                 615                 620

Ile Trp Ala Lys Ile Pro His Thr Asp Gly Asn Phe His Pro Ser Pro
625                 630                 635                 640

Leu Met Gly Gly Phe Gly Met Lys His Pro Pro Pro Gln Ile Leu Ile
                645                 650                 655

Lys Asn Thr Pro Val Pro Ala Asp Pro Pro Thr Ala Phe Asn Lys Asp
            660                 665                 670

Lys Leu Asn Ser Phe Ile Thr Gln Tyr Ser Thr Gly Gln Val Ser Val
            675                 680                 685

Glu Ile Glu Trp Glu Leu Gln Lys Glu Asn Ser Lys Arg Trp Asn Pro
690                 695                 700

Glu Ile Gln Tyr Thr Ser Asn Tyr Tyr Lys Ser Asn Asn Val Glu Phe
705                 710                 715                 720

Ala Val Asn Thr Glu Gly Val Tyr Ser Glu Pro Arg Pro Ile Gly Thr
                725                 730                 735

Arg Tyr Leu Thr Arg Asn Leu
                740
```